(12) United States Patent
Park

(10) Patent No.: US 10,167,507 B2
(45) Date of Patent: Jan. 1, 2019

(54) METABOLIC DISEASES-RELATED ODORANT RECEPTOR GENES AND USE THEREOF

(75) Inventor: Tae Sun Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 871 days.

(21) Appl. No.: 13/992,128

(22) PCT Filed: Sep. 30, 2011

(86) PCT No.: PCT/KR2011/007267
§ 371 (c)(1),
(2), (4) Date: Aug. 19, 2013

(87) PCT Pub. No.: WO2012/077898
PCT Pub. Date: Jun. 14, 2012

(65) Prior Publication Data
US 2013/0338034 A1 Dec. 19, 2013

(30) Foreign Application Priority Data
Dec. 9, 2010 (KR) .................. 10-2010-0125349

(51) Int. Cl.
*C12Q 1/68* (2018.01)
*C12Q 1/6876* (2018.01)
*C12Q 1/6883* (2018.01)
*C07K 14/705* (2006.01)
*G01N 33/68* (2006.01)

(52) U.S. Cl.
CPC .......... *C12Q 1/6876* (2013.01); *C07K 14/705* (2013.01); *C12Q 1/6883* (2013.01); *G01N 33/6893* (2013.01); *C12Q 2600/136* (2013.01); *C12Q 2600/158* (2013.01)

(58) Field of Classification Search
None
See application file for complete search history.

(56) References Cited

PUBLICATIONS

NM_146416, Mus musculus olfactory receptor 290, mRNA sequence, Young et al. 2003.*
Catalán et al., "Association of increased Visfatin/PBEF/NAMPT circulating concentrations and gene expression levels in peripheral blood cells with lipid metabolism and fatty liver in human morbid obesity," *Nutr. Metab. Cardiovasc. Dis.* 21(4): 245-253 (2011).
Guo et al., "Lipocalin-2 Deficiency Impairs Thermogenesis and Potentiates Diet-Induced Insulin Resistance in Mice," *Diabetes* 59: 1376-1385 (2010).
Kim et al, "Genes are differentially expressed in the epididymal fat of rats rendered obese by a high-fat diet," *Nutrition Research* 28: 414-422 (2008).
International Search Report for PCT/KR2011/007267, dated May 29, 2012 (3 pages).

* cited by examiner

*Primary Examiner* — Celine X Qian
(74) *Attorney, Agent, or Firm* — Clark & Elbing LLP; Susan M. Michaud

(57) ABSTRACT

The present invention relates to a diagnostic kit for metabolic diseases selected from the group consisting of obesity, dyslipidemia, fatty liver, and insulin resistance syndrome, and a method for screening a therapeutic composition for said diseases. The invention provides a large number of new gene targets for metabolic diseases such as obesity and the like, thereby enabling a more reliable diagnosis of genes such as obesity and the like and the use in the screening of a therapeutic candidate material based on the new gene targets.

4 Claims, 3 Drawing Sheets
Specification includes a Sequence Listing.

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
ttcggaatca gctctgtgga                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
ccattgggtc agctcttgtg                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
agcatcataa ccctagatgg                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
gaagtcacgc ctttcataac                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
tcggtgcgtc taagatgagg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
tcaaggcaca ttttttgctcc                                                   20

<210> SEQ ID NO 7
<211> LENGTH: 19
<212> TYPE: DNA
<213> ORGANISM: Artificial Sequence

```
<220> FEATURE:
<223> OTHER INFORMATION: Synthetic construct

<400> SEQUENCE: 7
ttgcccgagt cagagaacc                                              19

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
cgtccacaat agcttcatag c                                           21

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
tgtctcagcc tcttctcatt                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
agatgatctg agtgtgaggg                                             20

<210> SEQ ID NO 11
<211> LENGTH: 25
<212> TYPE: DNA
<213> ORGANISM: Artificial Sequence
<220> FEATURE:
<223> OTHER INFORMATION: Synthetic construct

<400> SEQUENCE: 11
atgaagttcc tctctgcaag agact                                       25

<210> SEQ ID NO 12
<211> LENGTH: 24
<212> TYPE: DNA
<213> ORGANISM: Artificial Sequence
<220> FEATURE:
<223> OTHER INFORMATION: Synthetic construct

<400> SEQUENCE: 12
cactaggttt gccgagtaga tctc                                        24

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
cagaacacgg caaaatgagc                                             20
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
gaggttgaca gcaaaatcct g                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
actgacagat ggagccgtga                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
gctgcatggt tctgagtgct                                                20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
gggacctaca atgcttacag                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
ggtcatatgt caccagctct                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
acggatgtgg tgaaggtccg                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 20
tacaaacatc atcacgttcc                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
agaacatcat ccctgcatcc                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
tccaccaccc tgttgctgta                                               20

<210> SEQ ID NO 23
<211> LENGTH: 23
<212> TYPE: DNA
<213> ORGANISM: Artificial Sequence
<220> FEATURE:
<223> OTHER INFORMATION: Synthetic construct

<400> SEQUENCE: 23
tgacgacttc gacttcgacg acg                                           23

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
tagggcaccg aggaatacc                                                19

<210> SEQ ID NO 25
<211> LENGTH: 948
<212> TYPE: DNA
<213> ORGANISM: Mus musculus

<400> SEQUENCE: 25
atggacgtct acaatcttac cacagtgact cagttcatcc tcatagggct ctctgacctc    60
cctgaagtgc gctatccact ctttgtggcc tttgtcatca tctatcagat cactttactg   120
ggaaatgggc tcatcctctt ggccattgtg actgagaaaa agcttcaaac tcccatgtat   180
tacctgttgg caaatctgtc cttactggac atattctgcc catcagctac tgtccccaag   240
atgcttaaga atctcttgac tgaggatcac agcatttcct tgttgggtg tgctttacag   300 ctctatttcc tggtggctct agctgggact gaagtcttct tgctggctgt gatggcttat   360
gaccggtatg tggccatatg ctttcctcta cgttactctc tcattatgac caaggttcgc   420
tgtgtgcagc tgttgtttgg gacttgggca gctgggtttc tgaactcctt tgtccacaca   480
atgtccacct ttagcctgtc tttctgcaat tctaatagag ttaatcagta ctactgtgat   540
```

| | | |
|---|---|---|
| attccacctg tggtggccct gtcatgctca tctacctata tggcagaaat gcttgtttta | 600 | |
| gtgataggag gtatctgtgg ggttggtgct tttctgatca ctctgatctc ctacatatac | 660 | |
| attgtctcca ccatcctaaa gatccggtca gctgaaggaa agcgcaaagc tttctccaca | 720 | |
| tgtgcttccc atcttcttgt agtcttcttg ttctatggca ccactatatt tacctatatt | 780 | |
| cgcccaacct ccagtcaaca ctctcctggt agagacagac tcatctctat gttgtatggg | 840 | |
| gtcattactc ccatgttaaa ccccattatc tacagtctga aaacacaga agtcaaagga | 900 | |
| gctctaagaa aagttttaca tcttcggata tgttcacaga gagaatga | 948 | |

<210> SEQ ID NO 26
<211> LENGTH: 315
<212> TYPE: PRT
<213> ORGANISM: Mus musculus

<400> SEQUENCE: 26

Met Asp Val Tyr Asn Leu Thr Thr Val Thr Gln Phe Ile Leu Ile Gly
1               5                   10                  15

Leu Ser Asp Leu Pro Glu Val Arg Tyr Pro Leu Phe Val Ala Phe Val
            20                  25                  30

Ile Ile Tyr Gln Ile Thr Leu Leu Gly Asn Gly Leu Ile Leu Leu Ala
        35                  40                  45

Ile Val Thr Glu Lys Lys Leu Gln Thr Pro Met Tyr Tyr Leu Leu Ala
50                  55                  60

Asn Leu Ser Leu Leu Asp Ile Phe Cys Pro Ser Ala Thr Val Pro Lys
65                  70                  75                  80

Met Leu Lys Asn Leu Leu Thr Glu Asp His Ser Ile Ser Phe Val Gly
                85                  90                  95

Cys Ala Leu Gln Leu Tyr Phe Leu Val Ala Leu Ala Gly Thr Glu Val
            100                 105                 110

Phe Leu Leu Ala Val Met Ala Tyr Asp Arg Tyr Val Ala Ile Cys Phe
        115                 120                 125

Pro Leu Arg Tyr Ser Leu Ile Met Thr Lys Val Arg Cys Val Gln Leu
130                 135                 140

Leu Phe Gly Thr Trp Ala Ala Gly Phe Leu Asn Ser Phe Val His Thr
145                 150                 155                 160

Met Ser Thr Phe Ser Leu Ser Phe Cys Asn Ser Asn Arg Val Asn Gln
                165                 170                 175

Tyr Tyr Cys Asp Ile Pro Pro Val Val Ala Leu Ser Cys Ser Ser Thr
            180                 185                 190

Tyr Met Ala Glu Met Leu Val Leu Val Ile Gly Gly Ile Cys Gly Val
        195                 200                 205

Gly Ala Phe Leu Ile Thr Leu Ile Ser Tyr Ile Tyr Ile Val Ser Thr
210                 215                 220

Ile Leu Lys Ile Arg Ser Ala Glu Gly Lys Arg Lys Ala Phe Ser Thr
225                 230                 235                 240

Cys Ala Ser His Leu Leu Val Val Phe Leu Phe Tyr Gly Thr Thr Ile
                245                 250                 255

Phe Thr Tyr Ile Arg Pro Thr Ser Ser Gln His Ser Pro Gly Arg Asp
            260                 265                 270

Arg Leu Ile Ser Met Leu Tyr Gly Val Ile Thr Pro Met Leu Asn Pro
        275                 280                 285

Ile Ile Tyr Ser Leu Arg Asn Thr Glu Val Lys Gly Ala Leu Arg Lys
290                 295                 300

-continued

```
Val Leu His Leu Arg Ile Cys Ser Gln Arg Glu
305                 310                 315
```

METABOLIC DISEASES-RELATED ODORANT RECEPTOR GENES AND USE THEREOF

CROSS-REFERENCE TO RELATED APPLICATIONS

This application is the U.S. national stage filing under 35 U.S.C. § 371 of International Application No. PCT/KR2011/007267, filed Sep. 30, 2011, which claims priority from Korean Patent Application 10-2010-125349, filed Dec. 9, 2010.

FIELD OF THE INVENTION

The present invention relates to olfactory receptor genes implicated in metabolic diseases and a kit for diagnosing metabolic diseases, and a use in screening method.

DESCRIPTION OF THE RELATED ART

In order to commercialize obesity-therapeutic agents which are possible to commercialize in global markets as well as domestic markets, there is a great need for researches on mechanisms and target proteins for anti-obesity effectiveness of materials. Targets of therapeutic agents (action points) currently being used in obesity and metabolic disease have been developed or developing. They may be divided into four major categories as follows: first, targets related to control of appetite, for example, CBR (cannabinoid receptor) antagonists, 5-HT2c (selective 5-hydroxytryptamine receptor subtype 2c) agonists, MC4R (melanocortin receptor) agonists, MCH (melanin-concentrating hormone) antagonists and NPY (Neuropeptide Y) antagonists; second, targets related to control of metabolic rate or metabolism, for example, β3-AR (β3-adrenergic receptor) agonists, lipase inhibitors, lipid metabolism enzyme regulators (diacylglycerol acyltransferase, fatty acid synthase, acetyl-CoA carboxylase and stearyl-CoA desaturase); third, targets related to control of gastrointestinal action, for example, GLP-1 (glucagon-like peptide-1) receptor agonists, CCK-A (cholecystokinin-A) agonists, ghrelin antagonists; and finally, targets related to control of fatty acid oxidation, for example, PPAR (peroxisome proliferator-activated receptor) regulators, CPA (carboxypeptidase) inhibitors, PTP (protein tyrosine phosphatase) inhibitors and AMPK (AMP-activated protein kinase) regulators (Chakrabarti R. Pharmacotherapy of obesity: emerging drugs and targets, *Expert Opin. Ther. Targets* 13: 195 (2009)).

Olfactory receptor has been known that it is mainly expressed in olfactory epithelium. Where odor molecules in the air bind to olfactory receptor present in cell membranes of olfactory epithelium, $G_{olf}$ (olfactory G protein) is preferentially activated and then AC3 (olfactory-related adenylate cyclase) is subsequently activated. The latter stimulates the production of cAMP (cyclic AMP) from ATP in olfactory cells and activates calcium ion channels such that signals are ultimately transmitted to the brain to recognize the odor molecules. In case of human, it has been reported that approximately 1,200 different types of olfactory receptor isoforms exist. It is accounted for approximately 3% of human genes. Single olfactory receptor is in charge of 2-3 different types of odor molecules. According to combinations of approximately 100 different types of single olfactory receptors, human may be able to distinguish 10,000 different types of odors (odor molecules). It has been known that the olfactory receptors are mainly expressed in the olfactory epithelium. However, according to a recent study, olfactory-like chemosensory signaling has been reported to occur in other biological tissues besides the olfactory epithelium. i.e., it was determined that olfactory receptors, olfactory-related $AC_3$ and $G_{olf}$ genes were expressed in renal tissue as well as the olfactory epithelium to involve in the regulation of rennin secretion and glomerular filtration rate. However, obesity-related functions of the olfactory receptor were still unknown.

The present inventor has first found that various types of olfactory receptor were expressed in mouse peripheral tissues (fat tissue and muscle tissue) and also, the expressions of these olfactory receptors were regulated by diet-induced obesity. Therefore, it was found that a variety of odor compounds present in natural substances were selectively bound to numerous olfactory receptors present in cell membranes of peripheral tissues such as fat tissue, liver tissue and muscle tissue, and the latter was involved in fat accumulation, free fatty acid oxidation, thermogenesis, and insulin resistance regulation in peripheral tissues via $AC_3$.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

Technical Purposes of this Invention

The present inventors have made intensive researches to develop a novel gene target for various metabolic diseases including obesity caused by disorder of lipid metabolism. As a result, they have observed that various types of olfactory receptors are not only expressed in peripheral tissues, but also they are regulated by diet-induced obesity. Therefore, they have found that these expressions may be a novel molecular target for obesity.

Accordingly, it is an object of this invention to provide a kit for diagnosing a metabolic disease selected from a group consisting of dyslipidemia, fatty liver and insulin resistance syndrome, comprising a primer or a probe which is specifically hybridized with the nucleotide sequence of GenBank accession No. NM_146416.

It is another object of this invention to provide a method for screening a therapeutic composition for treating a metabolic disease selected from a group consisting of dyslipidemia, fatty liver and insulin resistance syndrome.

Other objects and advantages of the present invention will become apparent from the detailed description to follow taken in conjugation with the appended claims and drawings.

Technical Solutions of this Invention

In one aspect of the present invention, there is provided a kit for diagnosing a metabolic disease selected from a group consisting of dyslipidemia, fatty liver and insulin resistance syndrome, comprising a primer or a probe which is specifically hybridized with the nucleotide sequence selected from a group consisting of GenBank accession No. NM_146834, NM_207149, NM_001011758, NM_147015, NM_001011721, NM_146588, NM_207142, NM_147013, NM_001011783, NM_207561, NM_001011777, NM_146577, NM_147010, NM_146408, NM_146511, NM_146407, NM_146730, NM_146542, NM_207154, NM_146752, NM_146661, NM_146658, NM_146351, NM_146642, NM_146293, NM_001011753, NM_146817, NM_146649, NM_146532, NM_001011868, NM_001011816, NM_001011535, NM_146823, NM_146458, NM_001001810, NM_146459, NM_146901, NM_146899, NM_146288, NM_146891, NM_146790, NM_146788, NM_146476, NM_146977, NM_146981, NM_146342, NM_146975, NM_146394, NM_146908, NM_207254, NM_146404, NM_146885, NM_146403, NM_146884, NM_146652, NM_146887, NM_146889, NM_001011787, NM_207151, NM_146449, NM_146274, NM_146292, NM_207570, NM_001011870, NM_207703, NM_147071, NM_207571, NM_146308, NM_146541, NM_146283, NM_146911, NM_207573, NM_207574, NM_001011741, NM_146473, NM_147065, NM_146471, NM_146276, NM_146877, NM_146337, NM_146275, NM_146881, NM_181818, NM_146491, NM_146490, NM_001011525, NM_146984, NM_001011853, NM_146806, NM_146687, NM_146683, NM_146697, NM_146747, NM_001011841, NM_146869, NM_001011842, NM_146301, NM_146696, NM_020513, NM_146271, NM_207576, NM_206823, NM_146451, NM_146466, NM_146935, NM_146357, NM_146335, NM_146484, NM_001011808, NM_207550, NM_146429, NM_146405, NM_146606, NM_207553, NM_146688, NM_146489, NM_146824, NM_146280, NM_146457, NM_147036, NM_146281, NM_206903, NM_146878, NM_001011866, NM_001011770, NM_146947, NM_146949, NM_146628, NM_146940, NM_146941, NM_146625, NM_146624, NM_207235, NM_147051, NM_207555, NM_147023, NM_207224, NM_146825, NM_146347, NM_147006, NM_147008, NM_146706, NM_146709, NM_146715, NM_146722, NM_146717, NM_146655, NM_146273, NM_146576, NM_001005488, NM_146426, NM_146370, XM_891283, NM_146775, NM_146734, NM_146733, NM_146737, NM_146307, NM_146952, NM_146518, NM_001011814, NM_001011815, NM_146962, NM_001011782, NM_147101, NM_207621, NM_147103, NM_146359, NM_147109, NM_147115, NM_147111, NM_207556, NM_146731, NM_146955, NM_146841, NM_146812, NM_147119, NM_147072, NM_146329, NM_147077, NM_207144, NM_147056, NM_001011757, XM_993242, NM_147096, NM_147060, NM_147059, NM_147043, NM_146760, NM_001011848, NM_147095, NM_146358, NM_013620, NM_147069, NM_146598, NM_146599, NM_001011749, NM_001011542, NM_019486, NM_147033, NM_146780, NM_146316, NM_146319, NM_001011809, NM_146493, NM_146363, NM_146667, NM_207133, NM_146299, NM_207156, NM_001011829, NM_146422, NM_146864, NM_146863, NM_146547, NM_146266, NM_207008, NM_207620, NM_207559, NM_001011849, NM_146548, NM_001011821, NM_146550, NM_207159, NM_146670, NM_146677, NM_146676, NM_146300, NM_146567, NM_146282, NM_146525, NM_146524, NM_146558, NM_146903, NM_146882, NM_146749, NM_146883, NM_146417, NM_001011739, NM_146336, NM_146801, NM_146872, NM_146811, NM_146810, NM_001011864, NM_146782, NM_146441, NM_146442, NM_001011518, NM_146503, NM_146330, NM_146279, NM_146612, NM_146826, NM_147107, NM_147105, NM_146510, NM_146286, NM_146855, NM_146515, NM_146437, NM_146589, NM_146660, NM_001011833, NM_146640, NM_146531, NM_001011517, NM_146631, NM_146898, NM_146893, NM_001011803, NM_207631, NM_146832, NM_146534, NM_147066, NM_146692, NM_146634, NM_001011850, NM_019475, NM_019476, NM_147002, NM_146992, NM_146870, NM_146621, NM_146537, NM_146859, NM_146724, NM_146723, NM_146755, NM_147113, NM_147114, NM_146964, NM_147080, NM_146665, NM_146378, NM_146324, NM_146557, NM_146419, NM_146482, NM_146478, NM_146861, NM_207673, NM_001011695, NM_146866, NM_001011872, NM_147012, NM_146391, NM_001011735, NM_207135, NM_146843, NM_146594, NM_207632, NM_146348, NM_146645, NM_146641, NM_146294, XM_621554, XM_621555, NM_146895, NM_146778, NM_146789, NM_146970, NM_146983, NM_146341, NM_146794, NM_146377, NM_146985, NM_206816, NM_001005568, NM_146400, XM_888068, NM_146886, NM_146450, NM_146831, NM_146385, NM_147040, NM_001011737, NM_146744, NM_146540, NM_146488, NM_146910, NM_001011790, NM_146467, NM_146468, NM_146470, NM_146651, NM_146809, NM_001011839, NM_146684, NM_146371, NM_207575, NM_146291, NM_207138, NM_020514, NM_146585, NM_008763, NM_147068, NM_001011855, NM_146957, NM_146993, NM_146999, NM_146912, NM_010970, NM_010974, NM_001005520, NM_146269, NM_207552, NM_001005780, NM_146829, NM_001011767, NM_146536, NM_146500, NM_146948, NM_146939, NM_146662, XM_619748, NM_147007, NM_001011863, NM_146761, NM_146721, NM_207158, NM_146653, NM_001011869, NM_001011810, NM_146732, NM_146736, NM_146738, NM_146914, NM_001011871, NM_146725, NM_146956, NM_146960, NM_010997, NM_146840, NM_146325, NM_147091, NM_147085, NM_147089, NM_147052, NM_001011847, NM_146727, NM_147083, NM_147055, NM_146379, NM_001011755, NM_147044, NM_001011862, NM_146597, NM_147035, NM_146604, NM_146664, NM_001011754, NM_146430, NM_207558, NM_130866, NM_146933, NM_146554, NM_146929, NM_146552, NM_146776, NM_146526, NM_146528, NM_146412, NM_146310, NM_146754, NM_147053, NM_146354, NM_146822, NM_146477, NM_146508, NM_146854, NM_001011827, NM_147108, NM_147106, NM_001011785, NM_146434, NM_146762, NM_207134, NM_146838, NM_146632, NM_001011835, NM_206896, NM_146968, NM_146965, NM_207572, NM_146945, NM_146963, NM_146571, NM_146587, NM_207562, NM_146592, NM_001011825, NM_146836, NM_146402, NM_146362, NM_020515, NM_146635, NM_146990, NM_146646, NM_146997, NM_146485, NM_010980, NM_146951, NM_146623, NM_146338, NM_146305, NM_146830, NM_146774, NM_010998, NM_207143, NM_147094, NM_147076, NM_146315, NM_207146, NM_146758, NM_146596, NM_146479, NM_146785, NM_146456, NM_001011813, NM_146745, NM_207563, NM_207565, NM_146297, NM_147029, NM_146648, NM_146918, NM_207568, NM_146333, NM_146395, NM_146401, NM_146867, NM_146304, NM_146913, NM_207136, NM_130868, NM_147003, NM_019473, NM_146860, NM_146958, NM_001011801, NM_147022, NM_207137, NM_146988, NM_010991, NM_207160, NM_146520, NM_147112, NM_001025386, NM_147050, NM_146494, NM_146671, NM_146610, NM_146921, NM_146573, NM_146572, NM_147019, NM_207566, NM_146917, NM_001005227, NM_146902, NM_146966, NM_146474, NM_146852, NM_146679, NM_207626, NM_146703, NM_146313, NM_146691, NM_146633, NM_147025, NM_147064, NM_010990, NM_146372, NM_147063, NM_146353, NM_146555, NM_146786, NM_146375, NM_146439, NM_146506, NM_146436, NM_001011852, NM_147078, NM_001005485, NM_147030, NM_146637, NM_146907, NM_146916, NM_146469, NM_146701, NM_146636, NM_146796, NM_146265, NM_146322, NM_146759, NM_146617, NM_207230, NM_146502, NM_146711, NM_146311, NM_147079, NM_146959, NM_147074, NM_146392, NM_146682, NM_146674, NM_146424, NM_146787, NM_146746, NM_146507, NM_146611, NM_146615, XM_619781, NM_146629, NM_146630, NM_146974, NM_146447, NM_146448, NM_146699, NM_146693, NM_146995, NM_207175, NM_146619, NM_146718, NM_146583, NM_147070, NM_146284, NM_146605, NM_146845, NM_146349, NM_146464, NM_001005225, NM_146973, NM_146982, NM_146890, NM_207152, NM_146389, NM_146535, NM_207227, NM_147037, NM_146689, NM_146686, NM_146920, NM_001011751, XM_620674, NM_146346, NM_146987, NM_146444, NM_146819, NM_146925, NM_001011858, NM_146954, NM_146314, NM_147061, NM_001011738, NM_207201, NM_146564, NM_146272, NM_207141, NM_146514, NM_146504, NM_146828, NM_146570, NM_146568, NM_207564, NM_146846, NM_147031, NM_146644, NM_207150, NM_146713, NM_207132, NM_030553, NM_146739, NM_147093, NM_147041, NM_013618, NM_146750, NM_146339, NM_001011797, NM_146553, NM_146433, NM_206822, NM_146409, NM_146590, NM_146897, NM_146455, NM_146793, NM_146980, NM_146853, NM_146704, NM_001011840, NM_207554, NM_146416, NM_146708, NM_146413, NM_146926, NM_146498, NM_146497, NM_146743, NM_147084, NM_146814, NM_146492, NM_146668, NM_146551, NM_146423, NM_001011523, NM_146513, NM_147021, NM_146289, NM_146287, NM_146849, NM_146848, NM_146792, NM_146343, NM_147042, NM_008762, NM_001011831, NM_001011791, NM_001011736, NM_146446, NM_146938, NM_146368, NM_146374, NM_146270, NM_010984, NM_146445, NM_001011527, NM_001011846, NM_146306, NM_011002, NM_146453, NM_146579, NM_146365, NM_146591, NM_146323, NM_146695, NM_146443, NM_146495, NM_020291, NM_147046, NM_146522, NM_146868, XM_619779, NM_001011734, NM_146462, NM_207140, NM_146808, NM_207236, NM_146888, NM_146936, NM_001001809, NM_146411, NM_146924, NM_146735, NM_001011867, NM_147110, NM_147120, NM_147049, NM_054090, NM_146930, NM_146904, NM_182714, NM_146896, NM_021368, NM_146327, NM_146702, NM_146770, NM_146950, NM_147004, NM_146364, NM_147081, NM_146481, NM_146768, NM_146638, NM_207567, NM_207240, NM_207664, NM_146923, NM_001011789, NM_147009, NM_147122, NM_146666, NM_054091, NM_146285, NM_146566, NM_146578, NM_146835, NM_001013575, NM_146837, NM_146647, NM_146543, NM_146694, NM_146321, NM_146627, NM_146383, NM_146820, NM_146600, NM_146672, NM_001012266, NM_146561, NM_146440, NM_001011826, NM_147014, NM_147018, NM_146320, NM_146705, NM_146431, NM_146622, NM_146932N, M_146827, NM_146569, NM_147001, NM_146384, NM_146944, NM_146656, NM_147088, NM_001011793, BC051435, NM_146613, NM_147011, NM_146847, NM_146366, NM_146766, NM_001011775, NM_147000, NM_147005, NM_207622, NM_146934, NM_147032, NM_146278, NM_146527, NM_001011748, NM_146865, NM_146971, NM_146410, NM_146751, NM_207145, NM_146833, NM_146406, NM_146765, NM_207253, NM_146680, NM_001005524, NM_010983, NM_001011861, NM_146922, NM_147104, NM_146813, NM_207249, NM_146663, NM_146862, NM_146905, NM_146418, NM_147028, NM_146303, NM_146295, NM_147098, NM_146803 and NM_146784.

The present inventors have made intensive researches to develop a novel gene target for various metabolic diseases including obesity caused by disorder of lipid metabolism. As a result, they have observed that various types of olfactory receptors are not only expressed in peripheral tissues, but also they are regulated by diet-induced obesity. Therefore, they have found that these expressions may be a novel molecular target for obesity.

According to the present invention, various types of olfactory receptors are expressed in peripheral tissues such as fat and muscle, besides olfactory organ. A variety of odor compounds present in natural substances are selectively bound to numerous olfactory receptors present in cell membranes of peripheral tissues such as fat tissue, liver tissue and muscle tissue, and these olfactory receptors are involved in fat accumulation, free fatty acid oxidation, thermogenesis, and insulin resistance regulation in peripheral tissues via $AC_3$.

Based on these findings, the present inventors analyzed DEG (differentially expressed gene) of olfactory receptor genes in which the expression was regulated by more than 2-fold change as compared to the control group, in visceral fat, subcutaneous fat tissue and muscular tissue of mouse fed the high-fat diet.

The term used herein "dyslipidemia" encompasses to hyperlipidemia, including abnormal lipid conditions caused by aberrant lipoprotein metabolism as well as hypercholesterolemia, hypertriglyceridemia and low HDL-cholesterolemia.

The term used herein "fatty liver" refers to a condition where fat accumulates excessively in liver cells due to the disorder of lipid metabolism. It may cause various diseases such as angina, myocardial infarction, stroke, arteriosclerosis and pancreatitis.

The term used herein "diabetes" refers to a chronic disease characterized by relative or absolute lack of insulin, leading to glucose intolerance. As used herein, the term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or by insulin resistance.

The term used herein "insulin resistance" refers to a condition in which the natural hormone insulin becomes less effective at lowering blood sugars. When insulin resistance becomes apparent, the human body creates too much insulin to result in developments of not only hypertension and dyslipidemia but also heart diseases and diabetes.

Especially, in type 2 diabetes, the increase in insulin is unrecognized in muscle and fat tissue, such that insulin action does not occur.

The term used herein "insulin resistance syndrome" refers to a general term for disease which is induced by insulin resistance. It is characterized by cell resistance against insulin action, hyperinsulinemia, increase of very low density lipoprotein (VLDL) and triglyceride, decrease of high density lipoprotein (HDL) and hypertension. The insulin resistance syndrome is usually considered as a risk factor for cardiovascular disease and type 2 diabetes (Reaven GM., Role of insulin resistance in human disease, Diabetes, 37:1595-607 (1988)). In addition, it has been reported that insulin resistance increases intracellular oxidative stress together with risk factors such as hypertension, diabetes and smoking, and alters signal transduction to cause inflammatory responses, such that atherosclerosis is developed (Freeman B A et al., Biology of disease: free radicals and tissue injury, Lab. Invest. 47:412-26 (1982), Kawamura M et al., Pathophysiological concentrations of glucose promote oxidative modification of low density lipoprotein by a superoxide-dependent pathway, J. Clin. Invest. 94:771-8 (1994)).

The term used herein "metabolic diseases" refer to a group of a wide variety of diseases caused by risk factors for various cardiovascular diseases and type 2 diabetes, including insulin resistance and its related diverse and complicated metabolic and clinical abnormalities. In 1988, Reaven suggested that a common cause of these symptoms is insulin resistance and named insulin resistance syndrome; however, in 1998, WHO newly introduced the term "metabolic syndrome or metabolic diseases", because insulin resistance may not explain all the elements of these symptoms.

According to a preferred embodiment, the present nucleotide sequence is selected from a group consisting of GenBank accession No. NM_146693, NM_147025, NM_146610, NM_146366, NM_146648, NM_146640, NM_146632, NM_146416, NM_146997, NM_146770, NM_146819, NM_001011870, NM_008763, NM_146893, NM_147069, NM_146703, NM_147063, NM_146950, NM_146364, NM_146448, NM_146858, NM_146897, NM_146391, NM_146697, NM_147028, NM_001011757, NM_146849, NM_207137, NM_146750 and NM_146339. Among genes whose expression level is shown to be more than 2-fold change between the HFD mouse group and the normal diet mouse control group, the genes described above are those of whose expressions are regulated by various types of odor components having anti-obesity efficacy.

According to a preferred embodiment, the present kit is a microarray.

The probe or primer used in the present kit for diagnosing has a sequence complementary to the present nucleotide sequence. The term "complementary" is used herein to mean that the probe or the primer is sufficiently complementary to hybridize selectively to the present nucleotide sequence under the designated hybridization conditions or annealing conditions. Therefore, the term "complementary" has a different meaning to the terms "perfectly complementary", and the present primer or the probe may include one or more mismatch base sequences to the extent that the present probe or the primer may be selectively hybridized with the present nucleotide sequence. The term "primer" used herein means a single-stranded oligonucleotide which is capable of acting as a point of initiation of template-directed DNA synthesis when placed under proper conditions (i.e., in the presence of four different nucleoside triphosphates and a thermostable enzyme) in an appropriate buffer and at a suitable temperature. The suitable length of primers will depend on many factors, including temperature, application and source of primer, generally, 15-30 nucleotides in length. In general, shorter primers need lower temperature to form stable hybridization duplexes to templates.

The sequences of primers are not required to have perfectly complementary sequence to templates. The sequences of primers may comprise some mismatches, so long as they can be hybridized with templates and serve as primers. Therefore, the primers of this invention are not required to have perfectly complementary sequence to the nucleotide sequence as described above; it is sufficient that they have complementarity to the extent that they anneals specifically to the nucleotide sequence of the gene for acting as a point of initiation of synthesis. The primer design may be conveniently performed with referring to the above-described nucleotide sequences. For instance, the primer design may be carried out using computer programs for primer design (e.g., PRIMER 3 program).

The term "probe" used herein refers to a linear oligomer of natural or modified monomers or linkages, including deoxyribonucleotides and ribonucleotides, which is capable of specifically hybridizing with a target nucleotide sequence, whether occurring naturally or produced synthetically. The present probe may be prepared in the form of preferably single-stranded and oligodeoxyribonucleotide probe. The primer of this invention may be comprised of naturally occurring dNMP (i.e., dAMP, dGM, dCMP and dTMP), nucleotide analogue or derivative. The present probe may also include ribonucleotides. The present probe may include backbone-modified nucleotides, e.g., peptide nucleic acid (PNA) (M. Egholm et al., *Nature,* 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, sugar-modified nucleosides, e.g., 2'-O-methyl RNA, 2'-fluoro RNA, 2'-amino RNA, 2'-O— alkyl DNA, 2'-O-allyl DNA, 2'-O-alkynyl DNA, hexose DNA, pyranosyl RNA and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

In the present microarray, the present probes serve as a hybridizable array element and are immobilized on a substrate.

A preferable substrate includes suitable solid or semi-solid supporters, such as membrane, filter, chip, slide, wafer, fiber, magnetic or nonmagnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements are bound to a glass surface modified to contain epoxy compound or aldehyde group or to a polylysin-coated surface using UV. Further, the hybridizable array elements are bound to a substrate through linkers (e.g., ethylene glycol oligomer and diamine).

DNAs as sample to be examined with a microarray of this invention may be labeled, and hybridized with array elements on microarray. Various hybridization conditions are applicable. For the detection and analysis of the extent of hybridization, various methods are available depending on labels used.

The present kit for diagnosing a metabolic disease may be used in accordance with hybridization. For such analysis, probes which have a complementary sequence to the present nucleotide sequence are used. Using probes hybridizable with the nucleotide sequence, risks of metabolic diseases may be determined by hybridization-based assay. Labels linking to the probes may generate a signal to detect hybridization and bound to oligonucleotide. Suitable labels include fluorophores (e.g., fluorescein, phycoerythrin, rhodamine, lissamine, Cy3 and Cy5 (Pharmacia)), chromophores, chemiluminescents, magnetic particles, radioisotopes (e.g., $P^{32}$ and $S^{35}$), mass labels, electron dense particles, enzymes (e.g., alkaline phosphatase or horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation, random priming (Multiprime DNA labeling systems booklet, "Amersham" (1989)) and kination (Maxam & Gilbert, Methods in Enzymology, 65: 499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

The nucleic acid sample to be analyzed may be prepared using mRNA from various biosamples. Preferably, the biosample is fat tissue cells or muscular tissue cells. Instead of probes, cDNA of interest may be labeled for hyribridization-based analysis.

Where probes are used, they are hybridized with cDNA molecules. in the present invention, suitable hybridization conditions may be routinely determined by optimization procedures.

To establish a protocol for use of laboratory, these procedures may be carried out by various methods known to those ordinarily skilled in the art. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning*, A Laboratory Manual, Cold Spring Harbor Laboratory Press, Cold Spring Harbor, N.Y. (2001); and M. L. M. Anderson, *Nucleic Acid Hybridization*, Springer-Verlag New York Inc. N.Y. (1999). For example, the high stringent condition includes hybridization in 0.5 M NaHPO$_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Following hybridization reactions, a hybridization signal indicative of the occurrence of hybridization is then measured. The hybridization signal may be analyzed by a variety of methods depending on labels. For example, where probes are labeled with enzymes, the occurrence of hybridization may be detected by reacting substrates for enzymes with hybridization resultants. The enzyme/substrate pair useful in this invention includes, but is not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphtol/pyronine; a pair of alkaline phosphatase and bromochloroindolylphosphate (BCIP), nitro blue tetrazolium (NBT), naphthol-AS-B1-phosphate and ECF substrate; and a pair of glucose oxidase and t-NBT (nitroblue tetrazolium) or m-PMS (phenzaine methosulfate). Where probes are labeled with gold particles, the occurrence of hybridization may be detected by silver staining method using silver nitrate. In these connections, where the present method for predicting a risk of a metabolic disease is carried out by hybridization, it comprises the steps of: (i) hybridizing a nucleic acid sample to a probe having a sequence complementary to the present nucleotide sequence; and (ii) detecting the occurrence of hybridization. The signal intensity from hybridization is indicative of risk of obesity and metabolic diseases. i.e., when the hybridization signal from a sample to the olfactory receptor gene sequence determined by the present invention that it is highly expressed in a metabolic disease patient is measured to be stronger than normal samples (normal cells), the sample may be determined to have high risk of obesity and metabolic disease. In addition, when the hybridization signal from a sample to the olfactory receptor gene sequence determined by the present invention that it is low expressed in a metabolic disease patient is measured to be weaker than normal samples (normal cells), the sample may be determined to have high risk of obesity and metabolic disease.

According to a preferable embodiment, the kit of this invention may be a kit for gene amplification.

The term used herein "amplification" refers to reactions for amplifying nucleic acid molecules. A multitude of amplification reactions have been suggested in the art, including polymerase chain reaction (PCR) (U.S. Pat. Nos. 4,683,195, 4,683,202, and 4,800,159), reverse transcription-polymerase chain reaction (RT-PCR) (Sambrook, J. et al., *Molecular Cloning. A Laboratory Manual*, 3rd ed. Cold Spring Harbor Press (2001)), the methods of Miller, H. I. (WO 89/06700) and Davey, C. et al. (EP 329,822), ligase chain reaction (LCR), Gap-LCR (WO 90/01069), repair chain reaction (EP 439,182), transcription-mediated amplification (TMA; WO 88/10315), self sustained sequence replication (WO 90/06995), selective amplification of target polynucleotide sequences (U.S. Pat. No. 6,410,276), consensus sequence primed polymerase chain reaction (CP-PCR; U.S. Pat. No. 4,437,975), arbitrarily primed polymerase chain reaction (AP-PCR; U.S. Pat. Nos. 5,413,909 and 5,861,245), nucleic acid sequence based amplification (NASBA; U.S. Pat. Nos. 5,130,238, 5,409,818, 5,554,517 and 6,063,603), strand displacement amplification and loop-mediated isothermal amplification (LAMP), but not limited to. Other amplification methods that may be used are described in U.S. Pat. Nos. 5,242,794, 5,494,810, 4,988,617 and in U.S. Ser. No. 09/854,317. PCR is one of the most predominant processes for nucleic acid amplification and a number of its variations and applications have been developed. For example, for improving PCR specificity or sensitivity, touchdown PCR, hot start PCR, nested PCR and booster PCR have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR and thermal asymmetric interlaced PCR (TAIL-PCR) have been suggested for certain applications. The details of PCR can be found in McPherson, M. J., and Moller, S. G. PCR. BIOS Scientific Publishers, Springer-Verlag New York Berlin Heidelberg, N.Y. (2000), the teachings of which are incorporated herein by reference in its entity. Where the present kit is carried out using primers, the gene amplification is executed for analyzing the expression level of the present nucleotide sequence. Because the present invention is intended to assess the expression level of the present nucleotide sequence, their mRNA levels in samples are analyzed to determine the expression level of the nucleotide sequence. Therefore, the present invention may be generally carried out by gene amplifications using mRNA molecules in samples as templates and primers to be annealed to mRNA or cDNA. For obtaining mRNA molecules, total RNA is isolated from samples. The isolation of total RNA may be performed by various methods (see: Sambrook, J. et al., *Molecular Cloning. A Laboratory Manual*, 3rd ed. Cold Spring Harbor Press (2001); Tesniere, C. et al., *Plant Mol. Biol. Rep.*, 9:242 (1991); Ausubel, F. M. et al., *Current Protocols in Molecular Biology*, John Willey & Sons (1987); and Chomczynski, P. et al., *Anal. Biochem.* 162:156 (1987)). For example, total RNA in cells may be isolated using Trizol. Afterwards, cDNA molecules are synthesized using mRNA molecules isolated and then amplified. Since total RNA molecules used in the present invention are isolated from human samples, mRNA molecules have poly-A tails and converted to cDNA by use of dT primer and reverse transcriptase (*PNAS USA*, 85: 8998 (1988); Libert F, et al., *Science*, 244: 569 (1989); and Sambrook, J. et al., *Molecular Cloning. A Laboratory Manual*, 3rd ed. Cold Spring Harbor Press (2001)). cDNA molecules synthesized are then amplified by gene amplification reactions.

The primers used for the present invention is hybridized or annealed to a region on template so that double-stranded structure is formed. Conditions of nucleic acid hybridization suitable for forming such double stranded structures are described by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase obtained from a variety of bacterial species, including *Thermus aquaticus* (Taq), *Thermus thermophilus* (Tth), *Thermus filiformis, Thermis flavus, Thermococcus literalis*, and *Pyrococcus furiosus* (Pfu).

When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired. All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants.

Annealing or hybridization in the present invention is performed under stringent conditions that allow for specific binding between the target nucleotide sequence and the primer. Such stringent conditions for annealing will be sequence-dependent and varied depending on environmental parameters.

The amplified cDNA to the present nucleotide sequence are then analyzed to assess their expression level using suitable methods. For example, the amplified products are resolved by a gel electrophoresis and the bands generated are analyzed to assess the expression level of the present nucleotide sequence. Through these amplification reaction, when the expression level in a biosample to the olfactory receptor gene sequence determined by the present invention that it is highly expressed in a metabolic disease patient is measured to be higher than normal samples (normal cells), the sample may be determined to have high risk of obesity and metabolic disease. In addition, when the expression level in a biosample to the olfactory receptor gene sequence determined by the present invention that it is low expressed in a metabolic disease patient is measured to be lower than normal samples (normal cells), the sample may be determined to have high risk of obesity and metabolic disease.

Therefore, where the present method for detecting a marker of a metabolic disease is carried out by amplification reactions using cDNA, it comprises the steps of: (i) amplifying a nucleic acid sample by use of a primer to be annealed to the present nucleotide sequence; and (ii) analyzing the amplified products to determine the expression level of the present nucleotide sequence.

The present kit may optionally include other reagents along with components described above. For instance, where the present kit may be used for nucleic acid amplification, it may optionally include the reagents required for performing PCR reactions such as buffers, DNA polymerase (e.g., thermostable DNA polymerase obtained from *Thermus aquaticus* (Taq), *Thermus thermophilus* (Tth), *Thermus filiformis, Thermis flavus, Thermococcus literalis*, and *Pyrococcus furiosus* (Pfu)), DNA polymerase cofactors, and dNTPs. The present kit is manufactured to contain in separate packaging or compartments the constituents aforedescribed.

According to a preferable embodiment, the nucleotide sequence selected from a group consisting of GenBank accession No. NM_146834, NM_001011758, NM_001011721, NM_146588, NM_207142, NM_147013, NM_001011783, NM_207561, NM_001011777, NM_146577, NM_146407, NM_146730, NM_146542, NM_207154, NM_146752, NM_146661, NM_146642, NM_146293, NM_001011753, NM_146817, NM_146649, NM_001011816, NM_146823, NM_001001810, NM_146459, NM_146901, NM_146899, NM_146288, NM_146790, NM_146476, NM_146977, NM_146981, NM_146342, NM_146975, NM_146394, NM_146908, NM_207254, NM_146885, NM_146403, NM_146884, NM_146889, NM_001011787, NM_207151, NM_146274, NM_146292, NM_001011870, NM_207703, NM_147071, NM_146541, NM_146283, NM_146911, NM_207573, NM_001011741, NM_146473, NM_147065, NM_146276, NM_146877, NM_146275, NM_146881, NM_181818, NM_146491, NM_001011525, NM_146984, NM_001011853, NM_146806, NM_146687, NM_146697, NM_001011841, NM_146869, NM_146696, NM_207576, NM_206823, NM_146451, NM_146466, NM_146935, NM_146357, NM_001011808, NM_207550, NM_146429, NM_146606, NM_146824, NM_146457, NM_146281, NM_206903, NM_146878, NM_001011770, NM_146947, NM_146949, NM_146628, NM_146940, NM_146941, NM_146625, NM_146624, NM_147051, NM_207555, NM_146825, NM_147006, NM_146706, NM_146709, NM_146715, NM_146722, NM_001005488, XM_891283, NM_146775, NM_146952, NM_001011814, NM_001011815, NM_146962, NM_001011782, NM_147101, NM_207621, NM_147103, NM_147115, NM_147111, NM_146955, NM_146841, NM_146812, NM_147077, NM_207144, NM_147056, NM_001011757, NM_147096, NM_147060, NM_147059, NM_001011848, NM_146358, NM_013620, NM_146599, NM_001011749, NM_001011542, NM_147033, NM_146316, NM_001011809, NM_146493, NM_146363, NM_207133, NM_146299, NM_207156, NM_001011829, NM_146422, NM_146863, NM_207008, NM_207620, NM_207559, NM_001011849, NM_001011821, NM_207159, NM_146677, NM_146676, NM_146282, NM_146524, NM_146558, NM_146903, NM_146749, NM_146883, NM_146417, NM_146801, NM_146872, NM_146782, NM_146441, NM_146442, NM_146503, NM_146330, NM_146279, NM_146826, NM_147107, NM_147105, NM_146855, NM_146515, NM_146437, NM_001011695, NM_146866, NM_001011872, NM_146391, NM_001011735, NM_207135, NM_146348, NM_146645, XM_621554, NM_146778, NM_146789, NM_146983, NM_206816, NM_146400, NM_146450, NM_146831, NM_001011737, NM_146744, NM_146540, NM_146488, NM_146910, NM_146467, NM_146468, NM_146470, NM_146651, NM_146684, NM_146371, NM_207575, NM_008763, NM_147068, NM_001011855, NM_146957, NM_146912, NM_010970, NM_010974, NM_001005520, NM_207552, NM_001005780, NM_001011767, NM_146536, NM_146500, NM_146948, NM_146662, XM_619748, NM_147007, NM_001011863, NM_146761, NM_207158, NM_146653, NM_001011869, NM_001011810, NM_146732, NM_146736, NM_146914, NM_001011871, NM_146956, NM_146840, NM_146325, NM_147091, NM_147085, NM_147089, NM_147052, NM_001011847, NM_147083, NM_001011755, NM_146597, NM_147035, NM_146604, NM_001011754, NM_207558, NM_130866, NM_146933, NM_146929, NM_146552, NM_146526, NM_146528, NM_001011827, NM_147108, NM_147106, NM_001011785, NM_146571, NM_146587, NM_146402, NM_020515, NM_146635, NM_146646, NM_146485, NM_146623, NM_146338, NM_146305, NM_146774, NM_010998, NM_147094, NM_147076, NM_146315, NM_146758, NM_146479, NM_146785, NM_146456, NM_146573, NM_146572, NM_147019, NM_207566, NM_001005227, NM_146902, NM_146474, NM_146852, NM_146679, NM_207626, NM_146703, NM_146691, NM_146633, NM_147025, NM_147064, NM_146372, NM_147063, NM_146353, NM_146555, NM_146375, NM_146439, NM_146506, NM_146436, XM_619781, NM_146629, NM_146974, NM_146447, NM_146448, NM_146699, NM_146693, NM_146995, NM_207175, NM_146619, NM_146564, NM_146570, NM_146568, NM_207564, NM_146846, NM_147031, NM_146644, NM_207150, NM_207132, NM_030553, NM_146739, NM_147093, NM_013618, NM_146750, NM_146339, NM_146553, NM_146433, NM_147084, NM_147021, NM_146287, NM_146849, NM_146848, NM_146792, NM_146343, NM_147042, NM_008762, NM_001011831, NM_146938, NM_146374, NM_146270, NM_010984, NM_146445, NM_001011527, NM_001011846, NM_146306, NM_011002, NM_146453, NM_001011734, NM_146462, NM_207140, NM_146808, NM_207236, NM_146888, NM_146936, NM_001001809, NM_146411, NM_146924, NM_146735, NM_001011867, NM_147110, NM_147120, NM_147049, NM_054090, NM_146930, NM_146904, NM_182714, NM_146638, NM_207567, NM_207240, NM_207664, NM_146923, NM_001011789, NM_147009, NM_147122, NM_146666, NM_054091, NM_146285, NM_146566, NM_147014, NM_147018, NM_146320, NM_146705, NM_146431, NM_146622, NM_146932N, M_146827, NM_147011, NM_146847, NM_146366, NM_146766, NM_001011775, NM_147000, NM_147005, NM_207622, NM_146934, NM_147032, NM_146278, NM_146527, NM_001011748, NM_146865, NM_146833, NM_146406, NM_146765, NM_207253, NM_146680, NM_001005524, NM_010983, NM_001011861, NM_146922, NM_147104, NM_146813, NM_207249, NM_146663, NM_146862, NM_146905 and NM_146418 is high-expressed in a metabolic disease patient, and the nucleotide sequence selected from a group consisting of GenBank accession No. NM_146589, NM_146660, NM_001011833, NM_146640, NM_146531, NM_001011517, NM_146631, NM_146898, NM_146893, NM_001011803, NM_207631, NM_146832, NM_146534, NM_147066, NM_146692, NM_146634, NM_001011850, NM_019475, NM_019476, NM_147002, NM_146992, NM_146870, NM_146621, NM_146537, NM_146859, NM_146724, NM_146723, NM_146755, NM_147113, NM_147114, NM_146964, NM_147080, NM_146665, NM_146378, NM_146324, NM_146557, NM_146419, NM_146482, NM_146478, NM_146861, NM_146412, NM_146310, NM_146754, NM_147053, NM_146354, NM_146822, NM_146477, NM_146508, NM_146854, NM_146762, NM_207134, NM_146838, NM_146632, NM_001011835, NM_206896, NM_146968, NM_146965, NM_207572, NM_146945, NM_146963, NM_207565, NM_146297, NM_147029, NM_146648, NM_146294, NM_146918, NM_207568, NM_146333, NM_146395, NM_001005568, NM_146401, NM_146867, NM_146304, NM_146913, NM_207136, NM_130868, NM_147003, NM_146585, NM_019473, NM_146860, NM_146958, NM_001011801, NM_146405, NM_146269, NM_146688, NM_147022, NM_207137, NM_146721, NM_146988, NM_146734, NM_010991, NM_207160, NM_146520, NM_147112, NM_146727, NM_001025386, NM_147050, NM_146494, NM_146671, NM_146300, NM_146525, NM_146610, NM_001011852, NM_207563, NM_147078, NM_001005485, NM_207632, NM_147030, NM_146637, NM_146907, NM_146404, NM_146916, NM_146469, NM_146471, NM_146337, NM_146701, NM_146636, NM_146796, NM_146265, NM_146322, NM_146335, NM_146759, NM_146280, NM_146617, NM_207230, NM_146502, NM_207235, NM_146711, NM_146733, NM_146311, NM_147079, NM_146959, NM_147074, NM_146392, NM_146664, NM_146682, NM_146674, NM_146424, NM_146787, NM_146746, NM_146507, NM_146611, NM_146615, NM_207149, NM_146408, NM_146845, NM_001011825, NM_146349, NM_146658, NM_146836, NM_001011868, NM_146464, NM_001005225, NM_146458, NM_146973, NM_146788, NM_146966, NM_146982, NM_146890, NM_146652, NM_146362, NM_207570, NM_207152, NM_146389, NM_147040, NM_207571, NM_146535, NM_207227, NM_001011790, GM_207574, NM_147037, NM_146689, NM_146686, NM_207553, NM_146920, NM_001011751, NM_001011866, NM_010980, XM_620674, NM_147023, NM_146347, NM_146346, NM_146987, NM_146444, NM_146819, NM_146925, NM_146737, NM_001011858, NM_146725, NM_146954, NM_010997, NM_146731, NM_146314, NM_146841, NM_207146, NM_146760, NM_147061, NM_146319, NM_146667, NM_146430, NM_001011738, NM_146864, NM_207201, NM_146776, NM_146564, NM_146882, NM_001011739, NM_146811, NM_146272, NM_001011518, NM_207141, NM_146514, NM_146504, NM_146828, NM_146286, NM_206822, NM_147012, NM_146409, NM_146590, NM_146897, NM_146630, NM_146970, NM_146455, NM_146341, NM_146377, NM_146985, NM_146793, NM_146980, XM_888068, NM_146853, NM_146704, NM_146313, NM_001011840, NM_146301, NM_207138, NM_020513, NM_207554, NM_146829, NM_146416, NM_146951, NM_146708, NM_146273, NM_146413, NM_146370, NM_146926, NM_010990, NM_146498, NM_146497, NM_146743, NM_146359, NM_207143, NM_147084, NM_146329, NM_147055, NM_146814, NM_019486, NM_146780, NM_146492, NM_146668, NM_146551, NM_146554, NM_146423, NM_001011523, NM_001011813, NM_146513, NM_146612, NM_146510, NM_146434, NM_146579, NM_207562, NM_146592, NM_146365, NM_146591, NM_146323, NM_146695, NM_020514, NM_146997, NM_146443, NM_146576, NM_146426, NM_146495, NM_020291, NM_147046, NM_147069, NM_146547, NM_146548, NM_146567, NM_146522, NM_146868, NM_146745, NM_146917, NM_146896, NM_146794, NM_021368, NM_146327, NM_146308, NM_146490, NM_001011839, NM_146683, NM_146702, NM_146990, NM_146770, NM_147036, NM_146950, NM_147004, NM_146364, NM_147109, NM_207556, NM_147081, NM_147072, NM_146481, NM_146921, NM_207673, NM_146578, NM_146835, NM_001013575, NM_146837, NM_146647, NM_001011535, NM_146895, NM_146891, NM_146886, NM_146449, NM_146713, NM_146385, NM_146543, NM_146809, NM_146694, NM_146271, NM_146321, NM_001011736, NM_146627, NM_146368, NM_146718, NM_146383, NM_146738, NM_147041, NM_146820, NM_146600, NM_001011797, NM_146550, NM_146670, NM_146672, NM_001012266, NM_146561, NM_146336, NM_146810, NM_146440, NM_001011826, NM_146569, NM_147015, NM_147010, XM_619779, NM_146511, NM_146594, NM_146289, NM_146351, NM_146641, NM_146532, NM_146887, NM_146291, NM_147001, NM_146993, NM_146999, NM_001011791, NM_146484, NM_146384, NM_146489, NM_146944, NM_146717, NM_146830, NM_146655, NM_146656, NM_146307, NM_146960, NM_147088, NM_001011793, NM_146598, NM_001011862BC051435, NM_146613, NM_146971, NM_146410, NM_146747, NM_146446, NM_146751, NM_147043, NM_146596, NM_207145, NM_146843, NM_146768, NM_147028, XM_621555, NM_146303, NM_001011842, NM_146939, NM_207224, NM_147008, NM_146295, NM_146518, NM_147098, NM_147119, NM_146379, XM_993242, NM_147095, NM_147044, NM_146266, NM_146803, NM_146786, NM_146784 and NM_001011864 is low-expressed in a metabolic disease patient.

The term used herein "high expression" means that the nucleotide sequence of interest in a sample to be analyzed (e.g., fat tissue cells in obesity patient) is much more highly expressed than that in the normal sample (e.g., normal cells) (preferably, more than 2-fold). The term used herein "low expression" means that the nucleotide sequence of interest in a sample to be analyzed (e.g., fat tissue cells in obesity patient) is much more lowly expressed than that in the normal sample (preferably, more than 2-fold). The kit for diagnosing a metabolic disease may predict risks of metabolic diseases by analyzing whether the novel target nucleotide sequence developed by the present inventors is expressed highly or lowly.

According to a preferred embodiment, the dyslipidemia is hyperlipidemia.

The term used herein "hyperlipidemia" refers to a disease caused by higher level of blood lipids due to poor metabolism of lipids such as triglyceride and cholesterol. More specifically, hyperlipidemia is characterized by increased levels of lipids such as triglyceride, LDL cholesterol, phospholipids and free fatty acids in blood, including hypercholesterolemia and hypertriglyceridemia.

According to a preferred embodiment, the insulin resistance syndrome includes the disease which is one or more selected from a group consisting of obesity, hypertension, hyperlipidemia, hyperinsulinemia, non-alcoholic fatty liver and type 2 diabetes by insulin resistance syndrome.

In another aspect of the present invention, there is provided a method for screening a therapeutic composition for treating a metabolic disease selected from a group consisting of dyslipidemia, fatty liver and insulin resistance syndrome, comprising:

(a) contacting a sample of interest for analysis to a cell comprising the nucleotide sequence selected from a group consisting of GenBank accession No. NM_146834, NM_207149, NM_001011758, NM_147015, NM_001011721, NM_146588, NM_207142, NM_147013, NM_001011783, NM_207561, NM_001011777, NM_146577, NM_147010, NM_146408, NM_146511, NM_146407, NM_146730, NM_146542, NM_207154, NM_146752, NM_146661, NM_146658, NM_146351, NM_146642, NM_146293, NM_001011753, NM_146817, NM_146649, NM_146532, NM_001011868, NM_001011816, NM_001011535, NM_146823, NM_146458, NM_001001810, NM_146459, NM_146901, NM_146899, NM_146288, NM_146891, NM_146790, NM_146788, NM_146476, NM_146977, NM_146981, NM_146342, NM_146975, NM_146394, NM_146908, NM_207254, NM_146404, NM_146885, NM_146403, NM_146884, NM_146652, NM_146887, NM_146889, NM_001011787, NM_207151, NM_146449, NM_146274, NM_146292, NM_207570, NM_001011870, NM_207703, NM_147071, NM_207571, NM_146308, NM_146541, NM_146283, NM_146911, NM_207573, NM_207574, NM_001011741, NM_146473, NM_147065, NM_146471, NM_146276, NM_146877, NM_146337, NM_146275, NM_146881, NM_181818, NM_146491, NM_146490, NM_001011525, NM_146984, NM_001011853, NM_146806, NM_146687, NM_146683, NM_146697, NM_146747, NM_001011841, NM_146869, NM_001011842, NM_146301, NM_146696, NM_020513, NM_146271, NM_207576, NM_206823, NM_146451, NM_146466, NM_146935, NM_146357, NM_146335, NM_146484, NM_001011808, NM_207550, NM_146429, NM_146405, NM_146606, NM_207553, NM_146688, NM_146489, NM_146824, NM_146280, NM_146457, NM_147036, NM_146281, NM_206903, NM_146878, NM_001011866, NM_001011770, NM_146947, NM_146949, NM_146628, NM_146940, NM_146941, NM_146625, NM_146624, NM_207235, NM_147051, NM_207555, NM_147023, NM_207224, NM_146825, NM_146347, NM_147006, NM_147008, NM_146706, NM_146709, NM_146715, NM_146722, NM_146717, NM_146655, NM_146273, NM_146576, NM_001005488, NM_146426, NM_146370, XM_891283, NM_146775, NM_146734, NM_146733, NM_146737, NM_146307, NM_146952, NM_146518, NM_001011814, NM_001011815, NM_146962, NM_001011782, NM_147101, NM_207621, NM_147103, NM_146359, NM_147109, NM_147115, NM_147111, NM_207556, NM_146731, NM_146955, NM_146841, NM_146812, NM_147119, NM_147072, NM_146329, NM_147077, NM_207144, NM_147056, NM_001011757, XM_993242, NM_147096, NM_147060, NM_147059, NM_147043, NM_146760, NM_001011848, NM_147095, NM_146358, NM_013620, NM_147069, NM_146598, NM_146599, NM_001011749, NM_001011542, NM_019486, NM_147033, NM_146780, NM_146316, NM_146319, NM_001011809, NM_146493, NM_146363, NM_146667, NM_207133, NM_146299, NM_207156, NM_001011829, NM_146422, NM_146864, NM_146863, NM_146547, NM_146266, NM_207008, NM_207620, NM_207559, NM_001011849, NM_146548, NM_001011821, NM_146550, NM_207159, NM_146670, NM_146677, NM_146676, NM_146300, NM_146567, NM_146282, NM_146525, NM_146524, NM_146558, NM_146903, NM_146882, NM_146749, NM_146883, NM_146417, NM_001011739, NM_146336, NM_146801, NM_146872, NM_146811, NM_146810, NM_001011864, NM_146782, NM_146441, NM_146442, NM_001011518, NM_146503, NM_146330, NM_146279, NM_146612, NM_146826, NM_147107, NM_147105, NM_146510, NM_146286, NM_146855, NM_146515, NM_146437, NM_146589, NM_146660, NM_001011833, NM_146640, NM_146531, NM_001011517, NM_146631, NM_146898, NM_146893, NM_001011803, NM_207631, NM_146832, NM_146534, NM_147066, NM_146692, NM_146634, NM_001011850, NM_019475, NM_019476, NM_147002, NM_146992, NM_146870, NM_146621, NM_146537, NM_146859, NM_146724, NM_146723, NM_146755, NM_147113, NM_147114, NM_146964, NM_147080, NM_146665, NM_146378, NM_146324, NM_146557, NM_146419, NM_146482, NM_146478, NM_146861, NM_207673, NM_001011695, NM_146866, NM_001011872, NM_147012, NM_146391, NM_001011735, NM_207135, NM_146843, NM_146594, NM_207632, NM_146348, NM_146645, NM_146641, NM_146294, XM_621554, XM_621555, NM_146895, NM_146778, NM_146789, NM_146970, NM_146983, NM_146341, NM_146794, NM_146377, NM_146985, NM_206816, NM_001005568, NM_146400, XM_888068, NM_146886, NM_146450, NM_146831, NM_146385, NM_147040, NM_001011737, NM_146744, NM_146540, NM_146488, NM_146910, NM_001011790, NM_146467, NM_146468, NM_146470, NM_146651, NM_146809, NM_001011839, NM_146684, NM_146371, NM_207575, NM_146291, NM_207138, NM_020514, NM_146585, NM_008763, NM_147068, NM_001011855, NM_146957, NM_146993, NM_146999, NM_146912, NM_010970, NM_010974, NM_001005520, NM_146269, NM_207552, NM_001005780, NM_146829, NM_001011767, NM_146536, NM_146500, NM_146948, NM_146939, NM_146662, XM_619748, NM_147007, NM_001011863, NM_146761, NM_146721, NM_207158, NM_146653, NM_001011869, NM_001011810, NM_146732, NM_146736, NM_146738, NM_146914, NM_001011871, NM_146725, NM_146956, NM_146960, NM_010997, NM_146840, NM_146325, NM_147091, NM_147085, NM_147089, NM_147052, NM_001011847, NM_146727, NM_147083, NM_147055, NM_146379, NM_001011755, NM_147044, NM_001011862, NM_146597, NM_147035, NM_146604, NM_146664, NM_001011754, NM_146430, NM_207558, NM_130866, NM_146933, NM_146554, NM_146929, NM_146552, NM_146776, NM_146526, NM_146528, NM_146412, NM_146310, NM_146754, NM_147053, NM_146354, NM_146822, NM_146477, NM_146508, NM_146854, NM_001011827, NM_147108, NM_147106, NM_001011785, NM_146434, NM_146762, NM_207134, NM_146838, NM_146632, NM_001011835, NM_206896, NM_146968, NM_146965, NM_207572, NM_146945, NM_146963, NM_146571, NM_146587, NM_207562, NM_146592, NM_001011825, NM_146836, NM_146402, NM_146362, NM_020515, NM_146635, NM_146990, NM_146646, NM_146997, NM_146485, NM_010980, NM_146951, NM_146623, NM_146338, NM_146305, NM_146830, NM_146774, NM_010998, NM_207143, NM_147094, NM_147076, NM_146315, NM_207146, NM_146758, NM_146596, NM_146479, NM_146785, NM_146456, NM_001011813, NM_146745, NM_207563, NM_207565, NM_146297, NM_147029, NM_146648, NM_146918, NM_207568, NM_146333, NM_146395, NM_146401, NM_146867, NM_146304, NM_146913, NM_207136, NM_130868, NM_147003, NM_019473, NM_146860, NM_146958, NM_001011801, NM_147022, NM_207137, NM_146988, NM_010991, NM_207160, NM_146520, NM_147112, NM_001025386, NM_147050, NM_146494, NM_146671, NM_146610, NM_146921, NM_146573, NM_146572, NM_147019, NM_207566, NM_146917, NM_001005227, NM_146902, NM_146966, NM_146474, NM_146852, NM_146679, NM_207626, NM_146703, NM_146313, NM_146691, NM_146633, NM_147025, NM_147064, NM_010990, NM_146372, NM_147063, NM_146353, NM_146555, NM_146786, NM_146375, NM_146439, NM_146506, NM_146436, NM_001011852, NM_147078, NM_001005485, NM_147030, NM_146637, NM_146907, NM_146916, NM_146469, NM_146701, NM_146636, NM_146796, NM_146265, NM_146322, NM_146759, NM_146617, NM_207230, NM_146502, NM_146711, NM_146311, NM_147079, NM_146959, NM_147074, NM_146392, NM_146682, NM_146674, NM_146424, NM_146787, NM_146746, NM_146507, NM_146611, NM_146615, XM_619781, NM_146629, NM_146630, NM_146974, NM_146447, NM_146448, NM_146699, NM_146693, NM_146995, NM_207175, NM_146619, NM_146718, NM_146583, NM_147070, NM_146284, NM_146605, NM_146845, NM_146349, NM_146464, NM_001005225, NM_146973, NM_146982, NM_146890, NM_207152, NM_146389, NM_146535, NM_207227, NM_147037, NM_146689, NM_146686, NM_146920, NM_001011751, XM_620674, NM_146346, NM_146987, NM_146444, NM_146819, NM_146925, NM_001011858, NM_146954, NM_146314, NM_147061, NM_001011738, NM_207201, NM_146564, NM_146272, NM_207141, NM_146514, NM_146504, NM_146828, NM_146570, NM_146568, NM_207564, NM_146846, NM_147031, NM_146644, NM_207150, NM_146713, NM_207132, NM_030553, NM_146739, NM_147093, NM_147041, NM_013618, NM_146750, NM_146339, NM_001011797, NM_146553, NM_146433, NM_206822, NM_146409, NM_146590, NM_146897, NM_146455, NM_146793, NM_146980, NM_146853, NM_146704, NM_001011840, NM_207554, NM_146416, NM_146708, NM_146413, NM_146926, NM_146498, NM_146497, NM_146743, NM_147084, NM_146814, NM_146492, NM_146668, NM_146551, NM_146423, NM_001011523, NM_146513, NM_147021, NM_146289, NM_146287, NM_146849, NM_146848, NM_146792, NM_146343, NM_147042, NM_008762, NM_001011831, NM_001011791, NM_001011736, NM_146446, NM_146938, NM_146368, NM_146374, NM_146270, NM_010984, NM_146445, NM_001011527, NM_001011846, NM_146306, NM_011002, NM_146453, NM_146579, NM_146365, NM_146591, NM_146323, NM_146695, NM_146443, NM_146495, NM_020291, NM_147046, NM_146522, NM_146868, XM_619779, NM_001011734, NM_146462, NM_207140, NM_146808, NM_207236, NM_146888, NM_146936, NM_001001809, NM_146411, NM_146924, NM_146735, NM_001011867, NM_147110, NM_147120, NM_147049, NM_054090, NM_146930, NM_146904, NM_182714, NM_146896, NM_021368, NM_146327, NM_146702, NM_146770, NM_146950, NM_147004, NM_146364, NM_147081, NM_146481, NM_146768, NM_146638, NM_207567, NM_207240, NM_207664, NM_146923, NM_001011789, NM_147009, NM_147122, NM_146666, NM_054091, NM_146285, NM_146566, NM_146578, NM_146835, NM_001013575, NM_146837, NM_146647, NM_146543, NM_146694, NM_146321, NM_146627, NM_146383, NM_146820, NM_146600, NM_146672, NM_001012266, NM_146561, NM_146440, NM_001011826, NM_147014, NM_147018, NM_146320, NM_146705, NM_146431, NM_146622, NM_146932N, M_146827, NM_146569, NM_147001, NM_146384, NM_146944, NM_146656, NM_147088, NM_001011793, BC051435, NM_146613, NM_147011, NM_146847, NM_146366, NM_146766, NM_001011775, NM_147000, NM_147005, NM_207622, NM_146934, NM_147032, NM_146278, NM_146527, NM_001011748, NM_146865, NM_146971, NM_146410, NM_146751, NM_207145, NM_146833, NM_146406, NM_146765, NM_207253, NM_146680, NM_001005524, NM_010983, NM_001011861, NM_146922, NM_147104, NM_146813, NM_207249, NM_146663, NM_146862, NM_146905, NM_146418, NM_147028, NM_146303, NM_146295, NM_147098, NM_146803 and NM_146784; and (b) analyzing the expression level of the nucleotide sequence, where the sample inhibits the high-expression of the nucleotide sequence selected from a group consisting of GenBank accession No. NM_146834, NM_001011758, NM_001011721, NM_146588, NM_147142, NM_147013, NM_001011783, NM_207561, NM_001011777, NM_146577, NM_146407, NM_146730, NM_146542, NM_207154, NM_146752, NM_146661, NM_146642, NM_146293, NM_001011753, NM_146817, NM_146649, NM_001011816, NM_146823, NM_001001810, NM_146459, NM_146901, NM_146899, NM_146288, NM_146790, NM_146476, NM_146977, NM_146981, NM_146342, NM_146975, NM_146394, NM_146908, NM_207254, NM_146885, NM_146403, NM_146884, NM_146889, NM_001011787, NM_207151, NM_146274, NM_146292, NM_001011870, NM_207703, NM_147071, NM_146541, NM_146283, NM_146911, NM_207573, NM_001011741, NM_146473, NM_147065, NM_146276, NM_146877, NM_146275, NM_146881, NM_181818, NM_146491, NM_001011525, NM_146984, NM_001011853, NM_146806, NM_146687, NM_146697, NM_001011841, NM_146869, NM_146696, NM_207576, NM_206823, NM_146451, NM_146466, NM_146935, NM_146357, NM_001011808, NM_207550, NM_146429, NM_146606, NM_146824, NM_146457, NM_146281, NM_206903, NM_146878, NM_001011770, NM_146947, NM_146949, NM_146628, NM_146940, NM_146941, NM_146625, NM_146624, NM_147051, NM_207555, NM_146825, NM_147006, NM_146706, NM_146709, NM_146715, NM_146722, NM_001005488, XM_891283, NM_146775, NM_146952, NM_001011814, NM_001011815, NM_146962, NM_001011782, NM_147101, NM_207621, NM_147103, NM_147115, NM_147111, NM_146955, NM_146841, NM_146812, NM_147077, NM_207144, NM_147056, NM_001011757, NM_147096, NM_147060, NM_147059, NM_001011848, NM_146358, NM_013620, NM_146599, NM_001011749, NM_001011542, NM_147033, NM_146316, NM_001011809, NM_146493, NM_146363, NM_207133, NM_146299, NM_207156, NM_001011829, NM_146422, NM_146863, NM_207008, NM_207620, NM_207559, NM_001011849, NM_001011821, NM_207159, NM_146677, NM_146676, NM_146282, NM_146524, NM_146558, NM_146903, NM_146749, NM_146883, NM_146417, NM_146801, NM_146872, NM_146782, NM_146441, NM_146442, NM_146503, NM_146330, NM_146279, NM_146826, NM_147107, NM_147105, NM_146855, NM_146515, NM_146437, NM_001011695, NM_146866, NM_001011872, NM_146391, NM_001011735, NM_207135, NM_146348, NM_146645, XM_621554, NM_146778, NM_146789, NM_146983, NM_206816, NM_146400, NM_146450, NM_146831, NM_001011737, NM_146744, NM_146540, NM_146488, NM_146910, NM_146467, NM_146468, NM_146470, NM_146651, NM_146684, NM_146371, NM_207575, NM_008763, NM_147068, NM_001011855, NM_146957, NM_146912, NM_010970, NM_010974, NM_001005520, NM_207552, NM_001005780, NM_001011767, NM_146536, NM_146500, NM_146948, NM_146662, XM_619748, NM_147007, NM_001011863, NM_146761, NM_207158, NM_146653, NM_001011869, NM_001011810, NM_146732, NM_146736, NM_146914, NM_001011871, NM_146956, NM_146840, NM_146325, NM_147091, NM_147085, NM_147089, NM_147052, NM_001011847, NM_147083, NM_001011755, NM_146597, NM_147035, NM_146604, NM_001011754, NM_207558, NM_130866, NM_146933, NM_146929, NM_146552, NM_146526, NM_146528, NM_001011827, NM_147108, NM_147106, NM_001011785, NM_146571, NM_146587, NM_146402, NM_020515, NM_146635, NM_146646, NM_146485, NM_146623, NM_146338, NM_146305, NM_146774, NM_010998, NM_147094, NM_147076, NM_146315, NM_146758, NM_146479, NM_146785, NM_146456, NM_146573, NM_146572, NM_147019, NM_207566, NM_001005227, NM_146902, NM_146474, NM_146852, NM_146679, NM_207626, NM_146703, NM_146691, NM_146633, NM_147025, NM_147064, NM_146372, NM_147063, NM_146353, NM_146555, NM_146375, NM_146439, NM_146506, NM_146436, XM_619781, NM_146629, NM_146974, NM_146447, NM_146448, NM_146699, NM_146693, NM_146995, NM_207175, NM_146619, NM_146564, NM_146570, NM_146568, NM_207564, NM_146846, NM_147031, NM_146644, NM_207150, NM_207132, NM_030553, NM_146739, NM_147093, NM_013618, NM_146750, NM_146339, NM_146553, NM_146433, NM_147084, NM_147021, NM_146287, NM_146849, NM_146848, NM_146792, NM_146343, NM_147042, NM_008762, NM_001011831, NM_146938, NM_146374, NM_146270, NM_010984, NM_146445, NM_001011527, NM_001011846, NM_146306, NM_011002, NM_146453, NM_001011734, NM_146462, NM_207140, NM_146808, NM_207236, NM_146888, NM_146936, NM_001001809, NM_146411, NM_146924, NM_146735, NM_001011867, NM_147110, NM_147120, NM_147049, NM_054090, NM_146930, NM_146904, NM_182714, NM_146638, NM_207567, NM_207240, NM_207664, NM_146923, NM_001011789, NM_147009, NM_147122, NM_146666, NM_054091, NM_146285, NM_146566, NM_147014, NM_147018, NM_146320, NM_146705, NM_146431, NM_146622, NM_146932N, M_146827, NM_147011, NM_146847, NM_146366, NM_146766, NM_001011775, NM_147000, NM_147005, NM_207622, NM_146934, NM_147032, NM_146278, NM_146527, NM_001011748, NM_146865, NM_146833, NM_146406, NM_146765, NM_207253, NM_146680, NM_001005524, NM_010983, NM_001011861, NM_146922, NM_147104, NM_146813, NM_207249, NM_146663, NM_146862, NM_146905 and NM_146418, or where the sample inhibits the low-expression of the nucleotide sequence selected from a group consisting of GenBank accession No. NM_146589, NM_146660, NM_001011833, NM_146640, NM_146531, NM_001011517, NM_146631, NM_146898, NM_146893, NM_001011803, NM_207631, NM_146832, NM_146534, NM_147066, NM_146692, NM_146634, NM_001011850, NM_019475, NM_019476, NM_147002, NM_146992, NM_146870, NM_146621, NM_146537, NM_146859, NM_146724, NM_146723, NM_146755, NM_147113, NM_147114, NM_146964, NM_147080, NM_146665, NM_146378, NM_146324, NM_146557, NM_146419, NM_146482, NM_146478, NM_146861, NM_146412, NM_146310, NM_146754, NM_147053, NM_146354, NM_146822, NM_146477, NM_146508, NM_146854, NM_146762, NM_207134, NM_146838, NM_146632, NM_001011835, NM_206896, NM_146968, NM_146965, NM_207572, NM_146945, NM_146963, NM_207565, NM_146297, NM_147029, NM_146648, NM_146294, NM_146918, NM_207568, NM_146333, NM_146395, NM_001005568, NM_146401, NM_146867, NM_146304, NM_146913, NM_207136, NM_130868, NM_147003, NM_146585, NM_019473, NM_146860, NM_146958, NM_001011801, NM_146405, NM_146269, NM_146688, NM_147022, NM_207137, NM_146721, NM_146988, NM_146734, NM_010991, NM_207160, NM_146520, NM_147112, NM_146727, NM_001025386, NM_147050, NM_146494, NM_146671, NM_146300, NM_146525, NM_146610, NM_001011852, NM_207563, NM_147078, NM_001005485, NM_207632, NM_147030, NM_146637, NM_146907, NM_146404, NM_146916, NM_146469, NM_146471, NM_146337, NM_146701, NM_146636, NM_146796, NM_146265, NM_146322, NM_146335, NM_146759, NM_146280, NM_146617, NM_207230, NM_146502, NM_207235, NM_146711, NM_146733, NM_146311, NM_147079, NM_146959, NM_147074, NM_146392, NM_146664, NM_146682, NM_146674, NM_146424, NM_146787, NM_146746, NM_146507, NM_146611, NM_146615, NM_207149, NM_146408, NM_146845, NM_001011825, NM_146349, NM_146658, NM_146836, NM_001011868, NM_146464, NM_001005225, NM_146458, NM_146973, NM_146788, NM_146966, NM_146982, NM_146890, NM_146652, NM_146362, NM_207570, NM_207152, NM_146389, NM_147040, NM_207571, NM_146535, NM_207227, NM_001011790, NM_207574, NM_147037, NM_146689, NM_146686, NM_207553, NM_146920, NM_001011751, NM_001011866, NM_010980, XM_620674, NM_147023, NM_146347, NM_146346, NM_146987, NM_146444, NM_146819, NM_146925, NM_146737, NM_001011858, NM_146725, NM_146954, NM_010997, NM_146731, NM_146314, NM_146841, NM_207146, NM_146760, NM_147061, NM_146319, NM_146667, NM_146430, NM_001011738, NM_146864, NM_207201, NM_146776, NM_146564, NM_146882, NM_001011739, NM_146811, NM_146272, NM_001011518, NM_207141, NM_146514, NM_146504, NM_146828, NM_146286, NM_206822, NM_147012, NM_146409, NM_146590, NM_146897, NM_146630, NM_146970, NM_146455, NM_146341, NM_146377, NM_146985, NM_146793, NM_146980, XM_888068, NM_146853, NM_146704, NM_146313, NM_001011840, NM_146301, NM_207138, NM_020513, NM_207554, NM_146829, NM_146416, NM_146951, NM_146708, NM_146273, NM_146413, NM_146370, NM_146926, NM_010990, NM_146498, NM_146497, NM_146743, NM_146359, NM_207143, NM_147084, NM_146329, NM_147055, NM_146814, NM_019486, NM_146780, NM_146492, NM_146668, NM_146551, NM_146554, NM_146423, NM_001011523, NM_001011813, NM_146513, NM_146612, NM_146510, NM_146434, NM_146579, NM_207562, NM_146592, NM_146365, NM_146591, NM_146323, NM_146695, NM_020514, NM_146997, NM_146443, NM_146576, NM_146426, NM_146495, NM_020291, NM_147046, NM_147069, NM_146547, NM_146548, NM_146567, NM_146522, NM_146868, NM_146745, NM_146917, NM_146896, NM_146794, NM_021368, NM_146327, NM_146308, NM_146490, NM_001011839, NM_146683, NM_146702, NM_146990, NM_146770, NM_147036, NM_146950, NM_147004, NM_146364, NM_147109, NM_207556, NM_147081, NM_147072, NM_146481, NM_146921, NM_207673, NM_146578, NM_146835, NM_001013575, NM_146837, NM_146647, NM_001011535, NM_146895, NM_146891, NM_146886, NM_146449, NM_146713, NM_146385, NM_146543, NM_146809, NM_146694, NM_146271, NM_146321, NM_001011736, NM_146627, NM_146368, NM_146718, NM_146383, NM_146738, NM_147041, NM_146820, NM_146600, NM_001011797, NM_146550, NM_146670, NM_146672, NM_001012266, NM_146561, NM_146336, NM_146810, NM_146440, NM_001011826, NM_146569, NM_147015, NM_147010, XM_619779, NM_146511, NM_146594, NM_146289, NM_146351, NM_146641, NM_146532, NM_146887, NM_146291, NM_147001, NM_146993, NM_146999, NM_001011791, NM_146484, NM_146384, NM_146489, NM_146944, NM_146717, NM_146830, NM_146655, NM_146656, NM_146307, NM_146960, NM_147088, NM_001011793, NM_146598, NM_001011862BC051435, NM_146613, NM_146971, NM_146410, NM_146747, NM_146446, NM_146751, NM_147043, NM_146596, NM_207145, NM_146843, NM_146768, NM_147028, XM_621555, NM_146303, NM_001011842, NM_146939, NM_207224, NM_147008, NM_146295, NM_146518, NM_147098, NM_147119, NM_146379, XM_993242, NM_147095, NM_147044, NM_146266, NM_146803, NM_146786, NM_146784 and NM_001011864, it is determined as a therapeutic composition for treating obesity.

According to the present method, cells including the nucleotide sequence of the present olfactory receptor gene as target for metabolic diseases are first contacted to a sample to be analyzed. Preferably, the cells including the nucleotide sequence are fat tissue or muscle tissue cells. The term "sample" used herein in conjunction with the present screening method refers to a material tested in the present method for analyzing the influence on the expression level of the present nucleotide sequence. The sample includes chemical substances, nucleotide, antisense-RNA, siRNA (small interference RNA) and extracts of natural sources, but not limited thereto. Afterwards, the expression level of the nucleotide sequence is measured in cells treated with the sample. The measurement of the expression level may be carried out as described above. As a result, the sample may be determined as the therapeutic composition for treating a metabolic disease where the sample inhibits the high-expression or low-expression of the olfactory receptor gene sequence which is determined that it is highly or lowly expressed in a metabolic disease patient in the present invention.

Effects of this Invention

The features and advantages of this invention will be summarized as follows:

(a) The present invention provides a kit for diagnosing a metabolic disease selected from a group consisting of dyslipidemia, fatty liver and insulin resistance syndrome, and a method for screening a therapeutic composition thereof.

(b) The invention provides a large number of novel gene targets for metabolic diseases such as obesity and the like, thereby enabling a more reliable diagnosis for the genes and the use in the screening of a therapeutic candidate material based on the novel gene targets.

BEST MODE FOR CARRYING OUT THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Profile for Olfactory Receptors in which the Expression is Changed According to High-Fat Diet-Induced Period in Mouse Visceral Fat, Subcutaneous Fat Tissue and Muscular Tissue 1) High-Fat Diet-Induced Obesity Animal Model 5-week-old C57BL/6N mice were fed with high-fat diet (HFD, 20% fat energy) or normal diet (ND) (total 80 mice). At 2, 4, 8 and 12 weeks after the initiation of the study, 20 animals from each group were dissected to obtain sample. The ND was prepared according to AIN-76 rodent diet composition (American Institute of Nutrition, Report of the American Institute of Nutrition ad hoc committee on standards for nutritional studies. *J. Nutr.* 107: 1340-1348 (1977)). The test diet compositions are shown in Table 1.

TABLE 1

Compositions of test diets

| Ingredients | Normal diet (ND)(g/kg diet) | High-fat diet (HFD)(g/kg diet) |
|---|---|---|
| Casein | 200 | 200 |
| D/L-Methionine | 3 | 3 |
| Corn starch | 150 | 111 |
| Sucrose | 500 | 370 |
| Cellulose | 50 | 50 |
| Corn oil | 50 | 30 |
| Lard | — | 170 |
| Vitamin complex | 10 | 12 |
| Mineral complex | 35 | 42 |
| Choline bitartrate | 2 | 2 |
| Cholesterol | — | 10 |
| tert-butylhydroquinone | 0.01 | 0.04 |
| Total (g) | 1,000 | 1,000 |
| Fat (% calorie) | 11.5 | 39.0 |
| Total calorie (kJ/kg diet) | 16,439 | 19,315 |

The diet was given between 10 and 11 A.M. every day together with water. Food intake was measured every day and body weight was measured once a week. In order to avoid transient body weight increase after feed intake, body weight was measured 2 hours after removing the feed. After fasting the test animal for at least 12 hours and anesthetizing with diethyl ether, blood, liver, visceral fat (epididymal fat, perirenal fat, mesenteric fat and retroperitoneal fat), subcutaneous fat tissue and muscular tissue were taken and weighed after washing with 0.1 M PBS (pH 7.4). Blood taken from the abdominal aorta was centrifuged at 1000×g for 15 minutes for the separation of plasma.

2) Changes of Body and Visceral Fat-Pad Weights

Figure 1:
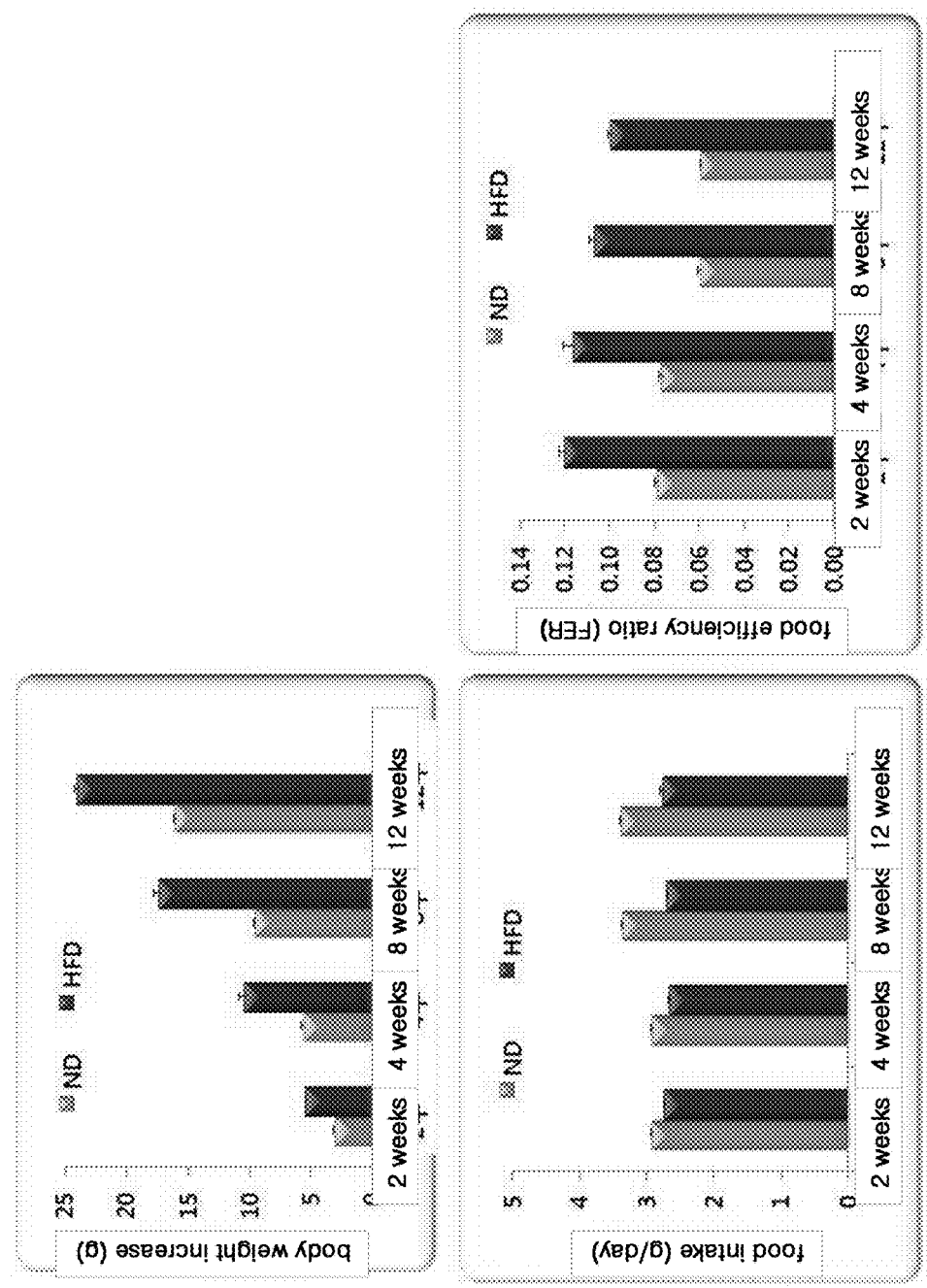
FIG. 1 represents the results of body weight increase, feed intake and food efficiency ratio in mice fed with HFD. Each value is represented as mean±standard error (n=10, p<0.01, *p<0.001).

The food intake, the body weight gain and the food efficiency in the time-course treatment with the HFD (2, 4, 8 and 12 weeks) were measured as shown in FIG. 1. After feeding the test diet for 2, 4, 8 and 12 weeks, each cumulative body weight gain in the HFD group was 24.6±0.2 g/2 wk, 28.2±0.8 g/4 wk, 36.1±0.5 g/8 wk, 41.5±0.6 g/12 wk, respectively. It was significantly increased by 14% (p<0.001), 16% (p<0.01), 18% (p<0.001) and 17% (p<0.001) than that of the ND group (21.2±0.1 g/2 wks, 23.6±0.3 g/4 wk, 29.7±0.4 g/8 wk, 34.3±0.3 g/12 wk), respectively.

Figure 2:
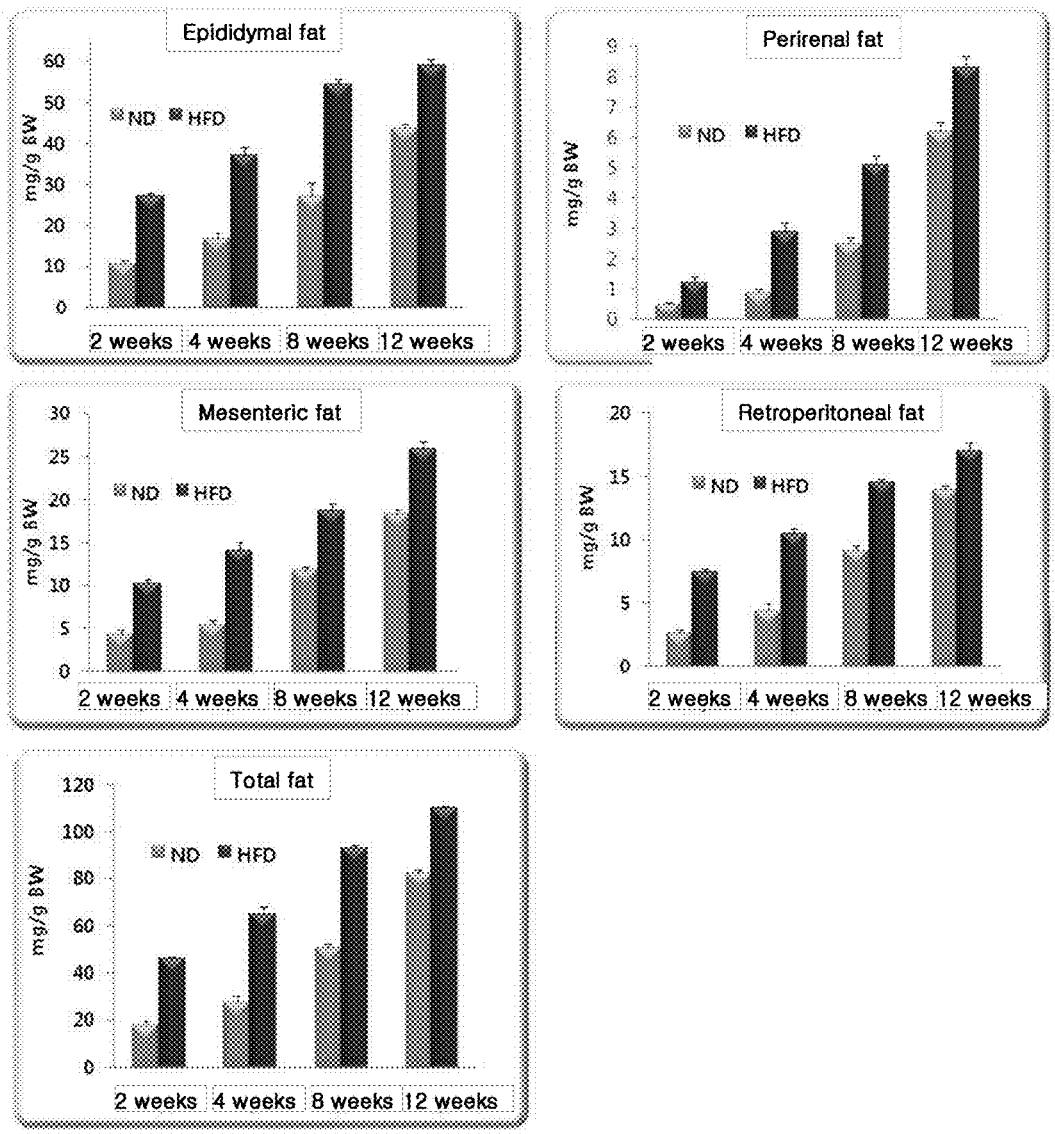
FIG. 2 represents the results of visceral fat-pad weight in mice fed with HFD. Each value is represented as mean±standard error (n=10, *p<0.05).

Increases of the visceral fat weight in the time-course treatment with the HFD (2, 4, 8 and 12 weeks) were measured as shown in FIG. 2. The total visceral fat weight contained epididymal, perirenal, mesenteric and retroperitoneal fat-pads was significantly increased by 151% (2 weeks), 133% (4 weeks), 83% (8 weeks) and 33.6% (12 weeks) than that of the ND group (p<0.05).

3) RNA Extraction and Verification

After adding Trizol agent to visceral fat, subcutaneous fat tissue or muscular tissue, the mixture was homogenized and centrifuged at 12,000×g for 10 min at 4° C. The supernatant was transferred to a new tube to remove fat layer. Then, 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

4) OligoDNA Microarry Analysis

DNA microarry analysis using RNAs of visceral fat, subcutaneous fat tissue and muscular tissue was conducted by GENOCHECK (CO., LTD.). RNA samples were pooled from 10 mice in each experimental group and subjected to microarray experiments in triplicate for the test of reproducibility. NimbleGen Mouse Whole Oligo 12-plex chip used in this experiment was prepared by triplicating 42,576 genes using Mouse Genome Build 8 as database. In NimbleGen mouse Whole Oligo 12-plex chip, 137,090 spots excluded control group gene were spotted by 16 μm×16 μm size in 17.4 mm×13 mm size. 42,576 oligo included 137,145 genes which are known their functions and 5,431 transcripts and EST sequences which are unknown their functions. 10-50 μg of total RNA was added in oligo-dT primer, reverse transcriptase, dNTP, Cy3-dUTP and Cy5-dUTP, and reverse-transcripted according to the kit manufacturer's recommendations. The resultant was purified using cartridge, dried and dissolved in hybridization buffer solution (30 μL). The microarray was placed in hybridization cassette, heated at 95-100° C. for 5 min, mixed independently to each of RNA labeled with Cy3 and Cy5, and hybridized at 45° C. for 18 hrs. The slide was washed twice in solution containing 1×SSC and 0.1% SDS for 5 min, washed in 1×SSC for 5 min and dried to analyze.

5) Types of Olfactory Receptors Expressed in Visceral Fat, Subcutaneous Fat Tissue and Muscular Tissue NimbleGen Mouse Whole Oligo 12-plex chip used in the microarray analysis of this study included total 1,113 different types of olfactory receptor genes. This study was first determined that these 1,113 olfactory receptors were expressed in mouse visceral fat, subcutaneous fat tissue and muscular tissue. Therefore, it was determined that olfactory receptors which have been known to exist in the olfactory epithelium were also found in peripheral tissues.

6) Olfactory Receptor Profile in which the Expression was Changed by Inducing Diet-Induced Obesity A. Verification for the Number of Olfactory Receptor Genes in which the Expression was Changed by More than 2-Fold Change Due to Diet-Induced Obesity As a result of microarray analysis, in visceral fat tissue, the number of whole genes in which the expression was increased or decreased by more than 2-fold change due to high-fat diet were 3,812 (2 weeks), 3,296 (4 weeks), 2,098 (8 weeks) and 1,917 (12 weeks). Among them, the number of olfactory receptor genes in which the expression was increased or decreased by more than 2-fold change were 472 (2 weeks), 604 (4 weeks), 366 (8 weeks) and 549 (12 weeks).

In subcutaneous fat tissue, the number of whole genes in which the expression was increased or decreased by more than 2-fold change due to high-fat diet were 1896 (2 weeks), 2235 (4 weeks), 1649 (8 weeks) and 1316 (12 weeks). Among them, the number of olfactory receptor genes in which the expression was increased or decreased by more than 2-fold change were 129 (2 weeks), 133 (4 weeks), 128 (8 weeks) and 124 (12 weeks).

In muscular tissue, the number of whole genes in which the expression was increased or decreased by more than 2-fold change due to high-fat diet were 885 (2 weeks), 1163 (4 weeks), 830 (8 weeks) and 1115 (12 weeks). Among them, the number of olfactory receptor genes in which the expression was increased or decreased by more than 2-fold change were 79 (2 weeks), 96 (4 weeks), 72 (8 weeks) and 94 (12 weeks) (Table 2).

TABLE 2

The number of olfactory receptor genes in which the expression was changed by more than 2-fold change due to high-fat diet

| | visceral fat | | subcutaneous fat | | muscle | |
|---|---|---|---|---|---|---|
| | The number of olfactory receptor genes in which the expression was changed by more than 2-fold change (n) | The number of whole genes in which the expression was changed by more than 2-fold change (n) | The number of olfactory receptor genes in which the expression was changed by more than 2-fold change (n) | The number of whole genes in which the expression was changed by more than 2-fold change (n) | The number of olfactory receptor genes in which the expression was changed by more than 2-fold change (n) | The number of whole genes in which the expression was changed by more than 2-fold change (n) |
| 2 weeks | 304 | 3,812 | 129 | 1,896 | 79 | 885 |
| 4 weeks | 312 | 3,296 | 133 | 2,235 | 96 | 1,163 |
| 8 weeks | 169 | 2,098 | 128 | 1,649 | 72 | 830 |
| 12 weeks | 167 | 1,917 | 124 | 1,316 | 94 | 1,115 |

B. Verification Using DEG Analysis Method for Profile of Olfactory Receptor Genes in which the Expression was Regulated by Diet-Induced Obesity In visceral fat, subcutaneous fat tissue and muscular tissue of mouse fed the high-fat diet for 2, 4, 8 and 12 weeks, DEG (differentially expressed gene) of olfactory receptor genes in which the expression was changed by more than 2-fold change as compared to the control group was shown in Tables 3-14.

TABLE 3

List of olfactory receptor genes in which the expression was changed by more than 2-fold change due to diet-induced obesity (2 weeks) in visceral fat tissue

| GenBank accession No. | Gene name (Gene symbol) | Expression fold change to HFD group |
|---|---|---|
| NM_146834 | olfactory receptor 101(Olfr101) | 2.7 |
| NM_207149 | olfactory receptor 1010(Olfr1010) | 2.8 |
| NM_001011758 | olfactory receptor 1016(Olfr1016) | 2.9 |
| NM_147015 | olfactory receptor 1019(Olfr1019) | 2.7 |
| NM_001011721 | olfactory receptor 102(Olfr102) | 2.0 |
| NM_146588 | olfactory receptor 1030(Olfr1030) | 2.3 |
| NM_207142 | olfactory receptor 1036(Olfr1036) | 2.3 |
| NM_147013 | olfactory receptor 1038(Olfr1038) | 3.2 |
| NM_001011783 | olfactory receptor 104(Olfr104) | 3.0 |
| NM_207561 | olfactory receptor 1040(Olfr1040) | 2.0 |
| NM_001011777 | olfactory receptor 1042(Olfr1042) | 2.6 |
| NM_146577 | olfactory receptor 1043(Olfr1043) | 4.1 |

TABLE 3-continued

List of olfactory receptor genes in which the expression was changed by more than 2-fold change due to diet-induced obesity (2 weeks) in visceral fat tissue

| GenBank accession No. | Gene name (Gene symbol) | Expression fold change to HFD group |
|---|---|---|
| NM_147010 | olfactory receptor 1052(Olfr1052) | 2.0 |
| NM_146408 | olfactory receptor 1065(Olfr1065) | 2.0 |
| NM_146511 | olfactory receptor 107(Olfr107) | 2.6 |
| NM_146407 | olfactory receptor 1079(Olfr1079) | 2.1 |
| NM_146730 | olfactory receptor 1095(Olfr1095) | 2.5 |
| NM_146542 | olfactory receptor 11(Olfr11) | 2.4 |
| NM_207154 | olfactory receptor 1102(Olfr1102) | 3.8 |
| NM_146752 | olfactory receptor 1106(Olfr1106) | 2.1 |
| NM_146661 | olfactory receptor 1112(Olfr1112) | 3.4 |
| NM_146658 | olfactory receptor 1131(Olfr1131) | 2.1 |
| NM_146351 | olfactory receptor 1133(Olfr1133) | 2.2 |
| NM_146642 | olfactory receptor 1140(Olfr1140) | 2.5 |
| NM_146293 | olfactory receptor 1143(Olfr1143) | 2.2 |
| NM_001011753 | olfactory receptor 115(Olfr115) | 2.0 |
| NM_146817 | olfactory receptor 1156(Olfr1156) | 2.1 |
| NM_146649 | olfactory receptor 1160(Olfr1160) | 2.9 |
| NM_146532 | olfactory receptor 1170(Olfr1170) | 2.7 |
| NM_001011868 | olfactory receptor 1178(Olfr1178) | 3.3 |
| NM_001011816 | olfactory receptor 1181(Olfr1181) | 3.1 |
| NM_001011535 | olfactory receptor 1182(Olfr1182) | 2.5 |
| NM_146823 | olfactory receptor 1184(Olfr1184) | 2.8 |
| NM_146458 | olfactory receptor 1199(Olfr1199) | 2.4 |
| NM_001001810 | olfactory receptor 1206(Olfr1206) | 2.9 |
| NM_146459 | olfactory receptor 1215(Olfr1215) | 2.5 |
| NM_146901 | olfactory receptor 1217(Olfr1217) | 4.1 |
| NM_146899 | olfactory receptor 1219(Olfr1219) | 2.7 |
| NM_146288 | olfactory receptor 122(Olfr122) | 7.3 |
| NM_146891 | olfactory receptor 1225(Olfr1225) | 2.9 |
| NM_146790 | olfactory receptor 1238(Olfr1238) | 3.1 |
| NM_146788 | olfactory receptor 1245(Olfr1245) | 2.4 |
| NM_146476 | olfactory receptor 1254(Olfr1254) | 2.1 |
| NM_146977 | olfactory receptor 1255(Olfr1255) | 2.3 |
| NM_146981 | olfactory receptor 1260(Olfr1260) | 4.4 |
| NM_146342 | olfactory receptor 1269(Olfr1269) | 3.4 |
| NM_146975 | olfactory receptor 1273(Olfr1273) | 3.1 |
| NM_146394 | olfactory receptor 1278(Olfr1278) | 2.3 |
| NM_146908 | olfactory receptor 1280(Olfr1280) | 2.4 |
| NM_207254 | olfactory receptor 1286(Olfr1286) | 3.7 |
| NM_146404 | olfactory receptor 1289(Olfr1289) | 2.3 |
| NM_146885 | olfactory receptor 1294(Olfr1294) | 2.1 |
| NM_146403 | olfactory receptor 1295(Olfr1295) | 2.0 |
| NM_146884 | olfactory receptor 1299(Olfr1299) | 2.2 |
| NM_146652 | olfactory receptor 13(Olfr13) | 2.3 |
| NM_146887 | olfactory receptor 1301(Olfr1301) | 3.2 |
| NM_146889 | olfactory receptor 1302(Olfr1302) | 2.6 |
| NM_001011787 | olfactory receptor 1307(Olfr1307) | 2.1 |
| NM_207151 | olfactory receptor 1308(Olfr1308) | 2.2 |
| NM_146449 | olfactory receptor 1310(Olfr1310) | 2.4 |
| NM_146274 | olfactory receptor 1311(Olfr1311) | 2.5 |
| NM_146292 | olfactory receptor 1324(Olfr1324) | 2.1 |
| NM_207570 | olfactory receptor 1328(Olfr1328) | 4.3 |
| NM_001011870 | olfactory receptor 1329(Olfr1329) | 2.5 |
| NM_207703 | olfactory receptor 1335(Olfr1335) | 2.0 |
| NM_147071 | olfactory receptor 1352(Olfr1352) | 4.1 |
| NM_207571 | olfactory receptor 1355(Olfr1355) | 2.3 |
| NM_146308 | olfactory receptor 1356(Olfr1356) | 2.9 |
| NM_146541 | olfactory receptor 1361(Olfr1361) | 2.3 |
| NM_146283 | olfactory receptor 1366(Olfr1366) | 2.3 |
| NM_146911 | olfactory receptor 1377(Olfr1377) | 2.3 |
| NM_207573 | olfactory receptor 1380(Olfr1380) | 3.3 |
| NM_207574 | olfactory receptor 1383(Olfr1383) | 2.4 |
| NM_001011741 | olfactory receptor 1386(Olfr1386) | 3.3 |
| NM_146473 | olfactory receptor 1387(Olfr1387) | 4.0 |
| NM_147065 | olfactory receptor 1390(Olfr1390) | 2.7 |
| NM_146471 | olfactory receptor 1393(Olfr1393) | 2.2 |
| NM_146276 | olfactory receptor 1394(Olfr1394) | 2.8 |
| NM_146877 | olfactory receptor 1395(Olfr1395) | 3.0 |
| NM_146337 | olfactory receptor 1396(Olfr1396) | 2.6 |
| NM_146275 | olfactory receptor 1402(Olfr1402) | 2.6 |
| NM_146881 | olfactory receptor 1404(Olfr1404) | 2.6 |
| NM_181818 | olfactory receptor 141(Olfr141) | 2.1 |
| NM_146491 | olfactory receptor 1410(Olfr1410) | 2.2 |
| NM_146490 | olfactory receptor 1411(Olfr1411) | 2.3 |
| NM_001011525 | olfactory receptor 1415(Olfr1415) | 2.8 |
| NM_146984 | olfactory receptor 142(Olfr142) | 3.0 |
| NM_001011853 | olfactory receptor 1425(Olfr1425) | 2.2 |
| NM_146806 | olfactory receptor 143(Olfr143) | 3.2 |
| NM_146687 | olfactory receptor 1436(Olfr1436) | 3.1 |
| NM_146683 | olfactory receptor 1441(Olfr1441) | 3.1 |
| NM_146697 | olfactory receptor 1442(Olfr1442) | 2.5 |
| NM_146747 | olfactory receptor 146(Olfr146) | 2.3 |
| NM_001011841 | olfactory receptor 1465(Olfr1465) | 2.6 |
| NM_146869 | olfactory receptor 147(Olfr147) | 3.0 |
| NM_001011842 | olfactory receptor 1474(Olfr1474) | 3.3 |
| NM_146301 | olfactory receptor 1475(Olfr1475) | 4.0 |
| NM_146696 | olfactory receptor 1477(Olfr1477) | 6.8 |
| NM_020513 | olfactory receptor 1508(Olfr1508) | 3.1 |
| NM_146271 | olfactory receptor 1511(Olfr1511) | 2.6 |
| NM_207170 | olfactory receptor 1514(Olfr1514) | 2.2 |
| NM_206823 | olfactory receptor 153(Olfr153) | 2.4 |
| NM_146451 | olfactory receptor 164(Olfr164) | 2.1 |
| NM_146466 | olfactory receptor 165(Olfr165) | 6.9 |
| NM_146935 | olfactory receptor 167(Olfr167) | 3.3 |
| NM_146357 | olfactory receptor 168(Olfr168) | 2.4 |
| NM_146335 | olfactory receptor 19(Olfr19) | 4.1 |
| NM_146484 | olfactory receptor 197(Olfr197) | 2.9 |
| NM_001011808 | olfactory receptor 198(Olfr198) | 2.8 |
| NM_207550 | olfactory receptor 199(Olfr199) | 5.4 |
| NM_146429 | olfactory receptor 223(Olfr223) | 3.7 |
| NM_146405 | olfactory receptor 228(Olfr228) | 2.5 |
| NM_146606 | olfactory receptor 24(Olfr24) | 3.7 |
| NM_207553 | olfactory receptor 251(Olfr251) | 2.1 |
| NM_146688 | olfactory receptor 262(Olfr262) | 2.0 |
| NM_146489 | olfactory receptor 266(Olfr266) | 2.7 |
| NM_146824 | olfactory receptor 273(Olfr273) | 2.2 |
| NM_146280 | olfactory receptor 281(Olfr281) | 2.6 |
| NM_146457 | olfactory receptor 282(Olfr282) | 2.7 |
| NM_147036 | olfactory receptor 283(Olfr283) | 2.6 |
| NM_146281 | olfactory receptor 284(Olfr284) | 2.9 |
| NM_206903 | olfactory receptor 3(Olfr3) | 2.4 |
| NM_146878 | olfactory receptor 30(Olfr30) | 4.7 |
| NM_001011866 | olfactory receptor 309(Olfr309) | 2.7 |
| NM_001011770 | olfactory receptor 332(Olfr332) | 2.8 |
| NM_146947 | olfactory receptor 338(Olfr338) | 3.6 |
| NM_146949 | olfactory receptor 339(Olfr339) | 2.5 |
| NM_146628 | olfactory receptor 344(Olfr344) | 2.7 |
| NM_146940 | olfactory receptor 352(Olfr352) | 2.2 |
| NM_146941 | olfactory receptor 353(Olfr353) | 3.3 |
| NM_146625 | olfactory receptor 355(Olfr355) | 2.5 |
| NM_146624 | olfactory receptor 356(Olfr356) | 3.5 |
| NM_207235 | olfactory receptor 358(Olfr358) | 4.0 |
| NM_147051 | olfactory receptor 362(Olfr362) | 2.4 |
| NM_207555 | olfactory receptor 372(Olfr372) | 2.2 |
| NM_147023 | olfactory receptor 385(Olfr385) | 2.4 |
| NM_207224 | olfactory receptor 386(Olfr386) | 2.4 |
| NM_146825 | olfactory receptor 39(Olfr39) | 2.4 |
| NM_146347 | olfactory receptor 390(Olfr390) | 3.5 |
| NM_147006 | olfactory receptor 392(Olfr392) | 2.1 |
| NM_147008 | olfactory receptor 393(Olfr393) | 5.0 |
| NM_146706 | olfactory receptor 401(Olfr401) | 2.4 |
| NM_146709 | olfactory receptor 411(Olfr411) | 3.4 |
| NM_146715 | olfactory receptor 419(Olfr419) | 2.1 |
| NM_146722 | olfactory receptor 429(Olfr429) | 2.9 |
| NM_146717 | olfactory receptor 433(Olfr433) | 2.1 |
| NM_146655 | olfactory receptor 441(Olfr441) | 2.4 |
| NM_146273 | olfactory receptor 448(Olfr448) | 3.8 |
| NM_146576 | olfactory receptor 459(Olfr459) | 3.7 |
| NM_001005488 | olfactory receptor 467(Olfr467) | 4.0 |
| NM_146426 | olfactory receptor 469(Olfr469) | 7.8 |
| NM_146370 | olfactory receptor 47(Olfr47) | 2.3 |
| XM_891283 | olfactory receptor 471(Olfr471) | 3.0 |
| NM_146775 | olfactory receptor 473(Olfr473) | 2.2 |
| NM_146734 | olfactory receptor 478(Olfr478) | 2.8 |
| NM_146733 | olfactory receptor 482(Olfr482) | 3.9 |

TABLE 3-continued

List of olfactory receptor genes in which the expression was changed by more than 2-fold change due to diet-induced obesity (2 weeks) in visceral fat tissue

| GenBank accession No. | Gene name (Gene symbol) | Expression fold change to HFD group |
|---|---|---|
| NM_146737 | olfactory receptor 494(Olfr494) | 3.0 |
| NM_146307 | olfactory receptor 498(Olfr498) | 2.3 |
| NM_146952 | olfactory receptor 522(Olfr522) | 5.2 |
| NM_146518 | olfactory receptor 523(Olfr523) | 2.5 |
| NM_001011814 | olfactory receptor 524(Olfr524) | 2.4 |
| NM_001011815 | olfactory receptor 533(Olfr533) | 3.2 |
| NM_146962 | olfactory receptor 541(Olfr541) | 2.3 |
| NM_001011782 | olfactory receptor 543(Olfr543) | 2.1 |
| NM_147101 | olfactory receptor 549(Olfr549) | 2.8 |
| NM_207621 | olfactory receptor 553(Olfr553) | 2.4 |
| NM_147103 | olfactory receptor 555(Olfr555) | 2.2 |
| NM_146359 | olfactory receptor 564(Olfr564) | 2.5 |
| NM_147109 | olfactory receptor 577(Olfr577) | 2.3 |
| NM_147115 | olfactory receptor 578(Olfr578) | 4.7 |
| NM_147111 | olfactory receptor 586(Olfr586) | 6.1 |
| NM_207556 | olfactory receptor 592(Olfr592) | 2.1 |
| NM_146731 | olfactory receptor 599(Olfr599) | 2.3 |
| NM_146955 | olfactory receptor 60(Olfr60) | 2.4 |
| NM_146841 | olfactory receptor 617(Olfr617) | 2.8 |
| NM_146812 | olfactory receptor 620(Olfr620) | 3.5 |
| NM_147119 | olfactory receptor 632(Olfr632) | 2.5 |
| NM_147072 | olfactory receptor 641(Olfr641) | 2.5 |
| NM_146329 | olfactory receptor 642(Olfr642) | 3.2 |
| NM_147077 | olfactory receptor 643(Olfr643) | 3.4 |
| NM_207144 | olfactory receptor 645(Olfr645) | 3.3 |
| NM_147056 | olfactory receptor 646(Olfr646) | 2.3 |
| NM_001011757 | olfactory receptor 663(Olfr663) | 2.4 |
| XM_993242 | olfactory receptor 664(Olfr664) | 2.2 |
| NM_147096 | olfactory receptor 666(Olfr666) | 2.1 |
| NM_147060 | olfactory receptor 667(Olfr667) | 2.8 |
| NM_147059 | olfactory receptor 668(Olfr668) | 3.9 |
| NM_147043 | olfactory receptor 669(Olfr669) | 3.3 |
| NM_146760 | olfactory receptor 672(Olfr672) | 3.1 |
| NM_001011848 | olfactory receptor 675(Olfr675) | 2.5 |
| NM_147095 | olfactory receptor 676(Olfr676) | 2.3 |
| NM_146358 | olfactory receptor 677(Olfr677) | 2.0 |
| NM_013620 | olfactory receptor 68(Olfr68) | 3.1 |
| NM_147069 | olfactory receptor 686(Olfr686) | 3.1 |
| NM_146598 | olfactory receptor 695(Olfr695) | 3.7 |
| NM_146599 | olfactory receptor 697(Olfr697) | 2.3 |
| NM_001011749 | olfactory receptor 704(Olfr704) | 2.2 |
| NM_001011542 | olfactory receptor 708(Olfr708) | 2.3 |
| NM_019486 | olfactory receptor 71(Olfr71) | 2.6 |
| NM_147033 | olfactory receptor 714(Olfr714) | 3.9 |
| NM_146780 | olfactory receptor 715(Olfr715) | 2.2 |
| NM_146316 | olfactory receptor 726(Olfr726) | 3.6 |
| NM_146319 | olfactory receptor 727(Olfr727) | 4.1 |
| NM_001011809 | olfactory receptor 728(Olfr728) | 2.1 |
| NM_146493 | olfactory receptor 730(Olfr730) | 2.7 |
| NM_146363 | olfactory receptor 731(Olfr731) | 4.5 |
| NM_146667 | olfactory receptor 740(Olfr740) | 2.7 |
| NM_207133 | olfactory receptor 741(Olfr741) | 2.4 |
| NM_146299 | olfactory receptor 745(Olfr745) | 2.2 |
| NM_207156 | olfactory receptor 747(Olfr747) | 3.6 |
| NM_001011829 | olfactory receptor 761(Olfr761) | 5.2 |
| NM_146422 | olfactory receptor 767(Olfr767) | 2.9 |
| NM_146864 | olfactory receptor 768(Olfr768) | 6.9 |
| NM_146863 | olfactory receptor 770(Olfr770) | 3.0 |
| NM_146547 | olfactory receptor 771(Olfr771) | 2.8 |
| NM_146266 | olfactory receptor 772(Olfr772) | 5.6 |
| NM_207008 | olfactory receptor 773(Olfr773-ps) | 2.2 |
| NM_207620 | olfactory receptor 774(Olfr774) | 2.0 |
| NM_207559 | olfactory receptor 776(Olfr776) | 2.5 |
| NM_001011849 | olfactory receptor 792(Olfr792) | 7.2 |
| NM_146548 | olfactory receptor 800(Olfr800) | 3.9 |
| NM_001011821 | olfactory receptor 804(Olfr804) | 2.0 |
| NM_146550 | olfactory receptor 810(Olfr810) | 4.1 |
| NM_207159 | olfactory receptor 814(Olfr814) | 2.2 |
| NM_146670 | olfactory receptor 815(Olfr815) | 2.2 |
| NM_146677 | olfactory receptor 825(Olfr825) | 2.1 |
| NM_146676 | olfactory receptor 826(Olfr826) | 2.3 |
| NM_146300 | olfactory receptor 827(Olfr827) | 2.4 |
| NM_146567 | olfactory receptor 843(Olfr843) | 2.6 |
| NM_146282 | olfactory receptor 846(Olfr846) | 2.4 |
| NM_146525 | olfactory receptor 847(Olfr847) | 2.3 |
| NM_146524 | olfactory receptor 855(Olfr855) | 3.6 |
| NM_146558 | olfactory receptor 866(Olfr866) | 2.3 |
| NM_146903 | olfactory receptor 871(Olfr871) | 2.5 |
| NM_146882 | olfactory receptor 874(Olfr874) | 4.6 |
| NM_146749 | olfactory receptor 875(Olfr875) | 2.0 |
| NM_146883 | olfactory receptor 876(Olfr876) | 2.2 |
| NM_146417 | olfactory receptor 877(Olfr877) | 3.5 |
| NM_001011739 | olfactory receptor 885(Olfr885) | 2.2 |
| NM_146336 | olfactory receptor 893(Olfr893) | 2.6 |
| NM_146801 | olfactory receptor 904(Olfr904) | 2.3 |
| NM_146872 | olfactory receptor 908(Olfr908) | 3.3 |
| NM_146811 | olfactory receptor 910(Olfr910) | 3.0 |
| NM_146810 | olfactory receptor 912(Olfr912) | 6.4 |
| NM_001011864 | olfactory receptor 917(Olfr917) | 2.1 |
| NM_146782 | olfactory receptor 921(Olfr921) | 3.4 |
| NM_146441 | olfactory receptor 933(Olfr933) | 2.6 |
| NM_146442 | olfactory receptor 934(Olfr934) | 2.0 |
| NM_001011518 | olfactory receptor 94(Olfr94) | 2.5 |
| NM_146503 | olfactory receptor 952(Olfr952) | 2.0 |
| NM_146330 | olfactory receptor 958(Olfr958) | 2.1 |
| NM_146279 | olfactory receptor 960(Olfr960) | 2.4 |
| NM_146612 | olfactory receptor 968(Olfr968) | 2.1 |
| NM_146826 | olfactory receptor 969(Olfr969) | 2.2 |
| NM_147107 | olfactory receptor 974(Olfr974) | 2.4 |
| NM_147105 | olfactory receptor 978(Olfr978) | 3.0 |
| NM_146510 | olfactory receptor 98(Olfr98) | 2.8 |
| NM_146286 | olfactory receptor 981(Olfr981) | 2.9 |
| NM_146855 | olfactory receptor 985(Olfr985) | 2.2 |

TABLE 4

List of olfactory receptor genes in which the expression was changed by more than 2-fold change due to diet-induced obesity (4 weeks) in visceral fat tissue

| GenBank accession No. | Gene name (Gene symbol) | Expression fold change to HFD group |
|---|---|---|
| NM_207673 | olfactory receptor 100(Olfr100) | 5.4 |
| NM_001011695 | olfactory receptor 1000(Olfr1000) | 2.2 |
| NM_146866 | olfactory receptor 1008(Olfr1008) | 2.7 |
| NM_207149 | olfactory receptor 1010(Olfr1010) | 2.2 |
| NM_001011758 | olfactory receptor 1016(Olfr1016) | 2.5 |
| NM_147015 | olfactory receptor 1019(Olfr1019) | 3.8 |
| NM_146588 | olfactory receptor 1030(Olfr1030) | 2.1 |
| NM_001011872 | olfactory receptor 1034(Olfr1034) | 2.1 |
| NM_001011783 | olfactory receptor 104(Olfr104) | 4.1 |
| NM_207561 | olfactory receptor 1040(Olfr1040) | 2.6 |
| NM_001011777 | olfactory receptor 1042(Olfr1042) | 2.0 |
| NM_146577 | olfactory receptor 1043(Olfr1043) | 2.2 |
| NM_147012 | olfactory receptor 1047(Olfr1047) | 2.1 |
| NM_147010 | olfactory receptor 1052(Olfr1052) | 7.2 |
| NM_146391 | olfactory receptor 1058(Olfr1058) | 4.5 |
| NM_146408 | olfactory receptor 1065(Olfr1065) | 3.4 |
| NM_001011735 | olfactory receptor 1066(Olfr1066) | 2.4 |
| NM_146511 | olfactory receptor 107(Olfr107) | 2.5 |
| NM_207135 | olfactory receptor 1084(Olfr1084) | 2.6 |
| NM_146843 | olfactory receptor 1097(Olfr1097) | 2.3 |
| NM_146542 | olfactory receptor 11(Olfr11) | 4.1 |
| NM_146594 | olfactory receptor 1100(Olfr1100) | 2.9 |
| NM_146752 | olfactory receptor 1106(Olfr1106) | 4.6 |
| NM_146661 | olfactory receptor 1112(Olfr1112) | 2.4 |
| NM_207632 | olfactory receptor 1118(Olfr1118) | 2.2 |
| NM_146348 | olfactory receptor 1121(Olfr1121) | 3.2 |
| NM_146351 | olfactory receptor 1133(Olfr1133) | 2.1 |

TABLE 4-continued

List of olfactory receptor genes in which the expression was changed by more than 2-fold change due to diet-induced obesity (4 weeks) in visceral fat tissue

| GenBank accession No. | Gene name (Gene symbol) | Expression fold change to HFD group |
|---|---|---|
| NM_146293 | olfactory receptor 1143(Olfr1143) | 2.2 |
| NM_001011753 | olfactory receptor 115(Olfr115) | 2.3 |
| NM_146645 | olfactory receptor 1158(Olfr1158) | 2.2 |
| NM_146641 | olfactory receptor 1164(Olfr1164) | 2.7 |
| NM_146294 | olfactory receptor 1167(Olfr1167) | 2.0 |
| XM_621554 | olfactory receptor 1174(Olfr1174) | 2.8 |
| XM_621555 | olfactory receptor 1175(Olfr1175) | 3.4 |
| NM_001011868 | olfactory receptor 1178(Olfr1178) | 4.1 |
| NM_001011816 | olfactory receptor 1181(Olfr1181) | 5.5 |
| NM_001011535 | olfactory receptor 1182(Olfr1182) | 3.2 |
| NM_146823 | olfactory receptor 1184(Olfr1184) | 2.4 |
| NM_146458 | olfactory receptor 1199(Olfr1199) | 3.5 |
| NM_146895 | olfactory receptor 1201(Olfr1201) | 2.8 |
| NM_146778 | olfactory receptor 1208(Olfr1208) | 2.3 |
| NM_146459 | olfactory receptor 1215(Olfr1215) | 2.1 |
| NM_146901 | olfactory receptor 1217(Olfr1217) | 3.5 |
| NM_146899 | olfactory receptor 1219(Olfr1219) | 3.2 |
| NM_146288 | olfactory receptor 122(Olfr122) | 2.2 |
| NM_146789 | olfactory receptor 1230(Olfr1230) | 2.0 |
| NM_146790 | olfactory receptor 1238(Olfr1238) | 2.2 |
| NM_146970 | olfactory receptor 1239(Olfr1239) | 2.5 |
| NM_146983 | olfactory receptor 1256(Olfr1256) | 2.0 |
| NM_146341 | olfactory receptor 1259(Olfr1259) | 2.7 |
| NM_146981 | olfactory receptor 1260(Olfr1260) | 2.0 |
| NM_146794 | olfactory receptor 1263(Olfr1263) | 2.7 |
| NM_146377 | olfactory receptor 127(Olfr127) | 2.3 |
| NM_146985 | olfactory receptor 1270(Olfr1270) | 2.3 |
| NM_146975 | olfactory receptor 1273(Olfr1273) | 2.5 |
| NM_146394 | olfactory receptor 1278(Olfr1278) | 3.1 |
| NM_206816 | olfactory receptor 128(Olfr128) | 2.3 |
| NM_146908 | olfactory receptor 1280(Olfr1280) | 3.0 |
| NM_001005568 | olfactory receptor 1281(Olfr1281) | 2.1 |
| NM_207254 | olfactory receptor 1286(Olfr1286) | 3.1 |
| NM_146400 | olfactory receptor 1288(Olfr1288) | 2.8 |
| XM_888068 | olfactory receptor 1293(Olfr1293) | 2.6 |
| NM_146885 | olfactory receptor 1294(Olfr1294) | 3.0 |
| NM_146403 | olfactory receptor 1295(Olfr1295) | 3.3 |
| NM_146886 | olfactory receptor 1298(Olfr1298) | 2.4 |
| NM_146884 | olfactory receptor 1299(Olfr1299) | 3.1 |
| NM_146652 | olfactory receptor 13(Olfr13) | 3.9 |
| NM_146889 | olfactory receptor 1302(Olfr1302) | 4.0 |
| NM_001011787 | olfactory receptor 1307(Olfr1307) | 2.9 |
| NM_207151 | olfactory receptor 1308(Olfr1308) | 3.1 |
| NM_146450 | olfactory receptor 1314(Olfr1314) | 3.3 |
| NM_146292 | olfactory receptor 1324(Olfr1324) | 3.1 |
| NM_207570 | olfactory receptor 1328(Olfr1328) | 3.4 |
| NM_001011870 | olfactory receptor 1329(Olfr1329) | 3.5 |
| NM_146831 | olfactory receptor 133(Olfr133) | 3.5 |
| NM_146385 | olfactory receptor 1347(Olfr1347) | 2.7 |
| NM_147040 | olfactory receptor 1351(Olfr1351) | 2.5 |
| NM_147071 | olfactory receptor 1352(Olfr1352) | 3.0 |
| NM_207571 | olfactory receptor 1355(Olfr1355) | 2.8 |
| NM_001011737 | olfactory receptor 1357(Olfr1357) | 2.7 |
| NM_146541 | olfactory receptor 1361(Olfr1361) | 3.5 |
| NM_146744 | olfactory receptor 1362(Olfr1362) | 2.1 |
| NM_146540 | olfactory receptor 1364(Olfr1364) | 2.4 |
| NM_146534 | olfactory receptor 1368(Olfr1368) | 3.2 |
| NM_146488 | olfactory receptor 137(Olfr137) | 2.2 |
| NM_146910 | olfactory receptor 1378(Olfr1378) | 2.6 |
| NM_207573 | olfactory receptor 1380(Olfr1380) | 2.5 |
| NM_001011790 | olfactory receptor 1382(Olfr1382) | 2.1 |
| NM_146473 | olfactory receptor 1387(Olfr1387) | 3.8 |
| NM_146467 | olfactory receptor 1388(Olfr1388) | 3.2 |
| NM_146468 | olfactory receptor 1391(Olfr1391) | 2.4 |
| NM_146470 | olfactory receptor 1392(Olfr1392) | 2.3 |
| NM_146471 | olfactory receptor 1393(Olfr1393) | 2.6 |
| NM_146276 | olfactory receptor 1394(Olfr1394) | 2.5 |
| NM_146877 | olfactory receptor 1395(Olfr1395) | 2.4 |
| NM_146651 | olfactory receptor 1403(Olfr1403) | 2.3 |
| NM_146881 | olfactory receptor 1404(Olfr1404) | 3.0 |
| NM_181818 | olfactory receptor 141(Olfr141) | 2.4 |
| NM_146491 | olfactory receptor 1410(Olfr1410) | 2.0 |
| NM_146490 | olfactory receptor 1411(Olfr1411) | 3.6 |
| NM_001011525 | olfactory receptor 1415(Olfr1415) | 3.9 |
| NM_146984 | olfactory receptor 142(Olfr142) | 2.9 |
| NM_146809 | olfactory receptor 1426(Olfr1426) | 2.9 |
| NM_146806 | olfactory receptor 143(Olfr143) | 2.3 |
| NM_146687 | olfactory receptor 1436(Olfr1436) | 2.2 |
| NM_001011839 | olfactory receptor 1437(Olfr1437) | 3.3 |
| NM_146684 | olfactory receptor 1440(Olfr1440) | 2.0 |
| NM_146371 | olfactory receptor 1450(Olfr1450) | 3.0 |
| NM_146747 | olfactory receptor 146(Olfr146) | 6.6 |
| NM_146869 | olfactory receptor 147(Olfr147) | 2.1 |
| NM_146301 | olfactory receptor 1475(Olfr1475) | 4.3 |
| NM_146696 | olfactory receptor 1477(Olfr1477) | 6.0 |
| NM_207575 | olfactory receptor 1480(Olfr1480) | 2.3 |
| NM_146291 | olfactory receptor 1484(Olfr1484) | 2.7 |
| NM_207138 | olfactory receptor 149(Olfr149) | 6.4 |
| NM_020513 | olfactory receptor 1508(Olfr1508) | 2.3 |
| NM_020514 | olfactory receptor 1509(Olfr1509) | 2.3 |
| NM_146585 | olfactory receptor 1517(Olfr1517) | 2.7 |
| NM_206823 | olfactory receptor 153(Olfr153) | 2.1 |
| NM_008763 | olfactory receptor 16(Olfr16) | 2.3 |
| NM_146451 | olfactory receptor 164(Olfr164) | 4.0 |
| NM_146466 | olfactory receptor 165(Olfr165) | 4.0 |
| NM_147068 | olfactory receptor 166(Olfr166) | 2.1 |
| NM_146935 | olfactory receptor 167(Olfr167) | 2.3 |
| NM_146357 | olfactory receptor 168(Olfr168) | 2.2 |
| NM_001011855 | olfactory receptor 169(Olfr169) | 2.5 |
| NM_146957 | olfactory receptor 170(Olfr170) | 3.4 |
| NM_146993 | olfactory receptor 176(Olfr176) | 2.7 |
| NM_146999 | olfactory receptor 181(Olfr181) | 2.3 |
| NM_146484 | olfactory receptor 197(Olfr197) | 3.4 |
| NM_207550 | olfactory receptor 199(Olfr199) | 2.8 |
| NM_146912 | olfactory receptor 211(Olfr211) | 2.2 |
| NM_146405 | olfactory receptor 228(Olfr228) | 2.5 |
| NM_010970 | olfactory receptor 23(Olfr23) | 2.3 |
| NM_146606 | olfactory receptor 24(Olfr24) | 2.3 |
| NM_010974 | olfactory receptor 242(Olfr242) | 2.2 |
| NM_001005520 | olfactory receptor 244(Olfr244) | 2.5 |
| NM_146269 | olfactory receptor 247(Olfr247) | 2.2 |
| NM_146870 | olfactory receptor 25(Olfr25) | 4.0 |
| NM_207552 | olfactory receptor 250(Olfr250) | 2.4 |
| NM_001005780 | olfactory receptor 255(Olfr255) | 2.4 |
| NM_146489 | olfactory receptor 266(Olfr266) | 3.5 |
| NM_146829 | olfactory receptor 27(Olfr27) | 2.6 |
| NM_146280 | olfactory receptor 281(Olfr281) | 3.0 |
| NM_146457 | olfactory receptor 282(Olfr282) | 2.7 |
| NM_146281 | olfactory receptor 284(Olfr284) | 4.1 |
| NM_001011767 | olfactory receptor 299(Olfr299) | 3.2 |
| NM_146878 | olfactory receptor 30(Olfr30) | 2.0 |
| NM_146536 | olfactory receptor 313(Olfr313) | 4.1 |
| NM_146500 | olfactory receptor 319(Olfr319) | 2.5 |
| NM_146947 | olfactory receptor 338(Olfr338) | 3.8 |
| NM_146948 | olfactory receptor 342(Olfr342) | 2.7 |
| NM_146939 | olfactory receptor 354(Olfr354) | 3.9 |
| NM_146624 | olfactory receptor 356(Olfr356) | 2.7 |
| NM_147051 | olfactory receptor 362(Olfr362) | 2.4 |
| NM_146662 | olfactory receptor 365(Olfr365) | 3.0 |
| XM_619748 | olfactory receptor 367(Olfr367) | 2.2 |
| NM_146825 | olfactory receptor 39(Olfr39) | 2.8 |
| NM_146347 | olfactory receptor 390(Olfr390) | 6.5 |
| NM_147008 | olfactory receptor 393(Olfr393) | 4.2 |
| NM_147007 | olfactory receptor 394(Olfr394) | 2.3 |
| NM_001011863 | olfactory receptor 406(Olfr406) | 3.1 |
| NM_146761 | olfactory receptor 414(Olfr414) | 2.4 |
| NM_146721 | olfactory receptor 424(Olfr424) | 2.4 |
| NM_207158 | olfactory receptor 427(Olfr427) | 2.5 |
| NM_146722 | olfactory receptor 429(Olfr429) | 2.7 |
| NM_146653 | olfactory receptor 435(Olfr435) | 3.1 |
| NM_146655 | olfactory receptor 441(Olfr441) | 4.3 |
| NM_001011869 | olfactory receptor 452(Olfr452) | 4.5 |
| NM_146576 | olfactory receptor 459(Olfr459) | 5.3 |
| NM_001005488 | olfactory receptor 467(Olfr467) | 2.2 |

TABLE 4-continued

List of olfactory receptor genes in which the expression was changed by more than 2-fold change due to diet-induced obesity (4 weeks) in visceral fat tissue

| GenBank accession No. | Gene name (Gene symbol) | Expression fold change to HFD group |
|---|---|---|
| NM_146426 | olfactory receptor 469(Olfr469) | 6.2 |
| NM_146370 | olfactory receptor 47(Olfr47) | 7.0 |
| XM_891283 | olfactory receptor 471(Olfr471) | 3.3 |
| NM_001011810 | olfactory receptor 485(Olfr485) | 4.4 |
| NM_146732 | olfactory receptor 488(Olfr488) | 2.6 |
| NM_146736 | olfactory receptor 491(Olfr491) | 2.6 |
| NM_146737 | olfactory receptor 494(Olfr494) | 2.6 |
| NM_146738 | olfactory receptor 497(Olfr497) | 3.1 |
| NM_146914 | olfactory receptor 5(Olfr5) | 2.6 |
| NM_001011871 | olfactory receptor 506(Olfr506) | 2.7 |
| NM_146725 | olfactory receptor 516(Olfr516) | 3.0 |
| NM_146952 | olfactory receptor 522(Olfr522) | 3.4 |
| NM_146518 | olfactory receptor 523(Olfr523) | 2.6 |
| NM_146956 | olfactory receptor 525(Olfr525) | 2.1 |
| NM_146960 | olfactory receptor 53(Olfr53) | 2.2 |
| NM_001011815 | olfactory receptor 533(Olfr533) | 4.9 |
| NM_010997 | olfactory receptor 54(Olfr54) | 2.0 |
| NM_146840 | olfactory receptor 545(Olfr545) | 2.6 |
| NM_147101 | olfactory receptor 549(Olfr549) | 2.2 |
| NM_207621 | olfactory receptor 553(Olfr553) | 3.5 |
| NM_146325 | olfactory receptor 554(Olfr554) | 3.2 |
| NM_147103 | olfactory receptor 555(Olfr555) | 2.6 |
| NM_147091 | olfactory receptor 568(Olfr568) | 2.1 |
| NM_147085 | olfactory receptor 571(Olfr571) | 2.2 |
| NM_147089 | olfactory receptor 572(Olfr572) | 4.3 |
| NM_147115 | olfactory receptor 578(Olfr578) | 2.2 |
| NM_147111 | olfactory receptor 586(Olfr586) | 4.8 |
| NM_147052 | olfactory receptor 589(Olfr589) | 2.5 |
| NM_001011847 | olfactory receptor 591(Olfr591) | 2.2 |
| NM_207556 | olfactory receptor 592(Olfr592) | 2.0 |
| NM_146731 | olfactory receptor 599(Olfr599) | 2.3 |
| NM_146727 | olfactory receptor 611(Olfr611) | 3.8 |
| NM_146812 | olfactory receptor 620(Olfr620) | 4.7 |
| NM_147083 | olfactory receptor 622(Olfr622) | 2.3 |
| NM_147055 | olfactory receptor 649(Olfr649) | 2.5 |
| NM_146379 | olfactory receptor 654(Olfr654) | 2.4 |
| XM_993242 | olfactory receptor 664(Olfr664) | 2.2 |
| NM_147096 | olfactory receptor 666(Olfr666) | 2.8 |
| NM_147059 | olfactory receptor 668(Olfr668) | 4.6 |
| NM_147043 | olfactory receptor 669(Olfr669) | 2.9 |
| NM_001011755 | olfactory receptor 671(Olfr671) | 4.3 |
| NM_001011848 | olfactory receptor 675(Olfr675) | 2.5 |
| NM_147095 | olfactory receptor 676(Olfr676) | 4.8 |
| NM_147044 | olfactory receptor 679(Olfr679) | 2.1 |
| NM_013620 | olfactory receptor 68(Olfr68) | 2.5 |
| NM_146598 | olfactory receptor 695(Olfr695) | 2.4 |
| NM_001011862 | olfactory receptor 699(Olfr699) | 2.4 |
| NM_146597 | olfactory receptor 702(Olfr702) | 3.2 |
| NM_001011749 | olfactory receptor 704(Olfr704) | 2.7 |
| NM_019486 | olfactory receptor 71(Olfr71) | 2.2 |
| NM_147035 | olfactory receptor 711(Olfr711) | 2.0 |
| NM_147033 | olfactory receptor 714(Olfr714) | 2.4 |
| NM_146780 | olfactory receptor 715(Olfr715) | 2.7 |
| NM_146604 | olfactory receptor 716(Olfr716) | 2.1 |
| NM_146319 | olfactory receptor 727(Olfr727) | 3.5 |
| NM_001011809 | olfactory receptor 728(Olfr728) | 2.4 |
| NM_146363 | olfactory receptor 731(Olfr731) | 4.4 |
| NM_146664 | olfactory receptor 734(Olfr734) | 2.6 |
| NM_001011754 | olfactory receptor 735(Olfr735) | 2.5 |
| NM_146430 | olfactory receptor 742(Olfr742) | 3.7 |
| NM_207558 | olfactory receptor 750(Olfr750) | 2.3 |
| NM_001011829 | olfactory receptor 761(Olfr761) | 4.0 |
| NM_146422 | olfactory receptor 767(Olfr767) | 2.4 |
| NM_146864 | olfactory receptor 768(Olfr768) | 2.1 |
| NM_146863 | olfactory receptor 770(Olfr770) | 2.7 |
| NM_146547 | olfactory receptor 771(Olfr771) | 3.0 |
| NM_146266 | olfactory receptor 772(Olfr772) | 5.9 |
| NM_207620 | olfactory receptor 774(Olfr774) | 5.4 |
| NM_207559 | olfactory receptor 776(Olfr776) | 2.9 |
| NM_130866 | olfactory receptor 78(Olfr78) | 3.9 |
| NM_146933 | olfactory receptor 790(Olfr790) | 2.9 |
| NM_001011849 | olfactory receptor 792(Olfr792) | 4.2 |
| NM_146548 | olfactory receptor 800(Olfr800) | 2.6 |
| NM_146554 | olfactory receptor 803(Olfr803) | 4.6 |
| NM_146929 | olfactory receptor 807(Olfr807) | 3.2 |
| NM_146550 | olfactory receptor 810(Olfr810) | 2.8 |
| NM_146552 | olfactory receptor 811(Olfr811) | 2.1 |
| NM_207159 | olfactory receptor 814(Olfr814) | 2.5 |
| NM_146670 | olfactory receptor 815(Olfr815) | 3.4 |
| NM_146776 | olfactory receptor 821(Olfr821) | 2.6 |
| NM_146677 | olfactory receptor 825(Olfr825) | 2.4 |
| NM_146300 | olfactory receptor 827(Olfr827) | 2.6 |
| NM_146282 | olfactory receptor 846(Olfr846) | 2.5 |
| NM_146524 | olfactory receptor 855(Olfr855) | 4.1 |
| NM_146526 | olfactory receptor 859(Olfr859) | 2.1 |
| NM_146528 | olfactory receptor 860(Olfr860) | 2.5 |
| NM_146412 | olfactory receptor 464(Olfr464) | 0.5 |
| NM_146310 | olfactory receptor 493(Olfr493) | 0.5 |

TABLE 5

List of olfactory receptor genes in which the expression was changed by more than 2-fold change due to diet-induced obesity (8 weeks) in visceral fat tissue

| GenBank accession No. | Gene name (Gene symbol) | Expression fold change to HFD group |
|---|---|---|
| NM_001011695 | olfactory receptor1000(Olfr1000) | 2.5 |
| NM_146571 | olfactory receptor1015(Olfr1015) | 2.9 |
| NM_001011758 | olfactory receptor1016(Olfr1016) | 2.2 |
| NM_146587 | olfactory receptor1023(Olfr1023) | 2.3 |
| NM_207562 | olfactory receptor1051(Olfr1051) | 2.1 |
| NM_146592 | olfactory receptor1086(Olfr1086) | 2.4 |
| NM_001011825 | olfactory receptor1105(Olfr1105) | 2.7 |
| NM_146752 | olfactory receptor1106(Olfr1106) | 2.2 |
| NM_146661 | olfactory receptor1112(Olfr1112) | 3.0 |
| NM_146658 | olfactory receptor1131(Olfr1131) | 2.2 |
| NM_146836 | olfactory receptor1132(Olfr1132) | 2.2 |
| NM_146293 | olfactory receptor1143(Olfr1143) | 2.2 |
| NM_146645 | olfactory receptor1158(Olfr1158) | 3.0 |
| NM_146531 | olfactory receptor1168(Olfr1168) | 2.0 |
| NM_001011868 | olfactory receptor1178(Olfr1178) | 3.1 |
| NM_001011816 | olfactory receptor1181(Olfr1181) | 2.9 |
| NM_146778 | olfactory receptor1208(Olfr1208) | 2.0 |
| NM_146901 | olfactory receptor1217(Olfr1217) | 2.1 |
| NM_146288 | olfactory receptor 122(Olfr122) | 2.0 |
| NM_146891 | olfactory receptor1225(Olfr1225) | 2.0 |
| NM_146789 | olfactory receptor1230(Olfr1230) | 2.6 |
| NM_146788 | olfactory receptor1245(Olfr1245) | 2.1 |
| NM_146400 | olfactory receptor1288(Olfr1288) | 2.3 |
| NM_146652 | olfactory receptor 13(Olfr13) | 6.2 |
| NM_146402 | olfactory receptor1303(Olfr1303) | 2.2 |
| NM_146362 | olfactory receptor1312(Olfr1312) | 2.9 |
| NM_146292 | olfactory receptor1324(Olfr1324) | 2.5 |
| NM_146831 | olfactory receptor 133(Olfr133) | 2.8 |
| NM_147040 | olfactory receptor1351(Olfr1351) | 2.5 |
| NM_147071 | olfactory receptor1352(Olfr1352) | 3.3 |
| NM_207571 | olfactory receptor1355(Olfr1355) | 4.2 |
| NM_207573 | olfactory receptor1380(Olfr1380) | 2.6 |
| NM_146473 | olfactory receptor1387(Olfr1387) | 2.1 |
| NM_146468 | olfactory receptor1391(Olfr1391) | 2.6 |
| NM_020515 | olfactory receptor 140(Olfr140) | 2.0 |
| NM_146881 | olfactory receptor1404(Olfr1404) | 2.2 |
| NM_181818 | olfactory receptor141(Olfr141) | 3.1 |
| NM_146490 | olfactory receptor1411(Olfr1411) | 2.1 |
| NM_146301 | olfactory receptor1475(Olfr1475) | 2.4 |
| NM_146696 | olfactory receptor1477(Olfr1477) | 2.3 |
| NM_146635 | olfactory receptor1489(Olfr1489) | 3.0 |
| NM_207138 | olfactory receptor 149(Olfr149) | 3.2 |

TABLE 5-continued

List of olfactory receptor genes in which the expression was changed by more than 2-fold change due to diet-induced obesity (8 weeks) in visceral fat tissue

| GenBank accession No. | Gene name (Gene symbol) | Expression fold change to HFD group |
|---|---|---|
| NM_146990 | olfactory receptor1494(Olfr1494) | 2.3 |
| NM_020513 | olfactory receptor1508(Olfr1508) | 2.1 |
| NM_146646 | olfactory receptor 152(Olfr152) | 2.2 |
| NM_008763 | olfactory receptor 16(Olfr16) | 2.1 |
| NM_146466 | olfactory receptor 165(Olfr165) | 4.1 |
| NM_146997 | olfactory receptor 178(Olfr178) | 3.2 |
| NM_146999 | olfactory receptor 181(Olfr181) | 3.7 |
| NM_146485 | olfactory receptor 183(Olfr183) | 2.0 |
| NM_207553 | olfactory receptor 251(Olfr251) | 2.2 |
| NM_146457 | olfactory receptor 282(Olfr282) | 2.2 |
| NM_147036 | olfactory receptor 283(Olfr283) | 2.8 |
| NM_146878 | olfactory receptor 30(Olfr30) | 3.0 |
| NM_001011866 | olfactory receptor 309(Olfr309) | 2.2 |
| NM_146536 | olfactory receptor 313(Olfr313) | 3.2 |
| NM_010980 | olfactory receptor 32(Olfr32) | 2.6 |
| NM_146951 | olfactory receptor 340(Olfr340) | 2.7 |
| NM_146948 | olfactory receptor 342(Olfr342) | 2.4 |
| NM_146939 | olfactory receptor 354(Olfr354) | 3.0 |
| NM_146623 | olfactory receptor 357(Olfr357) | 2.1 |
| NM_207235 | olfactory receptor 358(Olfr358) | 2.1 |
| NM_146662 | olfactory receptor 365(Olfr365) | 2.6 |
| NM_146338 | olfactory receptor 374(Olfr374) | 2.8 |
| NM_146825 | olfactory receptor 39(Olfr39) | 2.2 |
| NM_147008 | olfactory receptor 393(Olfr393) | 2.1 |
| NM_146706 | olfactory receptor 401(Olfr401) | 2.7 |
| NM_146305 | olfactory receptor 420(Olfr420) | 2.3 |
| NM_146830 | olfactory receptor 44(Olfr44) | 3.1 |
| NM_146576 | olfactory receptor 459(Olfr459) | 2.7 |
| NM_146370 | olfactory receptor 47(Olfr47) | 2.2 |
| NM_146774 | olfactory receptor 472(Olfr472) | 2.6 |
| NM_146307 | olfactory receptor 498(Olfr498) | 2.0 |
| NM_146914 | olfactory receptor 5(Olfr5) | 2.0 |
| NM_146952 | olfactory receptor 522(Olfr522) | 2.3 |
| NM_146956 | olfactory receptor 525(Olfr525) | 3.7 |
| NM_146960 | olfactory receptor 53(Olfr53) | 3.6 |
| NM_010998 | olfactory receptor 55(Olfr55) | 2.4 |
| NM_146755 | olfactory receptor 551(Olfr551) | 2.5 |
| NM_207621 | olfactory receptor 553(Olfr553) | 2.1 |
| NM_147089 | olfactory receptor 572(Olfr572) | 4.2 |
| NM_147109 | olfactory receptor 577(Olfr577) | 3.1 |
| NM_207143 | olfactory receptor 594(Olfr594) | 4.4 |
| NM_147094 | olfactory receptor 606(Olfr606) | 2.3 |
| NM_147076 | olfactory receptor 619(Olfr619) | 2.3 |
| NM_146315 | olfactory receptor 62(Olfr62) | 2.1 |
| NM_146379 | olfactory receptor 654(Olfr654) | 2.8 |
| NM_147059 | olfactory receptor 668(Olfr668) | 3.3 |
| NM_207146 | olfactory receptor 670(Olfr670) | 2.4 |
| NM_146758 | olfactory receptor 678(Olfr678) | 3.6 |
| NM_146596 | olfactory receptor 703(Olfr703) | 2.4 |
| NM_147033 | olfactory receptor 714(Olfr714) | 2.3 |
| NM_146780 | olfactory receptor 715(Olfr715) | 3.0 |
| NM_146316 | olfactory receptor 726(Olfr726) | 2.6 |
| NM_146493 | olfactory receptor 730(Olfr730) | 3.4 |
| NM_207558 | olfactory receptor 750(Olfr750) | 2.7 |
| NM_146266 | olfactory receptor 772(Olfr772) | 3.6 |
| NM_207620 | olfactory receptor 774(Olfr774) | 3.0 |
| NM_001011849 | olfactory receptor 792(Olfr792) | 2.3 |
| NM_146550 | olfactory receptor 810(Olfr810) | 2.6 |
| NM_146528 | olfactory receptor 860(Olfr860) | 2.3 |
| NM_146882 | olfactory receptor 874(Olfr874) | 3.3 |
| NM_146883 | olfactory receptor 876(Olfr876) | 2.1 |
| NM_146417 | olfactory receptor 877(Olfr877) | 2.3 |
| NM_001011739 | olfactory receptor 885(Olfr885) | 2.4 |
| NM_146478 | olfactory receptor 891(Olfr891) | 2.1 |
| NM_146479 | olfactory receptor 899(Olfr899) | 2.1 |
| NM_146785 | olfactory receptor 915(Olfr915) | 2.4 |
| NM_146456 | olfactory receptor 92(Olfr92) | 2.2 |
| NM_146782 | olfactory receptor 921(Olfr921) | 2.0 |
| NM_001011813 | olfactory receptor 93(Olfr93) | 2.0 |
| NM_146745 | olfactory receptor 957(Olfr957) | 2.3 |
| NM_146330 | olfactory receptor 958(Olfr958) | 2.4 |
| NM_146279 | olfactory receptor 960(Olfr960) | 2.1 |
| NM_146510 | olfactory receptor 98(Olfr98) | 2.6 |
| NM_146286 | olfactory receptor 981(Olfr981) | 2.1 |
| NM_146855 | olfactory receptor 985(Olfr985) | 2.5 |
| NM_001011785 | olfactory receptor 987(Olfr987) | 2.3 |
| NM_146437 | olfactory receptor 996(Olfr996) | 2.8 |
| NM_207563 | olfactory receptor1057(Olfr1057) | 0.3 |
| NM_207565 | olfactory receptor1113(Olfr1113) | 0.5 |
| NM_146297 | olfactory receptor1115(Olfr1115) | 0.4 |
| NM_147029 | olfactory receptor1120(Olfr1120) | 0.5 |
| NM_146648 | olfactory receptor1165(Olfr1165) | 0.4 |
| NM_146294 | olfactory receptor 1167(Olfr1167) | 0.5 |
| NM_146918 | olfactory receptor1180(Olfr1180) | 0.4 |
| NM_207568 | olfactory receptor1252(Olfr1252) | 0.5 |
| NM_146333 | olfactory receptor1274(Olfr1274) | 0.4 |
| NM_146395 | olfactory receptor1276(Olfr1276) | 0.4 |
| NM_001005568 | olfactory receptor 1281(Olfr1281) | 0.5 |
| NM_146401 | olfactory receptor 1305(Olfr1305) | 0.5 |
| NM_146867 | olfactory receptor 131(Olfr131) | 0.4 |
| NM_146832 | olfactory receptor 134(Olfr134) | 0.5 |
| NM_146304 | olfactory receptor 1340(Olfr1340) | 0.4 |
| NM_146913 | olfactory receptor 1348(Olfr1348) | 0.3 |
| NM_207136 | olfactory receptor 1349(Olfr1349) | 0.3 |
| NM_130868 | olfactory receptor 138(Olfr138) | 0.4 |
| NM_147003 | olfactory receptor 139(Olfr139) | 0.5 |
| NM_001011850 | olfactory receptor 1505(Olfr1505) | 0.4 |
| NM_146585 | olfactory receptor 1517(Olfr1517) | 0.4 |
| NM_019473 | olfactory receptor 155(Olfr155) | 0.4 |
| NM_146860 | olfactory receptor 161(Olfr161) | 0.5 |
| NM_146958 | olfactory receptor 171(Olfr171) | 0.5 |
| NM_001011801 | olfactory receptor 213(Olfr213) | 0.4 |
| NM_146405 | olfactory receptor 228(Olfr228) | 0.5 |
| NM_146269 | olfactory receptor 247(Olfr247) | 0.5 |
| NM_146688 | olfactory receptor 262(Olfr262) | 0.3 |
| NM_147022 | olfactory receptor 381(Olfr381) | 0.3 |
| NM_207137 | olfactory receptor 417(Olfr417) | 0.4 |
| NM_146721 | olfactory receptor 424(Olfr424) | 0.3 |
| NM_146988 | olfactory receptor 447(Olfr447) | 0.3 |
| NM_146734 | olfactory receptor 478(Olfr478) | 0.5 |
| NM_010991 | olfactory receptor 49(Olfr49) | 0.5 |
| NM_146723 | olfactory receptor 513(Olfr513) | 0.3 |
| NM_207160 | olfactory receptor 519(Olfr519) | 0.3 |
| NM_146520 | olfactory receptor 536(Olfr536) | 0.5 |
| NM_147112 | olfactory receptor 559(Olfr559) | 0.3 |
| NM_146727 | olfactory receptor 611(Olfr611) | 0.3 |
| NM_147080 | olfactory receptor 615(Olfr615) | 0.4 |
| NM_001025386 | olfactory receptor 627(Olfr627) | 0.3 |
| NM_147050 | olfactory receptor 659(Olfr659) | 0.3 |
| NM_146494 | olfactory receptor 722(Olfr722) | 0.5 |
| NM_146665 | olfactory receptor 732(Olfr732) | 0.2 |
| NM_146671 | olfactory receptor 822(Olfr822) | 0.5 |
| NM_146300 | olfactory receptor 827(Olfr827) | 0.5 |
| NM_146525 | olfactory receptor 847(Olfr847) | 0.5 |
| NM_146419 | olfactory receptor 883(Olfr883) | 0.4 |
| NM_146861 | olfactory receptor 9(Olfr9) | 0.4 |
| NM_146610 | olfactory receptor 972(Olfr972) | 0.3 |

TABLE 6

List of olfactory receptor genes in which the expression was changed by more than 2-fold change due to diet-induced obesity (12 weeks) in visceral fat tissue

| GenBank accession No. | Gene name (Gene symbol) | Expression fold change to HFD group |
|---|---|---|
| NM_146921 | olfactory receptor 1(Olfr1) | 2.6 |
| NM_001011695 | olfactory receptor 1000(Olfr1000) | 3.0 |
| NM_146573 | olfactory receptor 1002(Olfr1002) | 2.1 |

TABLE 6-continued

List of olfactory receptor genes in which the expression was changed by more than 2-fold change due to diet-induced obesity (12 weeks) in visceral fat tissue

| GenBank accession No. | Gene name (Gene symbol) | Expression fold change to HFD group |
|---|---|---|
| NM_146572 | olfactory receptor 1009(Olfr1009) | 2.7 |
| NM_146587 | olfactory receptor 1023(Olfr1023) | 2.0 |
| NM_207142 | olfactory receptor 1036(Olfr1036) | 2.3 |
| NM_147013 | olfactory receptor 1038(Olfr1038) | 2.2 |
| NM_001011783 | olfactory receptor 104(Olfr104) | 4.5 |
| NM_147010 | olfactory receptor 1052(Olfr1052) | 2.3 |
| NM_147019 | olfactory receptor 1054(Olfr1054) | 2.3 |
| NM_146408 | olfactory receptor 1065(Olfr1065) | 2.6 |
| NM_146752 | olfactory receptor 1106(Olfr1106) | 2.8 |
| NM_146642 | olfactory receptor 1140(Olfr1140) | 2.0 |
| NM_146293 | olfactory receptor 1143(Olfr1143) | 2.3 |
| NM_207566 | olfactory receptor 1173(Olfr1173) | 2.7 |
| XM_621554 | olfactory receptor 1174(Olfr1174) | 2.5 |
| NM_001011868 | olfactory receptor 1178(Olfr1178) | 2.0 |
| NM_146917 | olfactory receptor 1179(Olfr1179) | 3.1 |
| NM_001011816 | olfactory receptor 1181(Olfr1181) | 3.9 |
| NM_001005227 | olfactory receptor 1200(Olfr1200) | 2.2 |
| NM_146778 | olfactory receptor 1208(Olfr1208) | 2.2 |
| NM_146901 | olfactory receptor 1217(Olfr1217) | 2.0 |
| NM_146902 | olfactory receptor 1221(Olfr1221) | 3.3 |
| NM_146970 | olfactory receptor 1239(Olfr1239) | 2.2 |
| NM_146788 | olfactory receptor 1245(Olfr1245) | 2.0 |
| NM_146966 | olfactory receptor 1247(Olfr1247) | 3.2 |
| NM_146983 | olfactory receptor 1256(Olfr1256) | 3.1 |
| NM_146474 | olfactory receptor 1261(Olfr1261) | 2.5 |
| NM_146342 | olfactory receptor 1269(Olfr1269) | 3.6 |
| NM_146975 | olfactory receptor 1273(Olfr1273) | 2.3 |
| NM_146887 | olfactory receptor 1301(Olfr1301) | 3.0 |
| NM_001011787 | olfactory receptor 1307(Olfr1307) | 2.4 |
| NM_207151 | olfactory receptor 1308(Olfr1308) | 2.2 |
| NM_146852 | olfactory receptor 1339(Olfr1339) | 5.0 |
| NM_146385 | olfactory receptor 1347(Olfr1347) | 2.7 |
| NM_146911 | olfactory receptor 1377(Olfr1377) | 2.3 |
| NM_146467 | olfactory receptor 1388(Olfr1388) | 2.1 |
| NM_146651 | olfactory receptor 1403(Olfr1403) | 3.9 |
| NM_001011525 | olfactory receptor 1415(Olfr1415) | 2.4 |
| NM_146679 | olfactory receptor 1427(Olfr1427) | 2.9 |
| NM_146806 | olfactory receptor 143(Olfr143) | 2.0 |
| NM_207626 | olfactory receptor 1434(Olfr1434) | 2.1 |
| NM_146703 | olfactory receptor 1447(Olfr1447) | 2.4 |
| NM_146313 | olfactory receptor 145(Olfr145) | 2.4 |
| NM_146747 | olfactory receptor 146(Olfr146) | 2.2 |
| NM_146691 | olfactory receptor 1467(Olfr1467) | 2.1 |
| NM_146301 | olfactory receptor 1475(Olfr1475) | 2.1 |
| NM_146696 | olfactory receptor 1477(Olfr1477) | 2.5 |
| NM_207575 | olfactory receptor 1480(Olfr1480) | 2.5 |
| NM_146633 | olfactory receptor 1501(Olfr1501) | 3.0 |
| NM_008763 | olfactory receptor 16(Olfr16) | 2.3 |
| NM_146451 | olfactory receptor 164(Olfr164) | 2.6 |
| NM_001011855 | olfactory receptor 169(Olfr169) | 2.3 |
| NM_146999 | olfactory receptor 181(Olfr181) | 2.4 |
| NM_001005520 | olfactory receptor 244(Olfr244) | 2.3 |
| NM_146870 | olfactory receptor 25(Olfr25) | 2.1 |
| NM_207553 | olfactory receptor 251(Olfr251) | 2.0 |
| NM_146281 | olfactory receptor 284(Olfr284) | 2.2 |
| NM_146500 | olfactory receptor 319(Olfr319) | 3.4 |
| NM_146623 | olfactory receptor 357(Olfr357) | 2.2 |
| NM_207555 | olfactory receptor 372(Olfr372) | 2.1 |
| NM_147025 | olfactory receptor 380(Olfr380) | 2.2 |
| NM_146347 | olfactory receptor 390(Olfr390) | 2.7 |
| NM_146722 | olfactory receptor 429(Olfr429) | 2.7 |
| NM_146830 | olfactory receptor 44(Olfr44) | 2.7 |
| NM_146655 | olfactory receptor 441(Olfr441) | 6.2 |
| NM_147064 | olfactory receptor 449(Olfr449) | 2.4 |
| NM_146370 | olfactory receptor 47(Olfr47) | 3.6 |
| NM_010990 | olfactory receptor 48(Olfr48) | 2.3 |
| XM_146310 | olfactory receptor 493(Olfr493) | 4.7 |
| NM_146738 | olfactory receptor 497(Olfr497) | 2.2 |
| NM_146372 | olfactory receptor 509(Olfr509) | 3.8 |
| NM_146725 | olfactory receptor 516(Olfr516) | 2.2 |
| NM_147063 | olfactory receptor 520(Olfr520) | 2.4 |
| NM_146960 | olfactory receptor 53(Olfr53) | 2.3 |
| NM_147101 | olfactory receptor 549(Olfr549) | 2.8 |
| NM_147109 | olfactory receptor 577(Olfr577) | 3.3 |
| NM_147111 | olfactory receptor 586(Olfr586) | 2.1 |
| NM_207556 | olfactory receptor 592(Olfr592) | 3.5 |
| NM_207143 | olfactory receptor 594(Olfr594) | 3.1 |
| NM_146727 | olfactory receptor 611(Olfr611) | 2.9 |
| XM_993242 | olfactory receptor 664(Olfr664) | 3.8 |
| NM_001011862 | olfactory receptor 699(Olfr699) | 2.3 |
| NM_146597 | olfactory receptor 702(Olfr702) | 2.7 |
| NM_146353 | olfactory receptor 706(Olfr706) | 2.3 |
| NM_146780 | olfactory receptor 715(Olfr715) | 3.8 |
| NM_146554 | olfactory receptor 803(Olfr803) | 2.4 |
| NM_146555 | olfactory receptor 805(Olfr805) | 2.4 |
| NM_146567 | olfactory receptor 843(Olfr843) | 3.7 |
| NM_146282 | olfactory receptor 846(Olfr846) | 2.1 |
| NM_146528 | olfactory receptor 860(Olfr860) | 2.4 |
| NM_146882 | olfactory receptor 874(Olfr874) | 2.3 |
| NM_146883 | olfactory receptor 876(Olfr876) | 2.7 |
| NM_146479 | olfactory receptor 899(Olfr899) | 2.6 |
| NM_146811 | olfactory receptor 910(Olfr910) | 2.4 |
| NM_146786 | olfactory receptor 914(Olfr914) | 2.3 |
| NM_146375 | olfactory receptor 918(Olfr918) | 2.1 |
| NM_001011813 | olfactory receptor 93(Olfr93) | 2.4 |
| NM_146442 | olfactory receptor 934(Olfr934) | 2.2 |
| NM_146439 | olfactory receptor 937(Olfr937) | 4.3 |
| NM_146506 | olfactory receptor 945(Olfr945) | 3.5 |
| NM_147105 | olfactory receptor 978(Olfr978) | 2.3 |
| NM_146437 | olfactory receptor 996(Olfr996) | 3.8 |
| NM_146436 | olfactory receptor 998(Olfr998) | 2.3 |
| NM_146762 | olfactory receptor 1013(Olfr1013) | 0.4 |
| NM_146589 | olfactory receptor 1022(Olfr1022) | 0.4 |
| NM_001011852 | olfactory receptor 1029(Olfr1029) | 0.5 |
| NM_207563 | olfactory receptor 1057(Olfr1057) | 0.4 |
| NM_147078 | olfactory receptor 1062(Olfr1062) | 0.4 |
| NM_001005485 | olfactory receptor 111(Olfr111) | 0.5 |
| NM_146297 | olfactory receptor 1115(Olfr1115) | 0.3 |
| NM_207632 | olfactory receptor 1118(Olfr1118) | 0.3 |
| NM_147030 | olfactory receptor 1134(Olfr1134) | 0.4 |
| NM_146637 | olfactory receptor 1141(Olfr1141) | 0.5 |
| NM_146898 | olfactory receptor 1213(Olfr1213) | 0.5 |
| NM_146968 | olfactory receptor 1242(Olfr1242) | 0.4 |
| NM_146907 | olfactory receptor 1282(Olfr1282) | 0.4 |
| NM_146404 | olfactory receptor 1289(Olfr1289) | 0.5 |
| NM_146832 | olfactory receptor 134(Olfr134) | 0.4 |
| NM_146916 | olfactory receptor 1346(Olfr1346) | 0.5 |
| NM_207572 | olfactory receptor 1365(Olfr1365) | 0.4 |
| NM_146534 | olfactory receptor 1368(Olfr1368) | 0.4 |
| NM_146469 | olfactory receptor 1381(Olfr1381) | 0.4 |
| NM_147066 | olfactory receptor 1389(Olfr1389) | 0.5 |
| NM_146471 | olfactory receptor 1393(Olfr1393) | 0.5 |
| NM_146337 | olfactory receptor 1396(Olfr1396) | 0.4 |
| NM_146701 | olfactory receptor 1448(Olfr1448) | 0.5 |
| NM_146636 | olfactory receptor 1487(Olfr1487) | 0.4 |
| NM_146796 | olfactory receptor 1499(Olfr1499) | 0.5 |
| NM_146265 | olfactory receptor 1506(Olfr1506) | 0.4 |
| NM_146860 | olfactory receptor 161(Olfr161) | 0.4 |
| NM_146958 | olfactory receptor 171(Olfr171) | 0.4 |
| NM_146322 | olfactory receptor 187(Olfr187) | 0.4 |
| NM_146335 | olfactory receptor 19(Olfr19) | 0.5 |
| NM_001011801 | olfactory receptor 213(Olfr213) | 0.5 |
| NM_146759 | olfactory receptor 214(Olfr214) | 0.5 |
| NM_146280 | olfactory receptor 281(Olfr281) | 0.5 |
| NM_146617 | olfactory receptor 307(Olfr307) | 0.2 |
| NM_207230 | olfactory receptor 320(Olfr320) | 0.5 |
| NM_146502 | olfactory receptor 328(Olfr328) | 0.4 |
| NM_207235 | olfactory receptor 358(Olfr358) | 0.4 |
| NM_146711 | olfactory receptor 43(Olfr43) | 0.4 |
| NM_146733 | olfactory receptor 482(Olfr482) | 0.4 |
| NM_146311 | olfactory receptor 510(Olfr510) | 0.5 |
| NM_146723 | olfactory receptor 513(Olfr513) | 0.4 |
| NM_146520 | olfactory receptor 536(Olfr536) | 0.5 |
| NM_147079 | olfactory receptor 547(Olfr547) | 0.4 |

TABLE 6-continued

List of olfactory receptor genes in which the expression was changed by more than 2-fold change due to diet-induced obesity (12 weeks) in visceral fat tissue

| GenBank accession No. | Gene name (Gene symbol) | Expression fold change to HFD group |
|---|---|---|
| NM_147113 | olfactory receptor 560(Olfr560) | 0.5 |
| NM_147114 | olfactory receptor 575(Olfr575) | 0.5 |
| NM_147053 | olfactory receptor 582(Olfr582) | 0.3 |
| NM_001025386 | olfactory receptor 627(Olfr627) | 0.4 |
| NM_146959 | olfactory receptor 631(Olfr631) | 0.5 |
| NM_147074 | olfactory receptor 653(Olfr653) | 0.5 |
| NM_146392 | olfactory receptor 720(Olfr720) | 0.3 |
| NM_146494 | olfactory receptor 722(Olfr722) | 0.5 |
| NM_146664 | olfactory receptor 734(Olfr734) | 0.3 |
| NM_146682 | olfactory receptor 76(Olfr76) | 0.5 |
| NM_146378 | olfactory receptor 794(Olfr794) | 0.5 |
| NM_146674 | olfactory receptor 824(Olfr824) | 0.4 |
| NM_146557 | olfactory receptor 869(Olfr869) | 0.4 |
| NM_146419 | olfactory receptor 883(Olfr883) | 0.4 |
| NM_146424 | olfactory receptor 888(Olfr888) | 0.5 |
| NM_146787 | olfactory receptor 920(Olfr920) | 0.3 |
| NM_146746 | olfactory receptor 935(Olfr935) | 0.5 |
| NM_146507 | olfactory receptor 944(Olfr944) | 0.3 |
| NM_146611 | olfactory receptor 970(Olfr970) | 0.4 |
| NM_146615 | olfactory receptor 986(Olfr986) | 0.4 |

TABLE 7

List of olfactory receptor genes in which the expression was changed by more than 2-fold change due to diet-induced obesity (2 weeks) in subcutaneous fat tissue

| GenBank accession No. | Gene name (Gene symbol) | Expression fold change to HFD group |
|---|---|---|
| NM_146573 | olfactory receptor 1002(Olfr1002) | 2.9 |
| NM_146407 | olfactory receptor 1079(Olfr1079) | 2.0 |
| NM_146645 | olfactory receptor 1158(Olfr1158) | 2.0 |
| NM_146532 | olfactory receptor 1170(Olfr1170) | 3.1 |
| XM_619781 | olfactory receptor 1177(Olfr1177) | 2.6 |
| NM_146918 | olfactory receptor 1180(Olfr1180) | 2.1 |
| NM_146629 | olfactory receptor 121(Olfr121) | 2.2 |
| NM_146630 | olfactory receptor 123(Olfr123) | 2.6 |
| NM_146974 | olfactory receptor 1262(Olfr1262) | 2.8 |
| NM_146794 | olfactory receptor 1263(Olfr1263) | 3.7 |
| NM_146885 | olfactory receptor 1294(Olfr1294) | 2.2 |
| NM_146447 | olfactory receptor 1309(Olfr1309) | 3.5 |
| NM_146448 | olfactory receptor 1317(Olfr1317) | 2.5 |
| NM_146984 | olfactory receptor 142(Olfr142) | 2.2 |
| NM_146699 | olfactory receptor 1445(Olfr1445) | 2.5 |
| NM_146693 | olfactory receptor 1462(Olfr1462) | 2.0 |
| NM_001011850 | olfactory receptor 1505(Olfr1505) | 2.1 |
| NM_146585 | olfactory receptor 1517(Olfr1517) | 3.4 |
| NM_146451 | olfactory receptor 164(Olfr164) | 2.1 |
| NM_146995 | olfactory receptor 202(Olfr202) | 2.2 |
| NM_146759 | olfactory receptor 214(Olfr214) | 2.1 |
| NM_146405 | olfactory receptor 228(Olfr228) | 2.2 |
| NM_207175 | olfactory receptor 239(Olfr239) | 2.1 |
| NM_146619 | olfactory receptor 303(Olfr303) | 2.2 |
| NM_147006 | olfactory receptor 392(Olfr392) | 3.6 |
| NM_146718 | olfactory receptor 430(Olfr430) | 2.9 |
| NM_146830 | olfactory receptor 44(Olfr44) | 2.9 |
| NM_001005488 | olfactory receptor 467(Olfr467) | 3.1 |
| XM_891283 | olfactory receptor 471(Olfr471) | 2.2 |
| NM_146307 | olfactory receptor 498(Olfr498) | 2.0 |
| NM_146583 | olfactory receptor 52(Olfr52) | 2.5 |
| NM_147101 | olfactory receptor 549(Olfr549) | 2.2 |
| NM_207621 | olfactory receptor 553(Olfr553) | 4.8 |
| NM_147070 | olfactory receptor 604(Olfr604) | 2.2 |
| NM_146727 | olfactory receptor 611(Olfr611) | 2.0 |
| NM_146354 | olfactory receptor 633(Olfr633) | 3.2 |
| NM_207008 | olfactory receptor 773(Olfr773-ps1) | 2.9 |
| NM_207559 | olfactory receptor 776(Olfr776) | 2.6 |
| NM_146284 | olfactory receptor 780(Olfr780) | 2.5 |
| NM_146605 | olfactory receptor 828(Olfr828) | 2.9 |
| NM_146861 | olfactory receptor 9(Olfr9) | 2.0 |
| NM_207149 | olfactory receptor 1010(Olfr1010) | 0.3 |
| NM_146408 | olfactory receptor 1065(Olfr1065) | 0.5 |
| NM_146845 | olfactory receptor 1098(Olfr1098) | 0.3 |
| NM_001011825 | olfactory receptor 1105(Olfr1105) | 0.4 |
| NM_207565 | olfactory receptor 1113(Olfr1113) | 0.4 |
| NM_146349 | olfactory receptor 1128(Olfr1128) | 0.4 |
| NM_146838 | olfactory receptor 1130(Olfr1130) | 0.4 |
| NM_146658 | olfactory receptor 1131(Olfr1131) | 0.4 |
| NM_146836 | olfactory receptor 1132(Olfr1132) | 0.4 |
| NM_147030 | olfactory receptor 1134(Olfr1134) | 0.5 |
| NM_001011868 | olfactory receptor 1178(Olfr1178) | 0.4 |
| NM_146464 | olfactory receptor 1196(Olfr1196) | 0.4 |
| NM_001005225 | olfactory receptor 1197(Olfr1197) | 0.4 |
| NM_146458 | olfactory receptor 1199(Olfr1199) | 0.5 |
| NM_146973 | olfactory receptor 1234(Olfr1234) | 0.5 |
| NM_146788 | olfactory receptor 1245(Olfr1245) | 0.4 |
| NM_146966 | olfactory receptor 1247(Olfr1247) | 0.4 |
| NM_146982 | olfactory receptor 1257(Olfr1257) | 0.5 |
| NM_146890 | olfactory receptor 126(Olfr126) | 0.5 |
| NM_146395 | olfactory receptor 1276(Olfr1276) | 0.5 |
| NM_146652 | olfactory receptor 13(Olfr13) | 0.3 |
| NM_146362 | olfactory receptor 1312(Olfr1312) | 0.4 |
| NM_207570 | olfactory receptor 1328(Olfr1328) | 0.4 |
| NM_207152 | olfactory receptor 1338(Olfr1338) | 0.4 |
| NM_207136 | olfactory receptor 1349(Olfr1349) | 0.4 |
| NM_146389 | olfactory receptor 1350(Olfr1350) | 0.3 |
| NM_147040 | olfactory receptor 1351(Olfr1351) | 0.3 |
| NM_207571 | olfactory receptor 1355(Olfr1355) | 0.4 |
| NM_146535 | olfactory receptor 1370(Olfr1370) | 0.4 |
| NM_207227 | olfactory receptor 1373(Olfr1373) | 0.5 |
| NM_001011790 | olfactory receptor 1382(Olfr1382) | 0.5 |
| NM_207574 | olfactory receptor 1383(Olfr1383) | 0.5 |
| NM_147037 | olfactory receptor 1413(Olfr1413) | 0.4 |
| NM_146701 | olfactory receptor 1448(Olfr1448) | 0.4 |
| NM_146689 | olfactory receptor 1459(Olfr1459) | 0.4 |
| NM_019476 | olfactory receptor 159(Olfr159) | 0.4 |
| NM_146686 | olfactory receptor 232(Olfr232) | 0.5 |
| NM_207553 | olfactory receptor 251(Olfr251) | 0.3 |
| NM_146920 | olfactory receptor 267(Olfr267) | 0.3 |
| NM_001011751 | olfactory receptor 298(Olfr298) | 0.4 |
| NM_001011866 | olfactory receptor 309(Olfr309) | 0.4 |
| NM_146537 | olfactory receptor 311(Olfr311) | 0.4 |
| NM_010980 | olfactory receptor 32(Olfr32) | 0.4 |
| XM_620674 | olfactory receptor 373(Olfr373) | 0.4 |
| NM_147023 | olfactory receptor 385(Olfr385) | 0.3 |
| NM_146347 | olfactory receptor 390(Olfr390) | 0.5 |
| NM_146346 | olfactory receptor 397(Olfr397) | 0.3 |
| NM_146721 | olfactory receptor 424(Olfr424) | 0.4 |
| NM_146987 | olfactory receptor 457(Olfr457) | 0.3 |
| NM_146444 | olfactory receptor 458(Olfr458) | 0.5 |
| NM_146819 | olfactory receptor 466(Olfr466) | 0.4 |
| NM_146925 | olfactory receptor 481(Olfr481) | 0.4 |
| NM_146737 | olfactory receptor 494(Olfr494) | 0.5 |
| NM_001011858 | olfactory receptor 504(Olfr504) | 0.4 |
| NM_146725 | olfactory receptor 516(Olfr516) | 0.5 |
| NM_146954 | olfactory receptor 535(Olfr535) | 0.3 |
| NM_010997 | olfactory receptor 54(Olfr54) | 0.5 |
| NM_147113 | olfactory receptor 560(Olfr560) | 0.5 |
| NM_147053 | olfactory receptor 582(Olfr582) | 0.3 |
| NM_146731 | olfactory receptor 599(Olfr599) | 0.4 |
| NM_146314 | olfactory receptor 601(Olfr601) | 0.5 |
| NM_146841 | olfactory receptor 617(Olfr617) | 0.2 |
| NM_147050 | olfactory receptor 659(Olfr659) | 0.4 |
| NM_207146 | olfactory receptor 670(Olfr670) | 0.3 |
| NM_146760 | olfactory receptor 672(Olfr672) | 0.5 |
| NM_147061 | olfactory receptor 691(Olfr691) | 0.5 |
| NM_146392 | olfactory receptor 720(Olfr720) | 0.4 |
| NM_146319 | olfactory receptor 727(Olfr727) | 0.3 |
| NM_146667 | olfactory receptor 740(Olfr740) | 0.4 |

TABLE 7-continued

List of olfactory receptor genes in which the expression was changed by more than 2-fold change due to diet-induced obesity (2 weeks) in subcutaneous fat tissue

| GenBank accession No. | Gene name (Gene symbol) | Expression fold change to HFD group |
|---|---|---|
| NM_146430 | olfactory receptor 742(Olfr742) | 0.3 |
| NM_001011738 | olfactory receptor 744(Olfr744) | 0.5 |
| NM_146864 | olfactory receptor 768(Olfr768) | 0.4 |
| NM_207201 | olfactory receptor 8(Olfr8) | 0.3 |
| NM_146776 | olfactory receptor 821(Olfr821) | 0.5 |
| NM_146564 | olfactory receptor 836(Olfr836) | 0.3 |
| NM_146525 | olfactory receptor 847(Olfr847) | 0.5 |
| NM_146882 | olfactory receptor 874(Olfr874) | 0.3 |
| NM_001011739 | olfactory receptor 885(Olfr885) | 0.3 |
| NM_146477 | olfactory receptor 90(Olfr90) | 0.5 |
| NM_146811 | olfactory receptor 910(Olfr910) | 0.4 |
| NM_146272 | olfactory receptor 930(Olfr930) | 0.2 |
| NM_001011518 | olfactory receptor 94(Olfr94) | 0.4 |
| NM_207141 | olfactory receptor 955(Olfr955) | 0.4 |
| NM_146514 | olfactory receptor 96(Olfr96) | 0.3 |
| NM_146504 | olfactory receptor 961(Olfr961) | 0.4 |
| NM_146828 | olfactory receptor 975(Olfr975) | 0.3 |
| NM_146286 | olfactory receptor 981(Olfr981) | 0.4 |

TABLE 8

List of olfactory receptor genes in which the expression was changed by more than 2-fold change due to diet-induced obesity (4 weeks) in subcutaneous fat tissue

| GenBank accession No. | Gene name (Gene symbol) | Expression fold change to HFD group |
|---|---|---|
| NM_146570 | olfactory receptor 1006(Olfr1006) | 2.1 |
| NM_146568 | olfactory receptor 1012(Olfr1012) | 2.0 |
| NM_146762 | olfactory receptor 1013(Olfr1013) | 2.7 |
| NM_207142 | olfactory receptor 1036(Olfr1036) | 2.4 |
| NM_207564 | olfactory receptor 1083(Olfr1083) | 2.2 |
| NM_146846 | olfactory receptor 1087(Olfr1087) | 3.5 |
| NM_146730 | olfactory receptor 1095(Olfr1095) | 2.3 |
| NM_147031 | olfactory receptor 1122(Olfr1122) | 2.3 |
| NM_146642 | olfactory receptor 1140(Olfr1140) | 2.2 |
| NM_146644 | olfactory receptor 1163(Olfr1163) | 2.4 |
| NM_207566 | olfactory receptor 1173(Olfr1173) | 2.3 |
| XM_619781 | olfactory receptor 1177(Olfr1177) | 2.2 |
| NM_146965 | olfactory receptor 1250(Olfr1250) | 2.8 |
| NM_146974 | olfactory receptor 1262(Olfr1262) | 2.0 |
| NM_146342 | olfactory receptor 1269(Olfr1269) | 2.2 |
| NM_146908 | olfactory receptor 1280(Olfr1280) | 2.9 |
| NM_146907 | olfactory receptor 1282(Olfr1282) | 2.4 |
| NM_207150 | olfactory receptor 1313(Olfr1313) | 2.6 |
| NM_146713 | olfactory receptor 1342(Olfr1342) | 2.1 |
| NM_146679 | olfactory receptor 1427(Olfr1427) | 2.8 |
| NM_001011839 | olfactory receptor 1437(Olfr1437) | 2.4 |
| NM_146692 | olfactory receptor 1454(Olfr1454) | 2.6 |
| NM_207132 | olfactory receptor 1471(Olfr1471) | 2.2 |
| NM_146696 | olfactory receptor 1477(Olfr1477) | 2.5 |
| NM_146990 | olfactory receptor 1494(Olfr1494) | 2.4 |
| NM_030553 | olfactory receptor 160(Olfr160) | 2.9 |
| NM_146322 | olfactory receptor 187(Olfr187) | 2.8 |
| NM_146992 | olfactory receptor 204(Olfr204) | 2.9 |
| NM_146912 | olfactory receptor 211(Olfr211) | 2.4 |
| NM_146628 | olfactory receptor 344(Olfr344) | 3.4 |
| NM_146859 | olfactory receptor 371(Olfr371) | 2.5 |
| NM_207137 | olfactory receptor 417(Olfr417) | 2.4 |
| NM_001005488 | olfactory receptor 467(Olfr467) | 2.4 |
| NM_146739 | olfactory receptor 502(Olfr502) | 2.8 |
| NM_010998 | olfactory receptor 55(Olfr55) | 3.2 |
| NM_147093 | olfactory receptor 558(Olfr558) | 3.2 |
| NM_147091 | olfactory receptor 568(Olfr568) | 2.2 |
| NM_147041 | olfactory receptor 57(Olfr57) | 4.1 |
| NM_013618 | olfactory receptor 66(Olfr66) | 2.4 |
| NM_146758 | olfactory receptor 678(Olfr678) | 2.4 |

TABLE 8-continued

List of olfactory receptor genes in which the expression was changed by more than 2-fold change due to diet-induced obesity (4 weeks) in subcutaneous fat tissue

| GenBank accession No. | Gene name (Gene symbol) | Expression fold change to HFD group |
|---|---|---|
| NM_146750 | olfactory receptor 689(Olfr689) | 2.7 |
| NM_146596 | olfactory receptor 703(Olfr703) | 2.4 |
| NM_146665 | olfactory receptor 732(Olfr732) | 4.0 |
| NM_146339 | olfactory receptor 77(Olfr77) | 2.4 |
| NM_207559 | olfactory receptor 776(Olfr776) | 2.5 |
| NM_001011797 | olfactory receptor 782(Olfr782) | 2.1 |
| NM_146548 | olfactory receptor 800(Olfr800) | 2.9 |
| NM_146553 | olfactory receptor 806(Olfr806) | 3.0 |
| NM_146324 | olfactory receptor 809(Olfr809) | 2.5 |
| NM_146605 | olfactory receptor 828(Olfr828) | 3.2 |
| NM_146525 | olfactory receptor 847(Olfr847) | 2.2 |
| NM_146861 | olfactory receptor 9(Olfr9) | 2.6 |
| NM_146507 | olfactory receptor 944(Olfr944) | 4.0 |
| NM_146330 | olfactory receptor 958(Olfr958) | 2.2 |
| NM_146826 | olfactory receptor 969(Olfr969) | 2.3 |
| NM_146433 | olfactory receptor 994(Olfr994) | 2.6 |
| NM_206822 | olfactory receptor 10(Olfr10) | 0.5 |
| NM_147012 | olfactory receptor 1047(Olfr1047) | 0.3 |
| NM_146409 | olfactory receptor 1080(Olfr1080) | 0.5 |
| NM_146590 | olfactory receptor 1085(Olfr1085) | 0.3 |
| NM_146845 | olfactory receptor 1098(Olfr1098) | 0.4 |
| NM_146349 | olfactory receptor 1128(Olfr1128) | 0.5 |
| NM_146838 | olfactory receptor 1130(Olfr1130) | 0.2 |
| NM_147030 | olfactory receptor 1134(Olfr1134) | 0.5 |
| NM_146648 | olfactory receptor 1165(Olfr1165) | 0.5 |
| NM_146631 | olfactory receptor 120(Olfr120) | 0.4 |
| NM_146897 | olfactory receptor 1214(Olfr1214) | 0.4 |
| NM_146630 | olfactory receptor 123(Olfr123) | 0.5 |
| NM_146970 | olfactory receptor 1239(Olfr1239) | 0.4 |
| NM_146455 | olfactory receptor 1241(Olfr1241) | 0.5 |
| NM_146341 | olfactory receptor 1259(Olfr1259) | 0.4 |
| NM_146377 | olfactory receptor 127(Olfr127) | 0.4 |
| NM_146985 | olfactory receptor 1270(Olfr1270) | 0.4 |
| NM_146793 | olfactory receptor 1271(Olfr1271) | 0.4 |
| NM_146980 | olfactory receptor 1272(Olfr1272) | 0.4 |
| XM_888068 | olfactory receptor 1293(Olfr1293) | 0.5 |
| NM_146652 | olfactory receptor 13(Olfr13) | 0.4 |
| NM_146853 | olfactory receptor 1341(Olfr1341) | 0.5 |
| NM_207227 | olfactory receptor 1373(Olfr1373) | 0.5 |
| NM_146704 | olfactory receptor 1446(Olfr1446) | 0.4 |
| NM_146313 | olfactory receptor 145(Olfr145) | 0.5 |
| NM_001011840 | olfactory receptor 1463(Olfr1463) | 0.3 |
| NM_146301 | olfactory receptor 1475(Olfr1475) | 0.5 |
| NM_207138 | olfactory receptor 149(Olfr149) | 0.4 |
| NM_146796 | olfactory receptor 1499(Olfr1499) | 0.4 |
| NM_020513 | olfactory receptor 1508(Olfr1508) | 0.5 |
| NM_207554 | olfactory receptor 257(Olfr257) | 0.4 |
| NM_146688 | olfactory receptor 262(Olfr262) | 0.4 |
| NM_146829 | olfactory receptor 27(Olfr27) | 0.4 |
| NM_146416 | olfactory receptor 290(Olfr290) | 0.5 |
| NM_146951 | olfactory receptor 340(Olfr340) | 0.4 |
| NM_146708 | olfactory receptor 402(Olfr402) | 0.4 |
| NM_146711 | olfactory receptor 43(Olfr43) | 0.3 |
| NM_146273 | olfactory receptor 448(Olfr448) | 0.5 |
| NM_146413 | olfactory receptor 463(Olfr463) | 0.5 |
| NM_146819 | olfactory receptor 466(Olfr466) | 0.3 |
| NM_146370 | olfactory receptor 47(Olfr47) | 0.4 |
| NM_146926 | olfactory receptor 477(Olfr477) | 0.4 |
| NM_010990 | olfactory receptor 48(Olfr48) | 0.3 |
| NM_146498 | olfactory receptor 490(Olfr490) | 0.2 |
| NM_146497 | olfactory receptor 492(Olfr492) | 0.5 |
| NM_001011858 | olfactory receptor 504(Olfr504) | 0.5 |
| NM_146743 | olfactory receptor 507(Olfr507) | 0.5 |
| NM_146359 | olfactory receptor 564(Olfr564) | 0.4 |
| NM_147114 | olfactory receptor 575(Olfr575) | 0.3 |
| NM_207143 | olfactory receptor 594(Olfr594) | 0.5 |
| NM_147080 | olfactory receptor 615(Olfr615) | 0.3 |
| NM_146841 | olfactory receptor 617(Olfr617) | 0.5 |
| NM_147084 | olfactory receptor 639(Olfr639) | 0.4 |
| NM_146329 | olfactory receptor 642(Olfr642) | 0.5 |
| NM_147055 | olfactory receptor 649(Olfr649) | 0.4 |
| NM_146814 | olfactory receptor 665(Olfr665) | 0.5 |

TABLE 8-continued

List of olfactory receptor genes in which the expression was changed by more than 2-fold change due to diet-induced obesity (4 weeks) in subcutaneous fat tissue

| GenBank accession No. | Gene name (Gene symbol) | Expression fold change to HFD group |
| --- | --- | --- |
| NM_207146 | olfactory receptor 670(Olfr670) | 0.3 |
| NM_147061 | olfactory receptor 691(Olfr691) | 0.3 |
| NM_019486 | olfactory receptor 71(Olfr71) | 0.3 |
| NM_146780 | olfactory receptor 715(Olfr715) | 0.4 |
| NM_146392 | olfactory receptor 720(Olfr720) | 0.5 |
| NM_146492 | olfactory receptor 724(Olfr724) | 0.3 |
| NM_146668 | olfactory receptor 739(Olfr739) | 0.4 |
| NM_146551 | olfactory receptor 788(Olfr788) | 0.4 |
| NM_146554 | olfactory receptor 803(Olfr803) | 0.5 |
| NM_146423 | olfactory receptor 887(Olfr887) | 0.4 |
| NM_146477 | olfactory receptor 90(Olfr90) | 0.3 |
| NM_146811 | olfactory receptor 910(Olfr910) | 0.4 |
| NM_001011523 | olfactory receptor 913(Olfr913) | 0.5 |
| NM_001011813 | olfactory receptor 93(Olfr93) | 0.4 |
| NM_146272 | olfactory receptor 930(Olfr930) | 0.4 |
| NM_146513 | olfactory receptor 95(Olfr95) | 0.4 |
| NM_146612 | olfactory receptor 968(Olfr968) | 0.3 |
| NM_146828 | olfactory receptor 975(Olfr975) | 0.4 |
| NM_146510 | olfactory receptor 98(Olfr98) | 0.5 |
| NM_146286 | olfactory receptor 981(Olfr981) | 0.5 |
| NM_146434 | olfactory receptor 995(Olfr995) | 0.4 |

TABLE 9

List of olfactory receptor genes in which the expression was changed by more than 2-fold change due to diet-induced obesity (8 weeks) in subcutaneous fat tissue

| GenBank accession No. | Gene name (Gene symbol) | Expression fold change to HFD group |
| --- | --- | --- |
| NM_146921 | olfactory receptor 1(Olfr1) | 3.0 |
| NM_147021 | olfactory receptor 1055(Olfr1055) | 2.8 |
| NM_207563 | olfactory receptor 1057(Olfr1057) | 10.8 |
| NM_146542 | olfactory receptor 11(Olfr11) | 2.6 |
| NM_146594 | olfactory receptor 1100(Olfr1100) | 2.4 |
| NM_001011825 | olfactory receptor 1105(Olfr1105) | 3.6 |
| NM_146752 | olfactory receptor 1106(Olfr1106) | 2.1 |
| NM_146289 | olfactory receptor 113(Olfr113) | 2.1 |
| NM_146287 | olfactory receptor 114(Olfr114) | 2.8 |
| NM_146293 | olfactory receptor 1143(Olfr1143) | 5.8 |
| NM_146849 | olfactory receptor 1157(Olfr1157) | 2.1 |
| NM_146848 | olfactory receptor 1161(Olfr1161) | 3.5 |
| NM_146294 | olfactory receptor 1167(Olfr1167) | 2.0 |
| XM_619781 | olfactory receptor 1177(Olfr1177) | 2.9 |
| NM_001011816 | olfactory receptor 1181(Olfr1181) | 2.4 |
| NM_146629 | olfactory receptor 121(Olfr121) | 3.0 |
| NM_146901 | olfactory receptor 1217(Olfr1217) | 2.1 |
| NM_146792 | olfactory receptor 1246(Olfr1246) | 2.5 |
| NM_146343 | olfactory receptor 1265(Olfr1265) | 2.1 |
| NM_146342 | olfactory receptor 1269(Olfr1269) | 2.3 |
| NM_146975 | olfactory receptor 1273(Olfr1273) | 2.7 |
| NM_207254 | olfactory receptor 1286(Olfr1286) | 2.2 |
| NM_207703 | olfactory receptor 1335(Olfr1335) | 2.5 |
| NM_147042 | olfactory receptor 1353(Olfr1353) | 2.6 |
| NM_207571 | olfactory receptor 1355(Olfr1355) | 2.0 |
| NM_146534 | olfactory receptor 1368(Olfr1368) | 2.8 |
| NM_207573 | olfactory receptor 1380(Olfr1380) | 2.7 |
| NM_147003 | olfactory receptor 139(Olfr139) | 2.2 |
| NM_146470 | olfactory receptor 1392(Olfr1392) | 2.2 |
| NM_146490 | olfactory receptor 1411(Olfr1411) | 2.9 |
| NM_146984 | olfactory receptor 142(Olfr142) | 2.5 |
| NM_146679 | olfactory receptor 1427(Olfr1427) | 3.0 |
| NM_146691 | olfactory receptor 1467(Olfr1467) | 3.0 |
| NM_008762 | olfactory receptor 15(Olfr15) | 2.4 |
| NM_001011831 | olfactory receptor 1500(Olfr1500) | 2.2 |
| NM_020513 | olfactory receptor 1508(Olfr1508) | 2.5 |
| NM_146466 | olfactory receptor 165(Olfr165) | 2.1 |

TABLE 9-continued

List of olfactory receptor genes in which the expression was changed by more than 2-fold change due to diet-induced obesity (8 weeks) in subcutaneous fat tissue

| GenBank accession No. | Gene name (Gene symbol) | Expression fold change to HFD group |
| --- | --- | --- |
| NM_147068 | olfactory receptor 166(Olfr166) | 2.5 |
| NM_146935 | olfactory receptor 167(Olfr167) | 2.2 |
| NM_146357 | olfactory receptor 168(Olfr168) | 2.3 |
| NM_146958 | olfactory receptor 171(Olfr171) | 2.0 |
| NM_147002 | olfactory receptor 174(Olfr174) | 3.2 |
| NM_146335 | olfactory receptor 19(Olfr19) | 2.3 |
| NM_001011791 | olfactory receptor 193(Olfr193) | 2.2 |
| NM_001011736 | olfactory receptor 205(Olfr205) | 2.1 |
| NM_146912 | olfactory receptor 211(Olfr211) | 2.2 |
| NM_146446 | olfactory receptor 215(Olfr215) | 2.5 |
| NM_146489 | olfactory receptor 266(Olfr266) | 2.4 |
| NM_146829 | olfactory receptor 27(Olfr27) | 2.4 |
| NM_146457 | olfactory receptor 282(Olfr282) | 2.3 |
| NM_001011767 | olfactory receptor 299(Olfr299) | 2.4 |
| NM_146878 | olfactory receptor 30(Olfr30) | 2.2 |
| NM_146947 | olfactory receptor 338(Olfr338) | 2.1 |
| NM_146951 | olfactory receptor 340(Olfr340) | 2.9 |
| NM_146938 | olfactory receptor 346(Olfr346) | 2.2 |
| NM_146368 | olfactory receptor 361(Olfr361) | 2.9 |
| XM_619748 | olfactory receptor 367(Olfr367) | 2.7 |
| NM_146374 | olfactory receptor 368(Olfr368) | 2.3 |
| NM_146270 | olfactory receptor 370(Olfr370) | 3.3 |
| NM_146825 | olfactory receptor 39(Olfr39) | 2.0 |
| NM_010984 | olfactory receptor 42(Olfr42) | 2.2 |
| NM_146445 | olfactory receptor 450(Olfr450) | 2.2 |
| NM_146734 | olfactory receptor 478(Olfr478) | 2.0 |
| NM_146732 | olfactory receptor 488(Olfr488) | 4.1 |
| NM_146736 | olfactory receptor 491(Olfr491) | 2.9 |
| NM_146310 | olfactory receptor 493(Olfr493) | 2.5 |
| NM_001011527 | olfactory receptor 503(Olfr503) | 2.1 |
| NM_001011846 | olfactory receptor 517(Olfr517) | 2.2 |
| NM_146306 | olfactory receptor 518(Olfr518) | 3.2 |
| NM_146583 | olfactory receptor 52(Olfr52) | 2.5 |
| NM_146956 | olfactory receptor 525(Olfr525) | 3.1 |
| NM_207621 | olfactory receptor 553(Olfr553) | 4.4 |
| NM_011002 | olfactory receptor 59(Olfr59) | 2.3 |
| NM_146731 | olfactory receptor 599(Olfr599) | 3.2 |
| NM_146314 | olfactory receptor 601(Olfr601) | 2.1 |
| NM_147070 | olfactory receptor 604(Olfr604) | 2.0 |
| NM_146354 | olfactory receptor 633(Olfr633) | 2.2 |
| XM_993242 | olfactory receptor 664(Olfr664) | 2.2 |
| NM_147060 | olfactory receptor 667(Olfr667) | 3.6 |
| NM_001011848 | olfactory receptor 675(Olfr675) | 2.1 |
| NM_146453 | olfactory receptor 693(Olfr693) | 2.7 |
| NM_146597 | olfactory receptor 702(Olfr702) | 2.1 |
| NM_146604 | olfactory receptor 716(Olfr716) | 2.0 |
| NM_001011809 | olfactory receptor 728(Olfr728) | 2.1 |
| NM_146363 | olfactory receptor 731(Olfr731) | 2.4 |
| NM_146664 | olfactory receptor 734(Olfr734) | 3.5 |
| NM_146667 | olfactory receptor 740(Olfr740) | 2.9 |
| NM_001011738 | olfactory receptor 744(Olfr744) | 2.8 |
| NM_146422 | olfactory receptor 767(Olfr767) | 5.0 |
| NM_207008 | olfactory receptor 773(Olfr773) | 5.8 |
| NM_146933 | olfactory receptor 790(Olfr790) | 2.1 |
| NM_146553 | olfactory receptor 806(Olfr806) | 3.9 |
| NM_146882 | olfactory receptor 874(Olfr874) | 2.2 |
| NM_146478 | olfactory receptor 891(Olfr891) | 2.6 |
| NM_146872 | olfactory receptor 908(Olfr908) | 3.5 |
| NM_146810 | olfactory receptor 912(Olfr912) | 2.8 |
| NM_146610 | olfactory receptor 972(Olfr972) | 2.2 |
| NM_147106 | olfactory receptor 980(Olfr980) | 2.4 |
| NM_146579 | olfactory receptor 1032(Olfr1032) | 0.5 |
| NM_207562 | olfactory receptor 1051(Olfr1051) | 0.3 |
| NM_146592 | olfactory receptor 1086(Olfr1086) | 0.5 |
| NM_146365 | olfactory receptor 1094(Olfr1094) | 0.4 |
| NM_146591 | olfactory receptor 1101(Olfr1101) | 0.5 |
| NM_146349 | olfactory receptor 1128(Olfr1128) | 0.5 |
| NM_146838 | olfactory receptor 1130(Olfr1130) | 0.3 |
| NM_146323 | olfactory receptor 1232(Olfr1232) | 0.5 |
| NM_146867 | olfactory receptor 131(Olfr131) | 0.5 |
| NM_147040 | olfactory receptor 1351(Olfr1351) | 0.5 |
| NM_146695 | olfactory receptor 1469(Olfr1469) | 0.4 |

TABLE 9-continued

List of olfactory receptor genes in which the expression was changed by more than 2-fold change due to diet-induced obesity (8 weeks) in subcutaneous fat tissue

| GenBank accession No. | Gene name (Gene symbol) | Expression fold change to HFD group |
|---|---|---|
| NM_020514 | olfactory receptor 1509(Olfr1509) | 0.5 |
| NM_019476 | olfactory receptor 159(Olfr159) | 0.5 |
| NM_146997 | olfactory receptor 178(Olfr178) | 0.5 |
| NM_146322 | olfactory receptor 187(Olfr187) | 0.3 |
| NM_146992 | olfactory receptor 204(Olfr204) | 0.3 |
| NM_146443 | olfactory receptor 382(Olfr382) | 0.5 |
| NM_146576 | olfactory receptor 459(Olfr459) | 0.4 |
| NM_146426 | olfactory receptor 469(Olfr469) | 0.5 |
| NM_146495 | olfactory receptor 474(Olfr474) | 0.5 |
| NM_020291 | olfactory receptor 480(Olfr480) | 0.4 |
| NM_147046 | olfactory receptor 600(Olfr600) | 0.5 |
| NM_147069 | olfactory receptor 686(Olfr686) | 0.4 |
| NM_146547 | olfactory receptor 771(Olfr771) | 0.5 |
| NM_146548 | olfactory receptor 800(Olfr800) | 0.4 |
| NM_146567 | olfactory receptor 843(Olfr843) | 0.2 |
| NM_146522 | olfactory receptor 854(Olfr854) | 0.4 |
| NM_146868 | olfactory receptor 894(Olfr894) | 0.5 |
| NM_146272 | olfactory receptor 930(Olfr930) | 0.4 |
| NM_146745 | olfactory receptor 957(Olfr957) | 0.5 |

TABLE 10

List of olfactory receptor genes in which the expression was changed by more than 2-fold change due to diet-induced obesity (12 weeks) in subcutaneous fat tissue

| GenBank accession No. | Gene name (Gene symbol) | Expression fold change to HFD group |
|---|---|---|
| NM_146921 | olfactory receptor 1(Olfr1) | 2.1 |
| NM_146570 | olfactory receptor 1006(Olfr1006) | 2.2 |
| NM_207142 | olfactory receptor 1036(Olfr1036) | 2.0 |
| NM_207563 | olfactory receptor 1057(Olfr1057) | 2.4 |
| XM_619779 | olfactory receptor 1060(Olfr1060) | 2.2 |
| NM_146365 | olfactory receptor 1094(Olfr1094) | 2.5 |
| NM_001011734 | olfactory receptor 1116(Olfr1116) | 2.1 |
| NM_146351 | olfactory receptor 1133(Olfr1133) | 2.9 |
| NM_146645 | olfactory receptor 1158(Olfr1158) | 2.1 |
| NM_146848 | olfactory receptor 1161(Olfr1161) | 2.6 |
| NM_146644 | olfactory receptor 1163(Olfr1163) | 2.2 |
| NM_207566 | olfactory receptor 1173(Olfr1173) | 2.7 |
| XM_621554 | olfactory receptor 1174(Olfr1174) | 2.5 |
| NM_001011868 | olfactory receptor 1178(Olfr1178) | 4.4 |
| NM_146895 | olfactory receptor 1201(Olfr1201) | 2.1 |
| NM_146462 | olfactory receptor 1202(Olfr1202) | 2.4 |
| NM_146629 | olfactory receptor 121(Olfr121) | 2.2 |
| NM_207140 | olfactory receptor 1212(Olfr1212) | 2.7 |
| NM_146902 | olfactory receptor 1221(Olfr1221) | 2.6 |
| NM_146970 | olfactory receptor 1239(Olfr1239) | 2.1 |
| NM_146808 | olfactory receptor 1240(Olfr1240) | 2.2 |
| NM_146985 | olfactory receptor 1270(Olfr1270) | 2.1 |
| NM_207236 | olfactory receptor 1283(Olfr1283) | 2.5 |
| NM_146888 | olfactory receptor 1297(Olfr1297) | 3.5 |
| NM_146884 | olfactory receptor 1299(Olfr1299) | 2.3 |
| NM_146887 | olfactory receptor 1301(Olfr1301) | 2.0 |
| NM_001011870 | olfactory receptor 1329(Olfr1329) | 2.1 |
| NM_146831 | olfactory receptor 133(Olfr133) | 3.0 |
| NM_146916 | olfactory receptor 1346(Olfr1346) | 2.2 |
| NM_146389 | olfactory receptor 1350(Olfr1350) | 2.4 |
| NM_146936 | olfactory receptor 1417(Olfr1417) | 2.2 |
| NM_146699 | olfactory receptor 1445(Olfr1445) | 2.2 |
| NM_146691 | olfactory receptor 1467(Olfr1467) | 3.1 |
| NM_146696 | olfactory receptor 1477(Olfr1477) | 3.5 |
| NM_146992 | olfactory receptor 204(Olfr204) | 4.8 |
| NM_001001809 | olfactory receptor 218(Olfr218) | 2.2 |
| NM_001005780 | olfactory receptor 255(Olfr255) | 2.1 |
| NM_146688 | olfactory receptor 262(Olfr262) | 2.2 |
| NM_146489 | olfactory receptor 266(Olfr266) | 2.2 |
| NM_146824 | olfactory receptor 273(Olfr273) | 2.3 |
| NM_146938 | olfactory receptor 346(Olfr346) | 3.1 |
| NM_207235 | olfactory receptor 358(Olfr358) | 2.1 |
| NM_147051 | olfactory receptor 362(Olfr362) | 2.2 |
| NM_207555 | olfactory receptor 372(Olfr372) | 2.6 |
| NM_146825 | olfactory receptor 39(Olfr39) | 3.1 |
| NM_146347 | olfactory receptor 390(Olfr390) | 2.3 |
| NM_146963 | olfactory receptor 45(Olfr45) | 2.2 |
| NM_146576 | olfactory receptor 459(Olfr459) | 3.4 |
| NM_146411 | olfactory receptor 462(Olfr462) | 3.7 |
| NM_001005488 | olfactory receptor 467(Olfr467) | 3.8 |
| NM_146924 | olfactory receptor 476(Olfr476) | 2.0 |
| NM_146735 | olfactory receptor 483(Olfr483) | 2.0 |
| NM_146914 | olfactory receptor 5(Olfr5) | 2.3 |
| NM_146583 | olfactory receptor 52(Olfr52) | 3.7 |
| NM_001011867 | olfactory receptor 538(Olfr538) | 2.2 |
| NM_207621 | olfactory receptor 553(Olfr553) | 3.1 |
| NM_147041 | olfactory receptor 57(Olfr57) | 2.2 |
| NM_147110 | olfactory receptor 570(Olfr570) | 3.0 |
| NM_011002 | olfactory receptor 59(Olfr59) | 2.1 |
| NM_147070 | olfactory receptor 604(Olfr604) | 2.5 |
| NM_146964 | olfactory receptor 61(Olfr61) | 2.5 |
| NM_146727 | olfactory receptor 611(Olfr611) | 2.8 |
| NM_147120 | olfactory receptor 638(Olfr638) | 2.3 |
| NM_147049 | olfactory receptor 658(Olfr658) | 2.0 |
| NM_146814 | olfactory receptor 665(Olfr665) | 2.1 |
| NM_147096 | olfactory receptor 666(Olfr666) | 2.6 |
| NM_013620 | olfactory receptor 68(Olfr68) | 3.3 |
| NM_146453 | olfactory receptor 693(Olfr693) | 2.1 |
| NM_146597 | olfactory receptor 702(Olfr702) | 2.8 |
| NM_146604 | olfactory receptor 716(Olfr716) | 3.1 |
| NM_054090 | olfactory receptor 73(Olfr73) | 2.3 |
| NM_146363 | olfactory receptor 731(Olfr731) | 2.2 |
| NM_146422 | olfactory receptor 767(Olfr767) | 2.5 |
| NM_146339 | olfactory receptor 77(Olfr77) | 2.1 |
| NM_146863 | olfactory receptor 770(Olfr770) | 2.2 |
| NM_146266 | olfactory receptor 772(Olfr772) | 3.4 |
| NM_207008 | olfactory receptor 773, pseudogene 1(Olfr773-ps1) | 3.2 |
| NM_207620 | olfactory receptor 774(Olfr774) | 3.3 |
| NM_207559 | olfactory receptor 776(Olfr776) | 2.2 |
| NM_146933 | olfactory receptor 790(Olfr790) | 2.0 |
| NM_146930 | olfactory receptor 791(Olfr791) | 2.4 |
| NM_146554 | olfactory receptor 803(Olfr803) | 5.0 |
| NM_146555 | olfactory receptor 805(Olfr805) | 2.9 |
| NM_146776 | olfactory receptor 821(Olfr821) | 2.1 |
| NM_146605 | olfactory receptor 828(Olfr828) | 3.1 |
| NM_146904 | olfactory receptor 870(Olfr870) | 2.7 |
| NM_146477 | olfactory receptor 90(Olfr90) | 2.0 |
| NM_182714 | olfactory receptor 91(Olfr91) | 2.1 |
| NM_146746 | olfactory receptor 935(Olfr935) | 3.1 |
| NM_207141 | olfactory receptor 955(Olfr955) | 2.5 |
| NM_146330 | olfactory receptor 958(Olfr958) | 2.2 |
| NM_146826 | olfactory receptor 969(Olfr969) | 2.3 |
| NM_147107 | olfactory receptor 974(Olfr974) | 4.1 |
| NM_146917 | olfactory receptor 1179(Olfr1179) | 0.3 |
| NM_146896 | olfactory receptor 1203(Olfr1203) | 0.5 |
| NM_146968 | olfactory receptor 1242(Olfr1242) | 0.4 |
| NM_146982 | olfactory receptor 1257(Olfr1257) | 0.2 |
| NM_146341 | olfactory receptor 1259(Olfr1259) | 0.5 |
| NM_146794 | olfactory receptor 1263(Olfr1263) | 0.5 |
| NM_021368 | olfactory receptor 1264(Olfr1264) | 0.4 |
| NM_146327 | olfactory receptor 129(Olfr129) | 0.5 |
| NM_207631 | olfactory receptor 1321(Olfr1321) | 0.5 |
| NM_146308 | olfactory receptor 1356(Olfr1356) | 0.4 |
| NM_146490 | olfactory receptor 1411(Olfr1411) | 0.2 |
| NM_001011839 | olfactory receptor 1437(Olfr1437) | 0.5 |
| NM_146683 | olfactory receptor 1441(Olfr1441) | 0.5 |
| NM_146702 | olfactory receptor 1444(Olfr1444) | 0.3 |
| NM_146313 | olfactory receptor 145(Olfr145) | 0.4 |
| NM_146990 | olfactory receptor 1494(Olfr1494) | 0.4 |
| NM_146770 | olfactory receptor 259(Olfr259) | 0.5 |

TABLE 10-continued

List of olfactory receptor genes in which the expression was changed by more than 2-fold change due to diet-induced obesity (12 weeks) in subcutaneous fat tissue

| GenBank accession No. | Gene name (Gene symbol) | Expression fold change to HFD group |
|---|---|---|
| NM_147036 | olfactory receptor 283(Olfr283) | 0.5 |
| NM_146950 | olfactory receptor 341(Olfr341) | 0.4 |
| NM_147004 | olfactory receptor 399(Olfr399) | 0.4 |
| NM_146364 | olfactory receptor 495(Olfr495) | 0.4 |
| NM_147114 | olfactory receptor 575(Olfr575) | 0.5 |
| NM_147109 | olfactory receptor 577(Olfr577) | 0.4 |
| NM_207556 | olfactory receptor 592(Olfr592) | 0.4 |
| NM_147081 | olfactory receptor 610(Olfr610) | 0.4 |
| NM_147072 | olfactory receptor 641(Olfr641) | 0.5 |
| NM_146760 | olfactory receptor 672(Olfr672) | 0.4 |
| NM_146665 | olfactory receptor 732(Olfr732) | 0.3 |
| NM_146481 | olfactory receptor 890(Olfr890) | 0.5 |
| NM_146478 | olfactory receptor 891(Olfr891) | 0.5 |
| NM_146868 | olfactory receptor 894(Olfr894) | 0.5 |

TABLE 11

List of olfactory receptor genes in which the expression was changed by more than 2-fold change due to diet-induced obesity (2 weeks) in muscular tissue

| GenBank accession No. | Gene name (Gene symbol) | Expression fold change to HFD group |
|---|---|---|
| NM_147013 | olfactory receptor 1038(Olfr1038) | 2.1 |
| NM_146768 | olfactory receptor 1099(Olfr1099) | 2.4 |
| NM_146348 | olfactory receptor 1121(Olfr1121) | 2.2 |
| NM_146287 | olfactory receptor 114(Olfr114) | 2.7 |
| NM_146638 | olfactory receptor 1151(Olfr1151) | 2.1 |
| NM_207567 | olfactory receptor 1198(Olfr1198) | 2.2 |
| NM_146792 | olfactory receptor 1246(Olfr1246) | 2.7 |
| NM_146400 | olfactory receptor 1288(Olfr1288) | 2.5 |
| NM_207240 | olfactory receptor 1320(Olfr1320) | 2.3 |
| NM_207132 | olfactory receptor 1471(Olfr1471) | 2.6 |
| NM_146291 | olfactory receptor 1484(Olfr1484) | 2.6 |
| NM_207664 | olfactory receptor 151(Olfr151) | 2.3 |
| NM_019476 | olfactory receptor 159(Olfr159) | 2.8 |
| NM_146923 | olfactory receptor 20(Olfr20) | 3.3 |
| NM_001011789 | olfactory receptor 222(Olfr222) | 2.9 |
| NM_147051 | olfactory receptor 362(Olfr362) | 2.4 |
| NM_147009 | olfactory receptor 389(Olfr389) | 2.5 |
| NM_146825 | olfactory receptor 39(Olfr39) | 2.0 |
| NM_146761 | olfactory receptor 414(Olfr414) | 3.1 |
| NM_146924 | olfactory receptor 476(Olfr476) | 2.6 |
| NM_147112 | olfactory receptor 559(Olfr559) | 2.0 |
| NM_147122 | olfactory receptor 623(Olfr623) | 2.0 |
| NM_147069 | olfactory receptor 686(Olfr686) | 2.2 |
| NM_147035 | olfactory receptor 711(Olfr711) | 2.1 |
| NM_146666 | olfactory receptor 736(Olfr736) | 2.9 |
| NM_054091 | olfactory receptor 74(Olfr74) | 2.0 |
| NM_146285 | olfactory receptor 801(Olfr801) | 2.3 |
| NM_146566 | olfactory receptor 830(Olfr830) | 2.0 |
| NM_146921 | olfactory receptor 1(Olfr1) | 0.2 |
| NM_207673 | olfactory receptor 100(Olfr100) | 0.2 |
| NM_146578 | olfactory receptor 1033(Olfr1033) | 0.3 |
| NM_147012 | olfactory receptor 1047(Olfr1047) | 0.4 |
| NM_146835 | olfactory receptor 109(Olfr109) | 0.4 |
| NM_001013575 | olfactory receptor 112(Olfr112) | 0.5 |
| NM_146837 | olfactory receptor 1126(Olfr1126) | 0.4 |
| NM_146647 | olfactory receptor 1154(Olfr1154) | 0.4 |
| NM_001011535 | olfactory receptor 1182(Olfr1182) | 0.5 |
| NM_146895 | olfactory receptor 1201(Olfr1201) | 0.5 |
| NM_146891 | olfactory receptor 1225(Olfr1225) | 0.5 |
| NM_146965 | olfactory receptor 1250(Olfr1250) | 0.2 |
| NM_146907 | olfactory receptor 1282(Olfr1282) | 0.4 |
| XM_888068 | olfactory receptor 1293(Olfr1293) | 0.4 |
| NM_146886 | olfactory receptor 1298(Olfr1298) | 0.4 |
| NM_146449 | olfactory receptor 1310(Olfr1310) | 0.4 |

TABLE 11-continued

List of olfactory receptor genes in which the expression was changed by more than 2-fold change due to diet-induced obesity (2 weeks) in muscular tissue

| GenBank accession No. | Gene name (Gene symbol) | Expression fold change to HFD group |
|---|---|---|
| NM_146713 | olfactory receptor 1342(Olfr1342) | 0.5 |
| NM_146916 | olfactory receptor 1346(Olfr1346) | 0.5 |
| NM_146385 | olfactory receptor 1347(Olfr1347) | 0.4 |
| NM_146543 | olfactory receptor 1360(Olfr1360) | 0.4 |
| NM_146809 | olfactory receptor 1426(Olfr1426) | 0.2 |
| NM_146694 | olfactory receptor 1466(Olfr1466) | 0.4 |
| NM_146695 | olfactory receptor 1469(Olfr1469) | 0.4 |
| NM_146271 | olfactory receptor 1511(Olfr1511) | 0.5 |
| NM_146321 | olfactory receptor 186(Olfr186) | 0.4 |
| NM_001011736 | olfactory receptor 205(Olfr205) | 0.5 |
| NM_146950 | olfactory receptor 341(Olfr341) | 0.5 |
| NM_146627 | olfactory receptor 350(Olfr350) | 0.5 |
| NM_146368 | olfactory receptor 361(Olfr361) | 0.5 |
| NM_146718 | olfactory receptor 430(Olfr430) | 0.5 |
| NM_146963 | olfactory receptor 45(Olfr45) | 0.4 |
| NM_146383 | olfactory receptor 460(Olfr460) | 0.4 |
| NM_146738 | olfactory receptor 497(Olfr497) | 0.4 |
| NM_147041 | olfactory receptor 57(Olfr57) | 0.3 |
| NM_146727 | olfactory receptor 611(Olfr611) | 0.5 |
| NM_146820 | olfactory receptor 655(Olfr655) | 0.2 |
| NM_146600 | olfactory receptor 700(Olfr700) | 0.5 |
| NM_001011797 | olfactory receptor 782(Olfr782) | 0.4 |
| NM_207201 | olfactory receptor 8(Olfr8) | 0.4 |
| NM_146550 | olfactory receptor 810(Olfr810) | 0.4 |
| NM_146670 | olfactory receptor 815(Olfr815) | 0.3 |
| NM_146672 | olfactory receptor 816(Olfr816) | 0.4 |
| NM_001012266 | olfactory receptor 835(Olfr835) | 0.2 |
| NM_146557 | olfactory receptor 869(Olfr869) | 0.4 |
| NM_146561 | olfactory receptor 873(Olfr873) | 0.4 |
| NM_146336 | olfactory receptor 893(Olfr893) | 0.5 |
| NM_146811 | olfactory receptor 910(Olfr910) | 0.4 |
| NM_146810 | olfactory receptor 912(Olfr912) | 0.2 |
| NM_146440 | olfactory receptor 919(Olfr919) | 0.4 |
| NM_146507 | olfactory receptor 944(Olfr944) | 0.5 |
| NM_001011826 | olfactory receptor 967(Olfr967) | 0.5 |

TABLE 12

List of olfactory receptor genes in which the expression was changed by more than 2-fold change due to diet-induced obesity (4 weeks) in muscular tissue

| GenBank accession No. | Gene name (Gene symbol) | Expression fold change to HFD group |
|---|---|---|
| NM_147014 | olfactory receptor 1048(Olfr1048) | 2.4 |
| NM_147018 | olfactory receptor 1056(Olfr1056) | 2.1 |
| NM_146637 | olfactory receptor 1141(Olfr1141) | 2.3 |
| NM_146320 | olfactory receptor 1145(Olfr1145) | 2.1 |
| NM_146462 | olfactory receptor 1202(Olfr1202) | 2.2 |
| NM_146902 | olfactory receptor 1221(Olfr1221) | 2.3 |
| NM_146789 | olfactory receptor 1230(Olfr1230) | 2.1 |
| NM_146402 | olfactory receptor 1303(Olfr1303) | 2.0 |
| NM_146337 | olfactory receptor 1396(Olfr1396) | 2.6 |
| NM_146705 | olfactory receptor 1451(Olfr1451) | 2.2 |
| NM_207132 | olfactory receptor 1471(Olfr1471) | 2.5 |
| NM_146431 | olfactory receptor 1510(Olfr1510) | 2.6 |
| NM_010970 | olfactory receptor 23(Olfr23) | 2.2 |
| NM_146269 | olfactory receptor 247(Olfr247) | 3.0 |
| NM_146537 | olfactory receptor 311(Olfr311) | 2.4 |
| NM_146502 | olfactory receptor 328(Olfr328) | 2.2 |
| NM_146940 | olfactory receptor 352(Olfr352) | 2.3 |
| NM_146622 | olfactory receptor 360(Olfr360) | 2.2 |
| NM_147051 | olfactory receptor 362(Olfr362) | 3.0 |
| NM_146662 | olfactory receptor 365(Olfr365) | 2.9 |
| NM_146305 | olfactory receptor 420(Olfr420) | 2.1 |
| NM_146711 | olfactory receptor 43(Olfr43) | 2.5 |
| NM_146364 | olfactory receptor 495(Olfr495) | 2.1 |

TABLE 12-continued

List of olfactory receptor genes in which the expression was changed by more than 2-fold change due to diet-induced obesity (4 weeks) in muscular tissue

| GenBank accession No. | Gene name (Gene symbol) | Expression fold change to HFD group |
|---|---|---|
| NM_146743 | olfactory receptor 507(Olfr507) | 2.3 |
| NM_146755 | olfactory receptor 551(Olfr551) | 2.6 |
| NM_146359 | olfactory receptor 564(Olfr564) | 2.1 |
| NM_147091 | olfactory receptor 568(Olfr568) | 2.1 |
| NM_147081 | olfactory receptor 610(Olfr610) | 2.0 |
| NM_147074 | olfactory receptor 653(Olfr653) | 2.4 |
| NM_146285 | olfactory receptor 801(Olfr801) | 2.5 |
| NM_146932 | olfactory receptor 802(Olfr802) | 2.6 |
| NM_146904 | olfactory receptor 870(Olfr870) | 2.1 |
| NM_146375 | olfactory receptor 918(Olfr918) | 2.3 |
| NM_146610 | olfactory receptor 972(Olfr972) | 2.2 |
| NM_146827 | olfactory receptor 983(Olfr983) | 2.4 |
| NM_207673 | olfactory receptor 100(Olfr100) | 0.4 |
| NM_146569 | olfactory receptor 1014(Olfr1014) | 0.5 |
| NM_147015 | olfactory receptor 1019(Olfr1019) | 0.4 |
| NM_147010 | olfactory receptor 1052(Olfr1052) | 0.5 |
| XM_619779 | olfactory receptor 1060(Olfr1060) | 0.5 |
| NM_146511 | olfactory receptor 107(Olfr107) | 0.3 |
| NM_146592 | olfactory receptor 1086(Olfr1086) | 0.4 |
| NM_146365 | olfactory receptor 1094(Olfr1094) | 0.5 |
| NM_146594 | olfactory receptor 1100(Olfr1100) | 0.4 |
| NM_146289 | olfactory receptor 113(Olfr113) | 0.3 |
| NM_146351 | olfactory receptor 1133(Olfr1133) | 0.5 |
| NM_146641 | olfactory receptor 1164(Olfr1164) | 0.4 |
| NM_146532 | olfactory receptor 1170(Olfr1170) | 0.3 |
| NM_146458 | olfactory receptor 1199(Olfr1199) | 0.4 |
| NM_146896 | olfactory receptor 1203(Olfr1203) | 0.5 |
| NM_146794 | olfactory receptor 1263(Olfr1263) | 0.5 |
| NM_146395 | olfactory receptor 1276(Olfr1276) | 0.4 |
| NM_146887 | olfactory receptor 1301(Olfr1301) | 0.5 |
| NM_146867 | olfactory receptor 131(Olfr131) | 0.4 |
| NM_146471 | olfactory receptor 1393(Olfr1393) | 0.5 |
| NM_146809 | olfactory receptor 1426(Olfr1426) | 0.2 |
| NM_146702 | olfactory receptor 1444(Olfr1444) | 0.4 |
| NM_146291 | olfactory receptor 1484(Olfr1484) | 0.5 |
| NM_147001 | olfactory receptor 172(Olfr172) | 0.4 |
| NM_146993 | olfactory receptor 176(Olfr176) | 0.5 |
| NM_146999 | olfactory receptor 181(Olfr181) | 0.5 |
| NM_001011791 | olfactory receptor 193(Olfr193) | 0.2 |
| NM_146484 | olfactory receptor 197(Olfr197) | 0.5 |
| NM_146384 | olfactory receptor 208(Olfr208) | 0.5 |
| NM_146489 | olfactory receptor 266(Olfr266) | 0.4 |
| NM_146617 | olfactory receptor 307(Olfr307) | 0.4 |
| NM_146944 | olfactory receptor 348(Olfr348) | 0.5 |
| NM_146717 | olfactory receptor 433(Olfr433) | 0.5 |
| NM_146830 | olfactory receptor 44(Olfr44) | 0.4 |
| NM_146655 | olfactory receptor 441(Olfr441) | 0.4 |
| NM_146656 | olfactory receptor 444(Olfr444) | 0.4 |
| NM_146963 | olfactory receptor 45(Olfr45) | 0.5 |
| NM_146426 | olfactory receptor 469(Olfr469) | 0.4 |
| NM_146737 | olfactory receptor 494(Olfr494) | 0.3 |
| NM_146738 | olfactory receptor 497(Olfr497) | 0.5 |
| NM_146307 | olfactory receptor 498(Olfr498) | 0.4 |
| NM_146725 | olfactory receptor 516(Olfr516) | 0.4 |
| NM_146960 | olfactory receptor 53(Olfr53) | 0.5 |
| NM_147088 | olfactory receptor 569(Olfr569) | 0.5 |
| NM_001011793 | olfactory receptor 598(Olfr598) | 0.5 |
| NM_146959 | olfactory receptor 631(Olfr631) | 0.4 |
| NM_146598 | olfactory receptor 695(Olfr695) | 0.5 |
| NM_001011862 | olfactory receptor 699(Olfr699) | 0.4 |
| NM_146430 | olfactory receptor 742(Olfr742) | 0.2 |
| NM_001011797 | olfactory receptor 782(Olfr782) | 0.5 |
| NM_146548 | olfactory receptor 800(Olfr800) | 0.5 |
| NM_146554 | olfactory receptor 803(Olfr803) | 0.3 |
| NM_146525 | olfactory receptor 847(Olfr847) | 0.4 |
| NM_146557 | olfactory receptor 869(Olfr869) | 0.4 |
| NM_146419 | olfactory receptor 883(Olfr883) | 0.5 |
| NM_146481 | olfactory receptor 890(Olfr890) | 0.1 |
| NM_146477 | olfactory receptor 90(Olfr90) | 0.5 |
| NM_146811 | olfactory receptor 910(Olfr910) | 0.4 |
| BC051435 | olfactory receptor 947(Olfr947) | 0.5 |
| NM_146613 | olfactory receptor 973(Olfr973) | 0.5 |

TABLE 13

List of olfactory receptor genes in which the expression was changed by more than 2-fold change due to diet-induced obesity (8 weeks) in muscular tissue

| GenBank accession No. | Gene name (Gene symbol) | Expression fold change to HFD group |
|---|---|---|
| NM_146921 | olfactory receptor 1(Olfr1) | 5.5 |
| NM_147011 | olfactory receptor 1044(Olfr1044) | 2.1 |
| NM_147078 | olfactory receptor 1062(Olfr1062) | 2.8 |
| NM_146408 | olfactory receptor 1065(Olfr1065) | 2.3 |
| NM_146847 | olfactory receptor 1090(Olfr1090) | 2.4 |
| NM_146366 | olfactory receptor 1093(Olfr1093) | 2.3 |
| NM_146768 | olfactory receptor 1099(Olfr1099) | 2.7 |
| NM_146766 | olfactory receptor 1109(Olfr1109) | 3.4 |
| NM_146287 | olfactory receptor 114(Olfr114) | 2.1 |
| XM_621554 | olfactory receptor 1174(Olfr1174) | 2.0 |
| NM_146823 | olfactory receptor 1184(Olfr1184) | 2.4 |
| NM_146464 | olfactory receptor 1196(Olfr1196) | 2.8 |
| NM_207567 | olfactory receptor 1198(Olfr1198) | 2.0 |
| NM_207140 | olfactory receptor 1212(Olfr1212) | 2.5 |
| NM_146792 | olfactory receptor 1246(Olfr1246) | 2.6 |
| NM_001005568 | olfactory receptor 1281(Olfr1281) | 2.1 |
| XM_888068 | olfactory receptor 1293(Olfr1293) | 2.8 |
| NM_146652 | olfactory receptor 13(Olfr13) | 2.0 |
| NM_146402 | olfactory receptor 1303(Olfr1303) | 4.1 |
| NM_146913 | olfactory receptor 1348(Olfr1348) | 2.8 |
| NM_207571 | olfactory receptor 1355(Olfr1355) | 3.1 |
| NM_001011775 | olfactory receptor 1419(Olfr1419) | 2.4 |
| NM_146984 | olfactory receptor 142(Olfr142) | 2.1 |
| NM_207575 | olfactory receptor 1480(Olfr1480) | 2.0 |
| NM_146860 | olfactory receptor 161(Olfr161) | 3.2 |
| NM_147000 | olfactory receptor 173(Olfr173) | 2.1 |
| NM_207553 | olfactory receptor 251(Olfr251) | 2.2 |
| NM_146945 | olfactory receptor 345(Olfr345) | 2.1 |
| NM_146940 | olfactory receptor 352(Olfr352) | 2.3 |
| NM_146368 | olfactory receptor 361(Olfr361) | 2.3 |
| NM_146662 | olfactory receptor 365(Olfr365) | 3.5 |
| NM_146338 | olfactory receptor 374(Olfr374) | 2.2 |
| NM_146347 | olfactory receptor 390(Olfr390) | 2.0 |
| NM_147005 | olfactory receptor 395(Olfr395) | 2.1 |
| NM_207622 | olfactory receptor 403(Olfr403) | 2.6 |
| NM_146711 | olfactory receptor 43(Olfr43) | 2.2 |
| NM_146934 | olfactory receptor 46(Olfr46) | 2.2 |
| NM_146383 | olfactory receptor 460(Olfr460) | 2.6 |
| NM_146370 | olfactory receptor 47(Olfr47) | 2.1 |
| NM_146734 | olfactory receptor 478(Olfr478) | 2.9 |
| NM_146364 | olfactory receptor 495(Olfr495) | 2.4 |
| NM_146583 | olfactory receptor 52(Olfr52) | 2.2 |
| NM_146964 | olfactory receptor 61(Olfr61) | 2.6 |
| NM_147083 | olfactory receptor 622(Olfr622) | 2.4 |
| NM_207146 | olfactory receptor 670(Olfr670) | 2.3 |
| NM_147032 | olfactory receptor 705(Olfr705) | 3.0 |
| NM_146278 | olfactory receptor 729(Olfr729) | 2.4 |
| NM_207133 | olfactory receptor 741(Olfr741) | 2.1 |
| NM_207156 | olfactory receptor 747(Olfr747) | 2.6 |
| NM_146929 | olfactory receptor 807(Olfr807) | 2.1 |
| NM_146324 | olfactory receptor 809(Olfr809) | 2.0 |
| NM_146564 | olfactory receptor 836(Olfr836) | 3.8 |
| NM_146527 | olfactory receptor 849(Olfr849) | 2.0 |
| NM_001011748 | olfactory receptor 867(Olfr867) | 2.5 |
| NM_146417 | olfactory receptor 877(Olfr877) | 3.1 |
| NM_146375 | olfactory receptor 918(Olfr918) | 2.2 |

TABLE 13-continued

List of olfactory receptor genes in which the expression was changed by more than 2-fold change due to diet-induced obesity (8 weeks) in muscular tissue

| GenBank accession No. | Gene name (Gene symbol) | Expression fold change to HFD group |
|---|---|---|
| NM_146272 | olfactory receptor 930(Olfr930) | 2.3 |
| NM_147108 | olfactory receptor 979(Olfr979) | 2.1 |
| NM_146865 | olfactory receptor 992(Olfr992) | 2.7 |
| NM_207673 | olfactory receptor 100(Olfr100) | 0.4 |
| NM_146637 | olfactory receptor 1141(Olfr1141) | 0.3 |
| NM_146971 | olfactory receptor 1228(Olfr1228) | 0.5 |
| NM_146713 | olfactory receptor 1342(Olfr1342) | 0.4 |
| NM_146410 | olfactory receptor 1420(Olfr1420) | 0.3 |
| NM_146747 | olfactory receptor 146(Olfr146) | 0.5 |
| NM_019475 | olfactory receptor 157(Olfr157) | 0.5 |
| NM_146446 | olfactory receptor 215(Olfr215) | 0.4 |
| NM_146830 | olfactory receptor 44(Olfr44) | 0.3 |
| NM_146751 | olfactory receptor 648(Olfr648) | 0.4 |
| NM_147043 | olfactory receptor 669(Olfr669) | 0.4 |
| NM_146596 | olfactory receptor 703(Olfr703) | 0.5 |
| NM_207145 | olfactory receptor 845(Olfr845) | 0.3 |

TABLE 14

List of olfactory receptor genes in which the expression was changed by more than 2-fold change due to diet-induced obesity (12 weeks) in muscular tissue

| GenBank accession No. | Gene name (Gene symbol) | Expression fold change to HFD group |
|---|---|---|
| NM_146569 | olfactory receptor 1014(Olfr1014) | 2.1 |
| NM_146833 | olfactory receptor 103(Olfr103) | 2.1 |
| XM_619779 | olfactory receptor 1060(Olfr1060) | 2.9 |
| NM_146406 | olfactory receptor 1076(Olfr1076) | 2.2 |
| NM_146407 | olfactory receptor 1079(Olfr1079) | 2.4 |
| NM_146409 | olfactory receptor 1080(Olfr1080) | 2.7 |
| NM_146590 | olfactory receptor 1085(Olfr1085) | 2.1 |
| NM_146730 | olfactory receptor 1095(Olfr1095) | 2.1 |
| NM_146591 | olfactory receptor 1101(Olfr1101) | 2.4 |
| NM_207154 | olfactory receptor 1102(Olfr1102) | 3.1 |
| NM_146838 | olfactory receptor 1130(Olfr1130) | 3.3 |
| NM_146293 | olfactory receptor 1143(Olfr1143) | 2.3 |
| NM_146640 | olfactory receptor 1153(Olfr1153) | 3.5 |
| NM_146644 | olfactory receptor 1163(Olfr1163) | 2.1 |
| NM_146808 | olfactory receptor 1240(Olfr1240) | 3.0 |
| NM_146788 | olfactory receptor 1245(Olfr1245) | 2.6 |
| NM_146343 | olfactory receptor 1265(Olfr1265) | 2.2 |
| NM_146333 | olfactory receptor 1274(Olfr1274) | 3.2 |
| NM_146765 | olfactory receptor 1290(Olfr1290) | 2.2 |
| NM_146886 | olfactory receptor 1298(Olfr1298) | 2.3 |
| NM_207151 | olfactory receptor 1308(Olfr1308) | 2.1 |
| NM_207253 | olfactory receptor 1371(Olfr1371) | 2.2 |
| NM_146337 | olfactory receptor 1396(Olfr1396) | 2.5 |
| NM_001011775 | olfactory receptor 1419(Olfr1419) | 2.2 |
| NM_146680 | olfactory receptor 1423(Olfr1423) | 2.6 |
| NM_146697 | olfactory receptor 1442(Olfr1442) | 2.1 |
| NM_020513 | olfactory receptor 1508(Olfr1508) | 3.4 |
| NM_001005524 | olfactory receptor 194(Olfr194) | 2.7 |
| NM_010983 | olfactory receptor 2(Olfr2) | 2.0 |
| NM_207230 | olfactory receptor 320(Olfr320) | 2.5 |
| NM_001011861 | olfactory receptor 331(Olfr331) | 2.9 |
| NM_146940 | olfactory receptor 352(Olfr352) | 3.3 |
| NM_147051 | olfactory receptor 362(Olfr362) | 2.6 |
| NM_146374 | olfactory receptor 368(Olfr368) | 2.2 |
| NM_207555 | olfactory receptor 372(Olfr372) | 2.4 |
| NM_146922 | olfactory receptor 376(Olfr376) | 3.1 |
| NM_146734 | olfactory receptor 478(Olfr478) | 2.1 |
| NM_147104 | olfactory receptor 550(Olfr550) | 2.1 |
| NM_147091 | olfactory receptor 568(Olfr568) | 2.9 |
| NM_001011847 | olfactory receptor 591(Olfr591) | 2.0 |
| NM_146813 | olfactory receptor 651(Olfr651) | 2.7 |
| NM_001011757 | olfactory receptor 663(Olfr663) | 2.3 |
| NM_207249 | olfactory receptor 684(Olfr684) | 2.3 |
| NM_146596 | olfactory receptor 703(Olfr703) | 2.2 |
| NM_146493 | olfactory receptor 730(Olfr730) | 2.4 |
| NM_146663 | olfactory receptor 733(Olfr733) | 2.1 |
| NM_146862 | olfactory receptor 763(Olfr763) | 2.2 |
| NM_130866 | olfactory receptor 78(Olfr78) | 2.0 |
| NM_146555 | olfactory receptor 805(Olfr805) | 2.3 |
| NM_146550 | olfactory receptor 810(Olfr810) | 2.2 |
| NM_146905 | olfactory receptor 851(Olfr851) | 2.0 |
| NM_146528 | olfactory receptor 860(Olfr860) | 2.1 |
| NM_146418 | olfactory receptor 881(Olfr881) | 2.0 |
| NM_146423 | olfactory receptor 887(Olfr887) | 2.3 |
| NM_146478 | olfactory receptor 891(Olfr891) | 2.4 |
| NM_146279 | olfactory receptor 960(Olfr960) | 2.3 |
| NM_207673 | olfactory receptor 100(Olfr100) | 0.5 |
| NM_146589 | olfactory receptor 1022(Olfr1022) | 0.5 |
| NM_207562 | olfactory receptor 1051(Olfr1051) | 0.4 |
| NM_146843 | olfactory receptor 1097(Olfr1097) | 0.4 |
| NM_146768 | olfactory receptor 1099(Olfr1099) | 0.5 |
| NM_146594 | olfactory receptor 1100(Olfr1100) | 0.5 |
| NM_147028 | olfactory receptor 1125(Olfr1125) | 0.3 |
| NM_146637 | olfactory receptor 1141(Olfr1141) | 0.5 |
| XM_621555 | olfactory receptor 1175(Olfr1175) | 0.4 |
| NM_206896 | olfactory receptor 12(Olfr12) | 0.2 |
| XM_888068 | olfactory receptor 1293(Olfr1293) | 0.4 |
| NM_147040 | olfactory receptor 1351(Olfr1351) | 0.4 |
| NM_146534 | olfactory receptor 1368(Olfr1368) | 0.4 |
| NM_146303 | olfactory receptor 1449(Olfr1449) | 0.5 |
| NM_001011842 | olfactory receptor 1474(Olfr1474) | 0.5 |
| NM_146484 | olfactory receptor 197(Olfr197) | 0.5 |
| NM_146446 | olfactory receptor 215(Olfr215) | 0.5 |
| NM_207553 | olfactory receptor 251(Olfr251) | 0.4 |
| NM_146939 | olfactory receptor 354(Olfr354) | 0.2 |
| NM_207224 | olfactory receptor 386(Olfr386) | 0.5 |
| NM_147008 | olfactory receptor 393(Olfr393) | 0.4 |
| NM_146295 | olfactory receptor 446(Olfr446) | 0.5 |
| NM_146518 | olfactory receptor 523(Olfr523) | 0.4 |
| NM_147009 | olfactory receptor 630(Olfr630) | 0.3 |
| NM_147119 | olfactory receptor 632(Olfr632) | 0.4 |
| NM_146379 | olfactory receptor 654(Olfr654) | 0.5 |
| XM_993242 | olfactory receptor 664(Olfr664) | 0.3 |
| NM_147095 | olfactory receptor 676(Olfr676) | 0.5 |
| NM_147044 | olfactory receptor 679(Olfr679) | 0.5 |
| NM_146266 | olfactory receptor 772(Olfr772) | 0.4 |
| NM_146564 | olfactory receptor 836(Olfr836) | 0.4 |
| NM_207145 | olfactory receptor 845(Olfr845) | 0.4 |
| NM_146803 | olfactory receptor 906(Olfr906) | 0.4 |
| NM_146786 | olfactory receptor 914(Olfr914) | 0.4 |
| NM_146784 | olfactory receptor 916(Olfr916) | 0.5 |
| NM_001011864 | olfactory receptor 917(Olfr917) | 0.5 |
| NM_001011518 | olfactory receptor 94(Olfr94) | 0.4 |
| NM_146507 | olfactory receptor 944(Olfr944) | 0.4 |

C. Verification Using MNI Analysis Method for Profile of Olfactory Receptor Genes Responding to Diet-Induced Obesity DEG (differentially expressed gene) analysis method identifying genes in which the expression is changed by specific condition has been used for microarray data analysis method so far. Although DEG analysis method may establish profiles for thousands of genes in which the expression is changed by specific condition, there is a limitation that this method may not be identified target gene. To overcome this problem, MNI (mode-of-action by network identification) analysis method has been newly developed (Bernardo et al., Chemogenomic profiling on a genome-wide scale using reverse-engineered gene networks, *Nature Biotech-* nology 23: 377, 2005). Using this, studies for identifying target genes of various diseases and drugs have been reported.

Therefore, gene expression profile resulting from a variety of treatments in visceral fat, subcutaneous fat tissue and muscular tissue of mice with diet-induced obesity was analyzed using MNI method in the present study. As a result, the drug target ranking was evaluated based on the extent of escaping out on MNI gene network Algorithm by certain drug. The list of genes ranked within the top 200 and their DEG values were shown in Tables 15 and 16.

In visceral fat tissue, olfactory receptor genes ranked within the top 200 among genes responding to high-fat diet-induced obesity were 10 (2 weeks), 7 (4 weeks), 11 (8 weeks) and 10 (12 weeks). In subcutaneous fat tissue, olfactory receptor genes ranked within the top 200 among genes responding to high-fat diet-induced obesity were 8 (2 weeks), 9 (4 weeks), 11 (8 weeks) and 8 (12 weeks). In addition, in muscular tissue, olfactory receptor genes ranked within the top 200 among genes responding to high-fat diet-induced obesity were 12 (2 weeks), 11 (4 weeks), 15 (8 weeks) and 12 (12 weeks). Moreover, it would be appreciated that most of olfactory receptor genes of highly ranked MNI levels also showed high-expression fold change in DEG (Tables 15 and 16).

TABLE 15

List of olfactory receptor genes responding to diet-induced obesity (comparison of MNI rank and DEG expression fold change) in fat tissue

| | 2 weeks | | | 4 weeks | | | 8 weeks | | | 12 weeks | |
|---|---|---|---|---|---|---|---|---|---|---|---|
| Gene | MNI rank | DEG expression fold change | Gene | MNI rank | DEG expression fold change | Gene | MNI rank | DEG expression fold change | Gene | MNI rank | DEG expression fold change |
| | | | | | visceral fat tissue | | | | | | |
| Olfr513 | 6 | 0.26 | Olfr1181 | 3 | 5.47 | Olfr536 | 11 | 0.48 | Olfr16 | 6 | 2.33 |
| Olfr433 | 15 | 2.07 | Olfr513 | 27 | 0.3 | Olfr513 | 31 | 0.3 | Olfr715 | 24 | 3.77 |
| Olfr1245 | 29 | 2.4 | Olfr960 | 31 | 2.25 | Olfr654 | 37 | 2.83 | Olfr1000 | 29 | 3.01 |
| Olfr1143 | 36 | 2.21 | Olfr1245 | 43 | 1.93 | Olfr527 | 39 | 1.84 | Olfr1245 | 32 | 2.01 |
| Olfr867 | 54 | 1.86 | Olfr1143 | 121 | 2.23 | Olfr1000 | 52 | 2.47 | Olfr536 | 36 | 0.46 |
| Olfr996 | 55 | 5.8 | Olfr652 | 136 | 1.41 | Olfr652 | 99 | 1.56 | Olfr1143 | 52 | 2.26 |
| Olfr960 | 57 | 2.42 | Olfr1284 | 157 | 0.64 | Olfr960 | 106 | 2.09 | Olfr527 | 66 | 1.81 |
| Olfr1359 | 96 | 0.76 | | | | Olfr291 | 118 | 1.83 | Olfr652 | 108 | 1.37 |
| Olfr652 | 104 | 1.47 | | | | Olfr1143 | 119 | 2.24 | Olfr1284 | 187 | 0.67 |
| Olfr1284 | 122 | 0.67 | | | | Olfr1245 | 128 | 2.14 | Olfr1359 | 195 | 0.77 |
| | | | | | | Olfr1359 | 191 | 0.79 | | | |
| | | | | | subcutaneous fat tissue | | | | | | |
| Olfr1173 | 5 | 1.97 | Olfr855 | 2 | 1.57 | Olfr1056 | 3 | 0.73 | Olfr716 | 4 | 3.08 |
| Olfr823 | 9 | 0.55 | Olfr888 | 13 | 0.51 | Olfr960 | 15 | 1.68 | Olfr45 | 16 | 2.15 |
| Olfr855 | 11 | 1.71 | Olfr305 | 36 | 0.61 | Olfr685 | 19 | 0.71 | Olfr960 | 19 | 1.9 |
| Olfr411 | 49 | 1.53 | Olfr1173 | 49 | 2.29 | Olfr1408 | 26 | 0.67 | Olfr1173 | 32 | 2.69 |
| Olfr1408 | 51 | 0.58 | Olfr395 | 52 | 1.59 | Olfr855 | 35 | 1.98 | Olfr411 | 34 | 1.55 |
| Olfr875 | 64 | 0.6 | Olfr411 | 55 | 1.38 | Olfr609 | 42 | 0.55 | Olfr1408 | 43 | 0.67 |
| Olfr472 | 123 | 0.71 | Olfr823 | 83 | 0.57 | Olfr1173 | 49 | 1.93 | Olfr855 | 45 | 1.58 |
| Olfr125 | 143 | 0.73 | Olfr1408 | 89 | 0.62 | Olfr411 | 71 | 1.37 | Olfr875 | 96 | 0.59 |
| | | | Olfr1121 | 132 | 1.23 | Olfr305 | 91 | 0.59 | | | |
| | | | | | | Olfr1121 | 94 | 1.2 | | | |
| | | | | | | Olfr970 | 103 | 0.55 | | | |

TABLE 16

List of olfactory receptor genes responding to diet-induced obesity (comparison of MNI rank and DEG expression fold change) in muscular tissue

| | 2 weeks | | | 4 weeks | | | 8 weeks | | | 12 weeks | |
|---|---|---|---|---|---|---|---|---|---|---|---|
| Gene | MNI rank | DEG expression fold change | Gene | MNI rank | DEG expression fold change | Gene | MNI rank | DEG expression fold change | Gene | MNI rank | DEG expression fold change |
| | | | | | muscular tissue | | | | | | |
| Olfr232 | 13 | 0.6 | Olfr232 | 12 | 0.59 | Olfr232 | 10 | 0.62 | Olfr689 | 22 | 0.54 |
| Olfr739 | 14 | 0.55 | Olfr699 | 15 | 0.43 | Olfr872 | 37 | 1.89 | Olfr488 | 24 | 0.66 |
| Olfr488 | 40 | 0.62 | Olfr800 | 28 | 0.46 | Olfr739 | 48 | 0.65 | Olfr347 | 38 | 1.45 |
| Olfr474 | 55 | 0.83 | Olfr978 | 33 | 0.51 | Olfr1305 | 64 | 0.68 | Olfr1204 | 69 | 0.7 |
| Olfr685 | 79 | 1.33 | Olfr474 | 49 | 0.84 | Olfr1395 | 80 | 1.67 | Olfr685 | 82 | 1.26 |
| Olfr1116 | 83 | 1.23 | Olfr685 | 51 | 1.25 | Olfr140 | 81 | 1.43 | Olfr406 | 97 | 1.28 |
| Olfr538 | 95 | 1.74 | Olfr488 | 73 | 0.69 | Olfr63 | 85 | 0.74 | Olfr1105 | 102 | 1.4 |
| Olfr689 | 107 | 0.62 | Olfr538 | 83 | 1.72 | Olfr689 | 86 | 0.67 | Olfr63 | 119 | 0.72 |
| Olfr406 | 150 | 1.23 | Olfr689 | 112 | 0.67 | Olfr506 | 92 | 0.65 | Olfr509 | 149 | 0.57 |

TABLE 16-continued

List of olfactory receptor genes responding to diet-induced obesity (comparison of MNI rank and DEG expression fold change) in muscular tissue

| 2 weeks | | | 4 weeks | | 8 weeks | | | 12 weeks | | | |
|---|---|---|---|---|---|---|---|---|---|---|---|
| Gene | MNI rank | DEG expression fold change | Gene | Gene | MNI rank | DEG expression fold change muscular tissue | Gene | Gene | MNI rank | DEG expression fold change | Gene |
| Olfr1105 | 185 | 1.48 | Olfr1204 | 135 | 0.73 | Olfr975 | 101 | 1.51 | Olfr506 | 173 | 0.68 |
| Olfr483 | 190 | 1.24 | Olfr1105 | 152 | 1.46 | Olfr945 | 109 | 0.59 | Olfr1305 | 179 | 0.7 |
| Olfr509 | 196 | 0.59 | | | | Olfr685 | 115 | 1.22 | Olfr474 | 192 | 0.77 |
| | | | | | | Olfr474 | 124 | 0.79 | | | |
| | | | | | | Olfr943 | 145 | 0.72 | | | |
| | | | | | | Olfr406 | 183 | 1.24 | | | |

Example 2

Profile for Olfactory Receptors in which the Expression is Changed by Various Types of Odor Components Having Anti-Obesity Efficacy 1) Preparation of Test Diets and Maintenance of Test Animals The obesity-inducing control diet used in the test was high-fat diet (HFD: 40% fat calorie, 17 g lard+3% corn oil/100 g diet). Diets supplemented with an odor component had the same composition as HFD, except that each of various types of odor components (indol-3-carbinol, oleuropein, cedryl acetate, α-cedrene and piperine) having anti-obesity efficacy was contained in 0.02-0.05% concentration. Indo)-3-carbinol, oleuropein, cedryl acetate, a-cedrene and piperine were purchased from Sigma-Aldrich.

The odor component used in this experiment is a phytochemical present in various types of edible plants. It has been used as food additives (flavoring agents) at home and abroad. In addition, the present inventor has found that the odor component has effects for decreasing body weight and visceral fat, improving hyperlipidemia, non-alcoholic fatty liver and type 2 diabetes (insulin resistance).

3) OligoDNA Microarray Analysis for Visceral Fat and Liver Tissue

A. RNA Extraction and Verification

After adding Trizol agent to visceral fat or liver tissue, the mixture was homogenized and centrifuged at 12,000×g for 10 min at 4° C. The supernatant was transferred to a new tube to remove fat layer. Then, 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

B. OligoDNA Microarray Analysis

DNA microarray analysis using RNAs of visceral fat and liver tissue was conducted by GENOCHECK (CO., LTD.).

RNA samples were pooled from 10 mice in each experimental group and subjected to microarray experiments in triplicate for the test of reproducibility. NimbleGen Mouse Whole Oligo 12-plex chip used in this experiment was prepared by triplicating 42,576 genes using Mouse Genome Build 8 as database. In NimbleGen mouse Whole Oligo 12-plex chip, 137,090 spots excluded control group gene were spotted by 16 μm×16 μm size in 17.4 mm×13 mm size. 42,576 oligo included 137,145 genes which are known their functions and 5,431 transcripts and EST sequences which are unknown their functions. 10-50 μg of total RNA was added in oligo-dT primer, reverse transcriptase, dNTP, Cy3-dUTP and Cy5-dUTP, and reverse-transcripted according to the kit manufacturer's recommendations. The resultant was purified using cartridge, dried and dissolved in hybridization buffer solution (30 μL). The microarray was placed in hybridization cassette, heated at 95-100° C. for 5 min, mixed independently to each of RNA labeled with Cy3 and Cy5, and hybridized at 45° C. for 18 hrs. The slide was washed twice in solution containing 1×SSC and 0.1% SDS for 5 min, washed in 1×SSC for 5 min and dried to analyze.

C. Olfactory Receptor Profile in which the Expression was Changed by Odor Components Having Anti-Obesity Efficacy DNA microarray analysis conducted for visceral fat and liver tissue of mice which were fed diets supplemented with various types of odor components for 10 weeks and showed effects for decreasing body weight and visceral fat. The profile for olfactory receptors in which the expression was regulated by more than 2-fold change due to intake of odor components at each tissue was shown in Tables 5. As a result, it was determined that various types of odor components having anti-obesity efficacy regulated a plurality of olfactory receptors in peripheral tissues.

Indol-3-carbinol was supplemented to mouse fed the high-fat diet for 10 weeks. As a result, in visceral fat and liver tissues, expressions of olfactory receptor 909, 1462, 380, 1153, 116, 290 and 178 were increased by more than 2-fold change. In contrast, expressions of olfactory receptor 972, 1093, 1165,259, 1337, 466, 1329, 16, 1045, 196, 1216 and 686 were decreased by more than 2-fold change.

Oleuropein was supplemented to mouse fed the high-fat diet for 10 weeks. As a result, in visceral fat and liver tissues, expressions of olfactory receptor 1104, 971, 1447, 290, 520, 1046, 1317, 275, 38, 1204 and 1214 were increased by more than 2-fold change. In contrast, expressions of olfactory receptor 907, 341, 495 and 1136 were decreased by more than 2-fold change.

Cedryl acetate was supplemented to mouse fed the high-fat diet for 10 weeks. As a result, in visceral fat and liver tissues, expressions of olfactory receptor 1104, 1123, 290, 1058, 1442, 380, 1125, 663, 878, 275, 38 and 305 were increased by more than 2-fold change. In contrast, expressions of olfactory receptor 1157, 618, 1136, 417, 1165, 341 and 77 were decreased by more than 2-fold change.

Piperine was supplemented to mouse fed the high-fat diet for 10 weeks. As a result, in visceral fat and liver tissues, expressions of olfactory receptor 878, 38 and 520 were increased by more than 2-fold change. In contrast, expressions of olfactory receptor 1462 and 77 were decreased by more than 2-fold change.

α-cedrene was supplemented to mouse fed the high-fat diet for 10 weeks. As a result, in visceral fat and liver tissues, expressions of olfactory receptor 878, 38 and 1222 were increased by more than 2-fold change. In contrast, expression of olfactory receptor 1045 was decreased by more than 2-fold change.

Likewise, it was observed that certain olfactory receptor was commonly increased or decreased by various types of odor components, whereas various types of odor components having anti-obesity efficacy regulated a plurality of olfactory receptors in peripheral tissues. i.e., the expressions of olfactory receptor 878 and 38 were commonly increased by piperine, cedryl acetate, α-cedrene and oleuropein in liver tissue. The expression of olfactory receptor 275 was commonly increased by oleuropein and cedryl acetate in liver tissue. In contrast, the expression of olfactory receptor 77 was commonly decreased by piperine and cedryl acetate in liver tissue. The expression of olfactory receptor 1045 was commonly decreased by indol-3-carbinol and α-cedrene in liver tissue (Table 17). Meanwhile, the expression of olfactory receptor 380 was commonly increased by indol-3-carbinol and cedryl acetate in visceral fat tissue. The expressions of olfactory receptor 290 and 1104 were commonly increased by oleuropein and cedryl acetate in visceral fat tissue. In contrast, the expression of olfactory receptor 341 was commonly decreased by oleuropein and cedryl acetate in visceral fat tissue. The expression of olfactory receptor 1165 was commonly decreased by indol-3-carbinol and cedryl acetate in visceral fat tissue (Table 18).

Where olfactory receptors present in adipocytes, muscle cells and liver cell membranes bind to odor components having anti-obesity efficacy even under circumstance of non-regulation by gene expression, they transmit signals to $AC_3$ such that olfactory receptors may exhibit effects for accumulating fat, promoting fatty acid oxidation and thermogenesis, and improving insulin resistance. Therefore, olfactory receptor gene expression regulation by the intake of these odor components in peripheral tissues would be considered not a necessary condition but a sufficient condition demonstrating that the olfactory receptor may be a novel direct target for odor components having anti-obesity efficacy.

TABLE 17

Profile for olfactory receptors in which the expression is changed by anti-obesity substance

| GenBank accession No. | Gene name (Gene symbol) | Expression fold change to HFD group |
|---|---|---|
| Indole-3 carbinol (visceral fat tissue) | | |
| NM_146873 | Olfactory receptor 909 (Olfr909) | 3.45 |
| NM_146693 | Olfactory receptor 1462 (Olfr1462) | 2.26 |
| NM_147025 | Olfactory receptor 380 (Olfr380) | 2.20 |
| NM_146610 | Olfactory receptor 972 (Olfr972) | 0.43 |

TABLE 17-continued

Profile for olfactory receptors in which the expression is changed by anti-obesity substance

| GenBank accession No. | Gene name (Gene symbol) | Expression fold change to HFD group |
|---|---|---|
| NM_146366 | Olfactory receptor 1093 (Olfr1093) | 0.42 |
| NM_146648 | Olfactory receptor 1165 (Olfr1165) | 0.39 |
| Indole-3 carbinol (liver tissue) | | |
| NM_146640 | Olfactory receptor 1153 (Olfr1153) | 2.82 |
| NM_146632 | Olfactory receptor 116 (Olfr116) | 2.12 |
| NM_146416 | Olfactory receptor 290 (Olfr290) | 2.11 |
| NM_146997 | Olfactory receptor 178 (Olfr178) | 2.06 |
| NM_146770 | Olfactory receptor 259 (Olfr 259) | 0.50 |
| NM_146309 | Olfactory receptor 1337 (Olfr1337) | 0.49 |
| NM_146819 | Olfactory receptor 466 (Olfr466) | 0.49 |
| NM_001011870 | Olfactory receptor 1329 (Olfr1329) | 0.48 |
| NM_008763 | Olfactory receptor 16 (Olfr16) | 0.47 |
| NM_147017 | Olfactory receptor 1045 (Olfr1045) | 0.45 |
| NM_146779 | Olfactory receptor 196 (Olfr196) | 0.45 |
| NM_146893 | Olfactory receptor 1216 (Olfr1216) | 0.41 |
| NM_147069 | Olfactory receptor 686 (Olfr686) | 0.35 |
| Oleuropein (visceral fat tissue) | | |
| NM_146767 | Olfactory receptor 1104 (Olfr1104) | 4.39 |
| NM_146614 | Olfactory receptor 971 (Olfr971) | 2.37 |
| NM_146703 | Olfactory receptor 1447 (Olfr1447) | 2.33 |
| NM_146416 | Olfactory receptor 290 (Olfr290) | 2.32 |
| NM_147063 | Olfactory receptor 520 (Olfr520) | 2.08 |
| NM_146582 | Olfactory receptor 1046 (Olfr1046) | 2.01 |
| NM_146805 | Olfactory receptor 907 (Olfr907) | 0.49 |
| NM_146950 | Olfactory receptor 341 (Olfr341) | 0.30 |
| NM_146364 | Olfactory receptor 495 (Olfr495) | 0.21 |
| Oleuropein (liver tissue) | | |
| NM_146448 | Olfactory receptor 1317 (Olfr1317) | 2.89 |
| NM_146858 | Olfactory receptor 275 (Olfr275) | 2.49 |
| NM_146986 | Olfactory receptor 38 (Olfr38) | 2.35 |
| NM_146463 | Olfactory receptor 1204 (Olfr1204) | 2.21 |
| NM_146897 | Olfactory receptor 1214 (Olfr1214) | 2.17 |
| NM_146659 | Olfactory receptor 1136 (Olfr1136) | 0.49 |
| Cedryl acetate (visceral fat tissue) | | |
| NM_146767 | Olfactory receptor 1104 (Olfr1104) | 3.22 |
| NM_146350 | Olfactory receptor 1123 (Olfr1123) | 2.64 |
| NM_146416 | Olfactory receptor 290 (Olfr290) | 2.40 |
| NM_146391 | Olfactory receptor 1058 (Olfr1058) | 2.18 |
| NM_146697 | Olfactory receptor 1442 (Olfr1442) | 2.18 |
| NM_147025 | Olfactory receptor 380 (Olfr380) | 2.14 |
| NM_147028 | Olfactory receptor 1125 (Olfr1125) | 2.07 |
| NM_001011757 | Olfactory receptor 663 (Olfr663) | 2.04 |
| NM_146849 | Olfactory receptor 1157 (Olfr1157) | 0.46 |
| NM_147047 | Olfactory receptor 618 (Olfr618) | 0.43 |
| NM_146659 | Olfactory receptor 1136 (Olfr1136) | 0.43 |
| NM_207137 | Olfactory receptor 417 (Olfr417) | 0.42 |
| NM_146648 | Olfactory receptor 1165 (Olfr1165) | 0.36 |
| NM_146750 | Olfactory receptor 341 (Olfr341) | 0.32 |
| Cedryl acetate (liver tissue) | | |
| NM_146798 | Olfactory receptor 878 (Olfr878) | 2.76 |
| NM_146858 | Olfactory receptor 275 (Olfr275) | 2.64 |
| NM_146986 | Olfactory receptor 38 (Olfr38) | 2.39 |
| NM_146616 | Olfactory receptor 305 (Olfr305) | 2.21 |
| NM_146339 | Olfactory receptor 77 (Olfr77) | 0.50 |

TABLE 17-continued

Profile for olfactory receptors in which the expression is changed by anti-obesity substance

| GenBank accession No. | Gene name (Gene symbol) | Expression fold change to HFD group |
|---|---|---|
| Piperine (liver tissue) | | |
| NM_146798 | Olfactory receptor 878 (Olfr878) | 5.56 |
| NM_146986 | Olfactory receptor 38 (Olfr38) | 3.93 |
| NM_147063 | Olfactory receptor 520 (Olfr520) | 2.24 |
| NM_146693 | Olfactory receptor 1462 (Olfr1462) | 0.49 |
| NM_146339 | Olfactory receptor 77 (Olfr77) | 0.42 |
| α-Cedrene (liver tissue) | | |
| NM_146798 | Olfactory receptor 878 (Olfr878) | 5.87 |
| NM_146986 | Olfactory receptor 38 (Olfr38) | 3.83 |
| NM_001011860 | Olfactory receptor 1222 (Olfr1222) | 2.15 |
| NM_147017 | Olfactory receptor 1045 (Olfr1045) | 0.43 |

TABLE 18

Olfactory receptors in which the expression is changed by anti-obesity substance

| | | visceral fat tissue | | | liver tissue | | | | |
|---|---|---|---|---|---|---|---|---|---|
| GenBank accession No. | Gene symbol | indol-3-carbinol | oleuropein | cedryl acetate | indol-3-carbinol | oleuropein | piperine | cedryl acetate | α-cedrene |
| NM_146798 | Olfr878 | | | | | | 5.56 | 2.76 | 5.87 |
| NM_146339 | Olfr77 | | | | | | 0.42 | 0.5 | |
| NM_147063 | Olfr520 | | 2.08 | | | | 2.24 | | |
| NM_147025 | Olfr380 | 2.2 | | 2.14 | | | | | |
| NM_146986 | Olfr38 | | | | 2.35 | | 3.93 | 2.39 | 3.83 |
| NM_146950 | Olfr341 | | 0.3 | 0.32 | | | | | |
| NM_146416 | Olfr290 | | 2.32 | 2.40 | 2.11 | | | | |
| NM_146858 | Olfr275 | | | | | 2.49 | | 2.64 | |
| NM_146693 | Olfr1462 | 2.26 | | | | | 0.49 | | |
| NM_146648 | Olfr1165 | 0.39 | | 0.36 | | | | | |
| NM_146659 | Olfr1136 | | | 0.43 | | 0.49 | | | |
| NM_146767 | Olfr1104 | | 4.39 | 3.22 | | | | | |
| NM_147017 | Olfr1045 | | | | 0.45 | | | | 0.43 |

* The numbers in the table indicate changes of gene expression in the odor component-supplemented group, to the HFD group.

Example 3

Obesity and Metabolic Diseases-Related Gene Expression Changes by the Intake of Odor Components Having Anti-Obesity Efficacy 1) RNA Extraction Using Trizol Method and RT-PCR After adding 1 mL of Trizol agent (Invitrogen, USA) per 0.1 g of visceral fat or liver tissues, the mixture was homogenized and centrifuged at 12,000×g for 10 min at 4° C. The supernatant was transferred to a new tube and 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

The RNA sample obtained from the visceral fat or liver tissues was trasnscribed using oligo dT primer and reverse transcriptase (GIBCO BRL, Gaithersburg, Md., USA) to synthesize cDNA. The PCR amplification was performed using the cDNA as templates and primers complementary to cDNA 5' and 3' flanking sequence. The sequences of the primers used are presented in Table 19. 1 μl of the amplified products were resolved on agarose gel electrophoresis to verify DNA band.

TABLE 19

Primer sequences for RT-PCR

| Gene | | Primer Sequence(5' → 3') | Anealing Temp (° C.) | Size of PCR product (bp) |
|---|---|---|---|---|
| PPARγ2 (Peroxisome proliferator activated receptor gamma) | F | TTCGGAATCAGCTCTGTGGA (SEQ ID NO: 1) | 55 | 148 |
| | R | CCATTGGGTCAGCTCTTGTG (SEQ ID NO: 2) | | |
| aP2 (Fatty acid binding protein) | F | AGCATCATAACCCTAGATGG (SEQ ID NO: 3) | 55 | 128 |
| | R | GAAGTCACGCCTTTCATAAC (SEQ ID NO: 4) | | |
| C/EBPα (CCAAT/enhancer binding protein alpha) | F | TCGGTGCGTCTAAGATGAGG (SEQ ID NO: 5) | 55 | 187 |
| | R | TCAAGGCACATTTTTGCTCC (SEQ ID NO: 6) | | |

TABLE 19-continued

Primer sequences for RT-PCR

| Gene | | Primer Sequence (5' → 3') | Anealing Temp (° C.) | Size of PCR product (bp) |
|---|---|---|---|---|
| FAS (fatty acid synthase) | F | TTGCCCGAGTCAGAGAACC (SEQ ID NO: 7) | 55 | 185 |
| | R | CGTCCACAATAGCTTCATAGC (SEQ ID NO: 8) | | |
| TNFα (TNFalpha) | F | TGTCTCAGCCTCTTCTCATT (SEQ ID NO: 9) | 55 | 156 |
| | R | AGATGATCTGAGTGTGAGGG (SEQ ID NO: 10) | | |
| IL-6 (Intereukin 6) | F | ATGAAGTTCCTCTCTGCAAGAGACT (SEQ ID NO: 11) | 55 | 638 |
| | R | CACTAGGTTTGCCGAGTAGATCTC (SEQ ID NO: 12) | | |
| CPT1 (carnitine palmitoyltransferase 1) | F | CAGAACACGGCAAAATGAGC (SEQ ID NO: 13) | 55 | 207 |
| | R | GAGGTTGACAGCAAAATCCTG (SEQ ID NO: 14) | | |
| PGC1α (PPAR-gamma coactivator 1-alpha) | F | ACTGACAGATGGAGCCGTGA (SEQ ID NO: 15) | 55 | 145 |
| | R | GCTGCATGGTTCTGAGTGCT (SEQ ID NO: 16) | | |
| UCP1 (Uncouplin protein 1) | F | GGGACCTACAATGCTTACAG (SEQ ID NO: 17) | 55 | 103 |
| | R | GGTCATATGTCACCAGCTCT (SEQ ID NO: 18) | | |
| UCP3 (Uncouplin protein 3) | F | ACGGATGTGGTGAAGGTCCG (SEQ ID NO: 19) | 55 | 464 |
| | R | TACAAACATCATCACGTTCC (SEQ ID NO: 20) | | |
| GAPDH (Glyceraldehyde-3-phosphatedehydrogenase) | F | AGAACATCATCCCTGCATCC (SEQ ID NO: 21) | 55 | 321 |
| | R | TCCACCACCCTGTTGCTGTA (SEQ ID NO: 22) | | |
| SIRT1 (sirtuin 1) | F | TGACGACTTCGACTTCGACGACG (SEQ ID NO: 23) | 55 | 182 |
| | R | TAGGGCACCGAGGAATACC (SEQ ID NO: 24) | | |

2) Protein Extraction and Western Blotting

A certain amount of visceral fat or liver tissues in mortar was homogenized with liquid nitrogen and cell lysis buffer. The mixture was transferred to a new tube, followed by vortexing. After centrifugation at 13,000×g for 20 min at 4° C., the middle layer of the tube was obtained and proteins were quantified by Bradford method. 50 μg of protein was electrophorized to SDS polyacrylamide gel, followed by electroblotting to PVDF hyper film. The protein was reacted using an appropriate antibody for the protein and detected by ECL, whereby insulin resistance, adipocyte differentiation, lipid metabolism or energy consumption-related mechanism of phytochemical components was investigated in the protein level.

3) Changes in Obesity and Metabolic Diseases-Related Gene Expression and Protein Phosphorylation by Odor Components The dysfunction of mitochondria is related to senescence, heart diseases and gastrointestinal, endocrine and neurological disorders. The damages of the oxidation process in mitochondria increase glucose production in liver tissues and hyperglycemia, finally causing fatty liver. The mitochondria forms proton gradient across its inner and outer membranes by the electron transport chain, and generates ATP through F0F1-ATPase using the proton gradient as a driving force. Where F0F1-ATPase is not normally worked, the proton gradient disappears through uncoupling proteins to generate heat. In current, it has been reported that UCPs in adipose tissues promotes thermogenesis with maintaining redox balance by the energy-dissipatory mechanism, and gene expressions of both of UCP1 and UCP3 are significantly decreased in visceral fat tissue of diet-induced obesity mouse as compared to the normal control group.

Adipogenesis is a process in which preadipocytes are proliferated and differentiated to adipocytes, which is accompanied with changes of cell morphology and gene expression profiles. i.e., in adipogenesis, lipids are accumulated and adipocyte-specific genes such as aP2 (fatty acid binding protein 2), LPL (lipoprotein lipase) and FAS (fatty acid synthase) are expressed under controls of three transcription factors including PPARy (Peroxisome proliferator activated receptor gamma), C/EBPs (CCAAT enhancer-binding proteins) and SREBP-1c (sterol regulatory binding protein-1c). Therefore, it has been known that once diet-induced obesity is induced, gene expressions of both of these adipogenesis transcription factors and their target genes are significantly increased in visceral fat and liver tissue. Moreover, once obesity is progressed, metaflammation is progressed by increasing the secretion of proinflammatory cytokines (e.g., TNF-α and IL-6) as well as leptin in visceral fat tissue.

NAFLD (non-alcoholic fatty liver disease) refers to a liver disease associated with triglyceride accumulation in the liver regardless of drinking alcohols, including simple steatosis and NASH (non-alcoholic steatohepatitis). Simple steatosis is considered benign diseases with good prognosis in clinic, but NASH accompanied with fatty liver, inflammation or fibrosis is recognized as progressive liver diseases inducing cirrhosis or liver cancer. The obesity and the insulin resistance are representative of risk factors for NAFLD. The pathogenesis of non-alcoholic fatty liver may be explained by two mechanisms. The first mechanism is that the increase in free fatty adds inhibits fatty acid oxidation in hepatocytes, thereby accumulating fatty acids in hepatocytes to cause non-alcoholic fatty liver. The second mechanism involves a variety of physiological factors associated with inflammation and fibrosis progression. i.e., the increase in levels of fatty acid induces to elevate the expression of CYP2E1 (cytochrome peroxidase 2E1) and to generate reactive oxygen species resulting in lipid peroxidation of liver cell membrane, and the increase in oxidative stress increases the level of TNF-α being responsible for apoptosis of hepatocytes, finally inducing liver damage.

In the present invention, the gene expressions of visceral fat and liver tissues were evaluated by RT-PCR analysis. Mice supplemented to the odor components having anti-obesity efficacy showed decreased expressions of nuclear transcription factors (C/EBPα and PPARγ2) and their target genes (aP2 and FAS) in visceral fat tissue, as compared to the control group fed HFD. In addition, the supplement of odor components showed decreased expressions of TNF-α and IL-6 which cause metaflammation. In contrast, it was observed that the supplement of odor components has effects for increasing expressions of CPT1 involved in fatty acid oxidation, UCP1 and UCP3 involved in thermogenesis, and SIRT1 and PGC1a regulating their target gene expression (Table 8). Accordingly, it may be understood that the supplement of odor components having anti-obesity efficacy decreases expressions of nuclear transcription factors and their target genes which play a pivotal role for adipogenesis in visceral fat tissue, promotes fatty acid oxidation and thermogenesis to reduce body weight, and significantly improves chronic inflammatory responses induced by obesity, whereby metabolic diseases are totally improved.

In addition, in the present invention, the gene expressions of liver tissue were evaluated by RT-PCR analysis. Mice supplemented to the odor components having anti-obesity efficacy showed decreased expressions of nuclear transcription factors (C/EBPa and PPARγ2) and their target genes (aP2 and FAS) involved in adipogenesis, as compared to the control group fed HFD. In addition, it showed decreased expressions of TNF-α and IL-6 which play a pivotal role in progressive process of simple steatosis to steatohepatitis. However, expression of CPT1 promoting fatty acid oxidation was significantly increased (Table 20). Accordingly, it may be understood that the supplement of odor components having efficacy for decreasing body weight decreases expressions of nuclear transcription factors and their target genes involved in adipogenesis in liver tissue, promotes fatty acid oxidation to prevent generation of fatty liver, and significantly improves inflammatory responses in liver tissue, whereby non-alcoholic steatohepatitis is improved.

Figure 3:
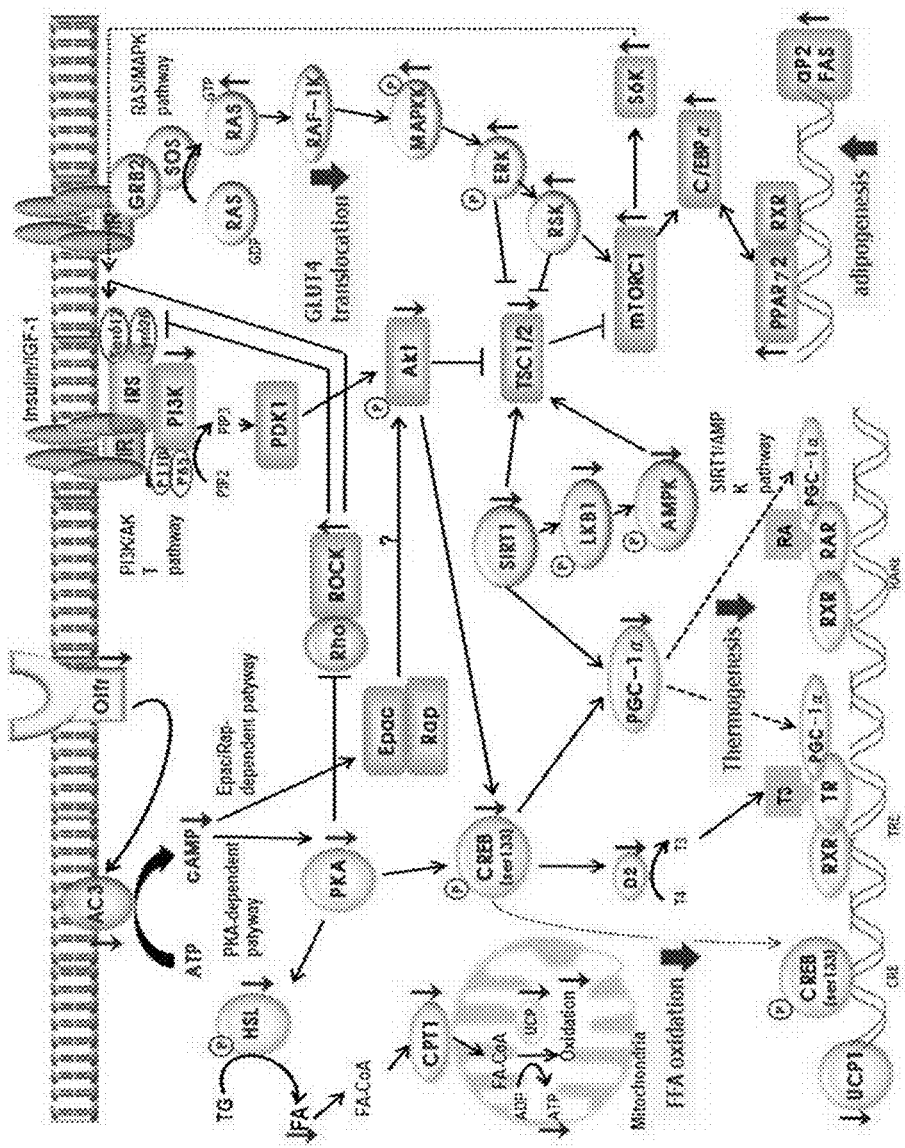
FIG. 3 schematically represents the signal pathway related fatty acid oxidation, thermogenesis, fat accumulation and insulin resistance. AC (adenylate cyclase); AMPK (AMP-activated protein kinase); AKT (v-akt murine thymoma viral oncogene); CPT1 (carnitiine palmitoyltransferase1); CREB (cAMP-responsive element binding protein); D2 (typeII thyroxine deiodinase); Epac (Rap guanine nucleotide exchange factor3); ERK (extracellular signal regulated kinase); GRB2 (growth factor receptor-bound protein 2); HSL (hormone sensitive lipase); IR (insulin receptor); IRS (insulin receptor substrate); LKB (STK11, serine/threonine kinase 11); MAPK (mitogen-activated protein kinase); Olfr (olfactory receptor); PDK (pyruvate dehydrogenase kinase, isozyme 1); PKA (protein kinase A); PGC-1 (PPARycoactivator 1); RAR (retinoic acid receptor); RAF (RAF proto-oncogene serine/threonine-protein kinase); ROCK (Rho-associated kinase); RXR (retinoic acid receptor); T3 (triiodothyronine); mTORC1 (mammalian target of rapamycin complex 1); TR (thyroid hormone receptor); TSC2 (tuberous sclerosis2); UCP (uncoupling protein)

It would be understood that various obesity and metabolic diseases-related genes described above were ultimately mediated by olfactory receptor/$AC_3$ at upstream (FIG. 3). In order to verify this, protein phosphorylations of HSL (hormone sensitive lipase), CREB (cAMP-responsive element binding protein) and AKT (v-akt murine thymoma viral oncogene) were evaluated by western blotting analysis. As a result, it was observed that the phosphorylation of these 3 proteins in mice supplemented odor components (indol-3-carbinol, oleuropein, cedryl acetate and piperine) were significantly increased as compared to the HFD control group (Table 21). Accordingly, it would be determined that olfactory receptors are a novel target of therapeutic agents for obesity and metabolic diseases since $AC_3$ is an upstream molecule regulating translocation of GLUT4 which is involved in adipogenesis, free fatty acid oxidation, thermogenesis and insulin resistance, and signals are simultaneously transmitted by olfactory receptors.

TABLE 21

Changes in obesity-related gene expression by various types of odor components having anti-obesity efficacy

| | indol-3-carbinol | oleuropein | cedryl acetate | piperine |
|---|---|---|---|---|
| HSL phosphorylation | 31% increase [a] | 52% increase | 46% increase | 45% increase |
| CREB phosphorylation | 45% increase | 60% increase | 39% increase | 29% increase |
| AKT phosphorylation | 40% increase | 59% increase | 33% increase | 47% increase |

[a] indicates change rate of gene expression in the odor component-supplemented group, to the HFD control group.

Having described a preferred embodiment of the present invention, it is to be understood that variants and modifications thereof falling within the spirit of the invention may become apparent to those skilled in this art, and the scope of this invention is to be determined by appended claims and their equivalents.

TABLE 20

Changes in obesity-related gene expression by various types of odor components having anti-obesity efficacy

| | indol-3-carbinol | | oleuropein | | cedryl acetate | piperine | |
|---|---|---|---|---|---|---|---|
| | fat tissue | liver tissue | fat tissue | liver tissue | fat tissue | fat tissue | liver tissue |
| C/EBPα | 11% decrease[a] | 25% decrease | 22% decrease | 16% decrease | 36% decrease | 35% decrease | 8% decrease |
| PPARγ2 | 20% decrease | 36% decrease | 35% decrease | 94% decrease | 25% decrease | 30% decrease | 44% decrease |
| aP2 | 44% decrease | 29% decrease | 26% decrease | 29% decrease | 33% decrease | 60% decrease | 55% decrease |
| FAS | 56% decrease | 27% decrease | 65 decrease | 40% decrease | 43% decrease | 52% decrease | 67% decrease |
| CPT1 | 25% increase | 33% increase | 50% increase | 33% increase | 47% increase | 75% increase | 44% increase |
| TNFα | 23% decrease | 33% decrease | 66% decrease | 60% decrease | 99% decrease | 75% decrease | 60% decrease |
| IL-6 | 76% decrease | 45% decrease | 78% decrease | 62% decrease | 74% decrease | 83% decrease | 71% decrease |
| SIRT1 | 45% increase | | 98% increase | | 650% increase | 36% increase | |
| PGC1α | 120% increase | | 210% increase | | 57% increase | 324% increase | |
| UCP1 | 210% increase | | 450% increase | | 899% increase | 905% increase | |
| UCP3 | 72% increase | | 82% increase | | 65% increase | 75% increase | |

[a] indicates change rate of gene expression in the odor component-supplemented group, to the HFD control group.

What is claimed is:

1. A method of screening for a candidate therapeutic composition that may be useful for treating a metabolic disease, induced by high fat diet (HFD), selected from the group consisting of dyslipidemia, fatty liver and insulin resistance syndrome, comprising:
 (a) contacting a sample of interest for analysis with a fat cell or muscle cell comprising the nucleotide sequence of SEQ ID NO:25; and
 (b) analyzing the expression level of the nucleotide sequence in the cell,
 wherein when the expression level of the nucleotide sequence of SEQ ID NO:25 is increased by the sample to he analyzed more than 2-fold from the level before treatment with the sample, then the sample is determined to be a candidate therapeutic composition that may be useful for treating the HFD induced metabolic disease.

2. The method of claim 1, wherein the metabolic disease is dyslipidemia.

3. The method of claim 1, wherein the metabolic disease is fatty liver.

4. The method of claim 1, wherein the metabolic disease is insulin resistance syndrome.

* * * * *